US011351200B2

(12) United States Patent
Marban et al.

(10) Patent No.: US 11,351,200 B2
(45) Date of Patent: Jun. 7, 2022

(54) CDC-DERIVED EXOSOMES FOR TREATMENT OF VENTRICULAR TACHYARRYTHMIAS

(71) Applicant: Cedars-Sinai Medical Center, Los Angeles, CA (US)

(72) Inventors: Eduardo Marban, Santa Monica, CA (US); Eugenio Cingolani, Marina Del Rey, CA (US); James Dawkins, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 16/305,011

(22) PCT Filed: Jun. 2, 2017

(86) PCT No.: PCT/US2017/035846
§ 371 (c)(1),
(2) Date: Nov. 27, 2018

(87) PCT Pub. No.: WO2017/210652
PCT Pub. Date: Dec. 7, 2017

(65) Prior Publication Data
US 2019/0160111 A1    May 30, 2019

Related U.S. Application Data

(60) Provisional application No. 62/345,694, filed on Jun. 3, 2016, provisional application No. 62/504,805, filed on May 11, 2017.

(51) Int. Cl.
| | |
|---|---|
| *A61K 35/34* | (2015.01) |
| *C12N 5/00* | (2006.01) |
| *A61K 35/12* | (2015.01) |
| *A61P 9/10* | (2006.01) |
| *A61P 9/06* | (2006.01) |
| *A61K 9/00* | (2006.01) |
| *A61N 1/39* | (2006.01) |

(52) U.S. Cl.
CPC ............ *A61K 35/34* (2013.01); *A61K 9/0019* (2013.01); *A61K 35/12* (2013.01); *A61P 9/06* (2018.01); *A61P 9/10* (2018.01); *A61N 1/3956* (2013.01)

(58) Field of Classification Search
CPC ...... A61K 35/34; A61K 35/12; A61K 9/0019; A61P 9/06
See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |
| 5,028,588 A | 7/1991 | Hoffman et al. |
| 5,052,402 A | 10/1991 | Bencini et al. |
| 5,104,787 A | 4/1992 | Lindstrom et al. |
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |

(Continued)

FOREIGN PATENT DOCUMENTS

| | | |
|---|---|---|
| CA | 2488346 | 12/2003 |
| CN | 1537646 | 10/2004 |
| CN | 1772300 | 5/2006 |
| CN | 1785430 | 6/2006 |
| EP | 1 254 952 | 11/2002 |

(Continued)

OTHER PUBLICATIONS

Dib et al., 2011, J. of Cardiovasc. Trans. Res., 4:177-181.*
Wu et al., 2012, Aging Research reviews, vol. 11, p. 32-40.*
Agrahari et al., 2017, Expert Opinion on Drug Delivery, vol. 14, No. 10, p. 1145-1162.*
Ikehara et al., 2013, Frontier in Cell and Developmental Biology, vol. 1, Article 2, p. 1-2.*

(Continued)

*Primary Examiner* — Shin Lin Chen
(74) *Attorney, Agent, or Firm* — Knobbe, Martens, Olson & Bear, LLP

(57) ABSTRACT

Described herein are compositions and methods related to use of exosomes, including cardiosphere derived cell (CDC)-derived exosomes for treatment and prevention of heart related disease and conditions, such as ventral arrhythmias, such as tachycardias. CDC-derived exosomes delivered by endocardial injection can diminish the total amount of isolated late potentials associated with an isthmus of slow conduction, while reducing the isoelectric interval between late abnormal ventricular activity and decreasing the incidence of inducible ventricular arrhythmias, thereby providing a biological treatment for arrhythmias which otherwise requires therapeutic interventions with adverse effects.

8 Claims, 30 Drawing Sheets

(56) References Cited

U.S. PATENT DOCUMENTS

| | | |
|---|---|---|
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,872,109 A | 2/1999 | Akima et al. |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marbán et al. |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 | 11/2017 | Marbán et al. |
| 9,845,457 B2 | 12/2017 | Marbán et al. |
| 9,884,076 B2 | 2/2018 | Kreke et al. |
| 10,457,942 B2 | 10/2019 | Marbán et al. |
| 11,220,687 B2 | 1/2022 | Marbán et al. |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0126879 A1 | 7/2004 | Schneider et al. |
| 2004/0136966 A1 | 7/2004 | Anversa et al. |
| 2004/0137621 A1 | 7/2004 | Rosen et al. |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |
| 2005/0176620 A1 | 8/2005 | Prestwich et al. |
| 2005/0214938 A1 | 9/2005 | Gold et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |

(56) References Cited

U.S. PATENT DOCUMENTS

| | | |
|---|---|---|
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0286848 A1 | 12/2007 | Louis-Georges et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1 | 3/2010 | Marbán et al. |
| 2010/0081200 A1 | 4/2010 | Rajala et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0091448 A1 | 4/2011 | Moon et al. |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2012/0258093 A1 | 10/2012 | Butler-Browne et al. |
| 2012/0315252 A1 | 12/2012 | Marbán et al. |
| 2013/0059006 A1 | 3/2013 | Schmuck et al. |
| 2013/0177593 A1 | 7/2013 | Gunn et al. |
| 2013/0189780 A1 | 7/2013 | Shoemaker et al. |
| 2013/0266543 A1 | 10/2013 | Nadal-Ginard |
| 2013/0280205 A1 | 10/2013 | Mozaffari et al. |
| 2013/0288962 A1 | 10/2013 | Anversa et al. |
| 2013/0295060 A1 | 11/2013 | Yang et al. |
| 2013/0309304 A1 | 11/2013 | Nadal-Ginard |
| 2014/0031256 A1 | 1/2014 | Lim |
| 2014/0120066 A1 | 5/2014 | Yeghiazarians et al. |
| 2014/0121171 A1 | 5/2014 | Muñoz-Cánoves et al. |
| 2014/0156200 A1 | 6/2014 | Verhaegh et al. |
| 2014/0235526 A1 | 8/2014 | Srivastava et al. |
| 2014/0275976 A1 | 9/2014 | Moro |
| 2015/0010640 A1 | 1/2015 | Marbán et al. |
| 2015/0140658 A1 | 5/2015 | Kamp et al. |
| 2015/0246030 A1 | 9/2015 | Armer et al. |
| 2015/0273113 A1 | 10/2015 | Marbán et al. |
| 2015/0328263 A1 | 11/2015 | Kaushal |
| 2016/0158291 A1 | 6/2016 | Kreke et al. |
| 2016/0244723 A1 | 8/2016 | Giacomello et al. |
| 2017/0037375 A1 | 2/2017 | Palecek et al. |
| 2017/0049793 A1 | 2/2017 | Moon et al. |
| 2017/0087087 A1 | 3/2017 | Leonard et al. |
| 2017/0290860 A1 | 10/2017 | Marbán et al. |
| 2017/0304368 A1 | 10/2017 | Marbán et al. |
| 2018/0100149 A1 | 4/2018 | Marbán et al. |
| 2019/0000888 A1 | 1/2019 | Marbán et al. |
| 2019/0062740 A1 | 2/2019 | Zhu |
| 2019/0255119 A1 | 8/2019 | Marbán et al. |
| 2020/0024604 A1 | 1/2020 | Marbán et al. |
| 2020/0121727 A1 | 4/2020 | Marbán et al. |

(56) References Cited

U.S. PATENT DOCUMENTS

| | | | |
|---|---|---|---|
| 2020/0316226 | A1 | 10/2020 | Marbán et al. |
| 2021/0032598 | A1 | 2/2021 | Ibrahim et al. |
| 2021/0085724 | A1 | 3/2021 | Marbán et al. |
| 2021/0207145 | A1 | 7/2021 | Marbán et al. |
| 2021/0401896 | A1 | 12/2021 | Marbán et al. |

FOREIGN PATENT DOCUMENTS

| | | |
|---|---|---|
| EP | 1 857 544 | 11/2007 |
| EP | 1 970 446 | 9/2008 |
| EP | 2 182 053 | 5/2010 |
| EP | 2 228 444 | 9/2010 |
| EP | 1 631 318 | 11/2010 |
| EP | 1 650 293 | 12/2010 |
| EP | 2 371 370 | 10/2011 |
| EP | 2385120 | 11/2011 |
| EP | 2 446 929 | 5/2012 |
| EP | 1 945 256 | 7/2012 |
| EP | 2 094 869 | 7/2012 |
| EP | 2 486 944 | 8/2012 |
| EP | 2 277 548 | 1/2013 |
| EP | 2 687 219 | 1/2014 |
| JP | 2005-506845 | 3/2005 |
| JP | 2005-110565 | 4/2005 |
| JP | 2006-006125 | 1/2006 |
| JP | 2008-504816 | 2/2008 |
| JP | 2008-518730 | 6/2008 |
| KR | 100830889 | 5/2008 |
| KR | 101818560 | * 11/2016 |
| WO | WO 97/005265 | 2/1997 |
| WO | WO 97/012912 | 4/1997 |
| WO | WO 98/004708 | 2/1998 |
| WO | WO 98/032866 | 7/1998 |
| WO | WO 99/011809 | 3/1999 |
| WO | WO 99/039624 | 8/1999 |
| WO | WO 99/049015 | 9/1999 |
| WO | WO 99/051297 | 10/1999 |
| WO | WO 00/009185 | 2/2000 |
| WO | WO 00/024452 | 5/2000 |
| WO | WO 01/010482 | 2/2001 |
| WO | WO 01/026585 | 4/2001 |
| WO | WO 01/026706 | 4/2001 |
| WO | WO 01/026727 | 4/2001 |
| WO | WO 01/048151 | 7/2001 |
| WO | WO 01/076679 | 10/2001 |
| WO | WO 01/076682 | 10/2001 |
| WO | WO 02/009650 | 2/2002 |
| WO | WO 02/013760 | 2/2002 |
| WO | WO 02/051489 | 7/2002 |
| WO | WO 03/004626 | 1/2003 |
| WO | WO 03/006950 | 1/2003 |
| WO | WO 03/008535 | 1/2003 |
| WO | WO 03/049626 | 6/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/007529 | 1/2006 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO 2008/036776 | 3/2008 |
| WO | WO 2008/043521 | 4/2008 |
| WO | WO 2008/058216 | 5/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO 2009/056116 | 5/2009 |
| WO | WO 2009/058818 | 5/2009 |
| WO | WO 2009/062143 | 5/2009 |
| WO | WO 2009/062169 | 5/2009 |
| WO | WO 2009/067644 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/100137 | 8/2009 |
| WO | WO 2009/103818 | 8/2009 |
| WO | WO 2009/149956 | 12/2009 |
| WO | WO 2009/152111 | 12/2009 |
| WO | WO 2010/015665 | 2/2010 |
| WO | WO 2010/028090 | 3/2010 |
| WO | WO 2010/033285 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO 2011/029092 | 3/2011 |
| WO | WO 2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO 2011/062244 | 5/2011 |
| WO | WO 2011/064354 | 6/2011 |
| WO | WO 2011/084460 | 7/2011 |
| WO | WO 2011/121120 | 10/2011 |
| WO | WO 2011/127625 | 10/2011 |
| WO | WO 2011/138328 | 11/2011 |
| WO | WO 2011/143499 | 11/2011 |
| WO | WO 2012/019103 | 2/2012 |
| WO | WO 2012/020307 | 2/2012 |
| WO | WO 2012/020308 | 2/2012 |
| WO | WO 2012/055971 | 5/2012 |
| WO | WO 2012/065027 | 5/2012 |
| WO | WO 2012/125471 | 9/2012 |
| WO | WO 2012/135253 | 10/2012 |
| WO | WO 2012/149557 | 11/2012 |
| WO | WO 2012/162741 | 12/2012 |
| WO | WO 2013/048734 | 4/2013 |
| WO | WO 2013/170170 | 11/2013 |
| WO | WO 2013/184527 | 12/2013 |
| WO | WO 2014/013258 | 1/2014 |
| WO | WO 2014/028493 | 2/2014 |
| WO | WO 2014/114465 | 7/2014 |
| WO | WO 2014/160153 | 10/2014 |
| WO | WO 2015/055857 | 4/2015 |
| WO | WO 2015/085096 | 6/2015 |
| WO | WO 2015/092020 | 6/2015 |
| WO | WO 2015/120150 | 8/2015 |
| WO | WO 2016/054591 | 4/2016 |
| WO | WO 2016/057560 | 4/2016 |
| WO | WO 2017/160884 | 9/2017 |
| WO | WO 2017/173034 | 10/2017 |
| WO | WO 2019/015702 | 1/2019 |
| WO | WO 2019/028223 | 2/2019 |
| WO | WO 2019/050071 | 3/2019 |
| WO | WO 2019/126068 | 6/2019 |
| WO | WO 2019/152549 | 8/2019 |
| WO | WO 2020/227489 | 11/2020 |
| WO | WO 2021/178514 | 9/2021 |
| WO | WO 2021/188899 | 9/2021 |
| WO | WO 2021/237238 | 11/2021 |

OTHER PUBLICATIONS

Cooper et al., 2015, International Journal of Surgery, vol. 23, p. 211-216.*
Liu et al., 2017, Frontiers in Immunology, vol. 8, article 645, p. 1-6.*
Barile et al., 2013, Stem Cells International, vol. 2013, Article ID 916837, pp. 1-10.*
Shimasaki et al., 2018, Biol. Pharm. Bull., vol. 41, p. 1311-1321.*
Cheng et al., 2017, Stem Cells International, vol. 2017, Article ID 6305295, p. 1-10.*
Bryan et al., 2013, http://www.elsevierblogs.com/currentcomments/?p=962, Implications of protein fold switching, p. 1-4.*

(56) References Cited

OTHER PUBLICATIONS

Maqbool et al., 2015, Biochemical Society Transactions, vol. 43, No. 5, p. 1011-1017.*
Wang et al., 2021, Journal of Controlled Release, vol. 329, p. 894-906.*
Zhao et al., 2020, Biomedicine and Pharmacotherapy, vol. 128, 110237, p. 1-9.*
Cheng et al., 2017, Stem Cells International, vol. 2017, Article ID 6305295, 10 pages.*
Abdel-Latif et al., "Adult Bone Marrow-Derived Cells for Cardiac Repair: A Systematic Review and Meta-Analysis", Archives of Internal Medicine, vol. 167, May 28, 2007, pp. 989-997.
Abela et al., "A New Method for Isolation of Cardiac Myocytes by Percutaneous Endomyocardial Biopsy", Catheterization and Cardiovascular Diagnosis, 1996, vol. 37, pp. 227-230.
Ajijola et al., "Ventricular Tachycardia in Ischemic Heart Disease Substrates", Indian Heart Journal, 2014, pp. S24-S34, S28 & S30, vol. 66, Supplement 1.
Albini et al., "A Rapid in Vitro Assay for Quantitating the Invasive Potential of Tumor Cells", Cancer Research, Jun. 15, 1987, pp. 3239-3245, vol. 47.
Ames et al., "Oxidants, Antioxidants, and the Degenerative Diseases of Aging", Proceedings of the National Academy of Sciences of the United States of America, Sep. 1993, vol. 90, pp. 7915-7922.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Andersen et al., "Murine 'Cardiospheres' Are Not a Source of Stem Cells with Cardiomyogenic Potential," Stem Cells, 2009, vol. 27, No. 7, pp. 1571-1581.
Anversa et al., "Primitive Cells and Tissue Regeneration", Circulation Research, 2003, vol. 92, pp. 579-582.
Assmus et al., "Transplantation of Progenitor Cells and Regeneration Enhancement in Acute Myocardial Infarction (TOPCARE-AMI)", Circulation, Dec. 10, 2002, vol. 106, pp. 3009-3017.
"ATS/ACCP Statement on Cardiopulmonary Exercise Testing", American Thoracic Society/American College of Chest Physicians, American Journal of Respiratory and Critical Care Medicine, 2003, vol. 167, pp. 211-277.
Ausma et al., "Dedifferentiation of Atrial Cardiomyocytes: From in Vivo to In Vitro", Cardiovascular Research, Jul. 2002, vol. 55, No. 1, pp. 9-12.
Baker et al. "Adaptation to Culture of Human Embryonic Stem Cells and Oncogenesis in Vivo" Nature Biotechnology, Feb. 2007, vol. 25, No. 2, pp. 207-215.
Balser et al., "Global Parameter Optimization for Cardiac Potassium Channel Gating Models", Biophysical Journal, Mar. 1990, vol. 57, pp. 433-444.
Balser et al., "Local Anesthetics as Effectors of Allosteric Gating", Journal of Clinical Investigation, Dec. 1996, vol. 98, No. 12, pp. 2874-2886.
Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, vol. 108, pp. 863-868.
Barile et al., "Cardiac Stem Cells: Isolation, Expansion and Experimental use for Myocardial Regeneration", Nature Clinical Practice Cardiovascular Medicine, Feb. 2007, vol. 4, No. 1, pp. S9-S14.
Barile et al., "Endogenous Cardiac Stem Cells", Progress in Cardiovascular Diseases, Jul.-Aug. 2007, vol. 50, No. 1, pp. 31-48.
Barr et al., "Efficient Catheter-Mediated Gene Transfer Into the Heart Using Replication-Defective Adenovirus", Gene Therapy, Jan. 1994, vol. 1, No. 1, pp. 51-58.
Barry et al., "Differential Expression of Voltage-Gated $K^+$ Channel Subunits in Adult Rat Heart", Circulation Research, 1995, vol. 77, pp. 361-369.

Barth et al., "Lentiviral Vectors Bearing the Cardiac Promoter of the $Na^+$-$Ca^{2+}$ Exchanger Report Cardiogenic Differentiation in Stem Cells", Molecular Therapy, May 2008, vol. 16, No. 5, pp. 957-964.
Bearzi et al., "Human Cardiac Stem Cells", Proceedings of the National Academy of Sciences of the United States of America (PNAS), Aug. 28, 2007, pp. 14068-14073, vol. 104, No. 35.
Beltrami et al., "Adult Cardiac Stem Cells are Multipotent and Support Myocardial Regeneration", Cell, Sep. 19, 2003, vol. 114, No. 6, pp. 763-776.
Beltrami et al., "Evidence That Human Cardiac Myocytes Divide After Myocardial Infarction", The New England Journal of Medicine, Jun. 7, 2001, vol. 344, pp. 1750-1757.
Beltrami et al., "Multipotent Cells Can be Generated In Vitro from Several Adult Human Organs (Heart, Liver and Bone Marrow)", Stem Cells in Hematology, Blood, 2007, pp. 3438-3446, vol. 110, No. 9.
Bénardeau et al., "Primary Culture of Human Atrial Myocytes is Associated with the Appearance of Structural and Functional Characteristics of Immature Myocardium", Journal of Molecular and Cellular Cardiology, 1997, vol. 29, pp. 1307-1320.
Bergmann et al., "Evidence for Cardiomyocyte Renewal in Humans", Science, Apr. 3, 2009, vol. 324, pp. 98-102.
Bernanke et al., "Effects of Hyaluronic Acid on Cardiac Cushion Tissue Cells in Collagen Matrix Cultures", Texas Reports on Biology and Medicine, 1979, pp. 271-285, vol. 39.
"Bioptome.com", Scholten Surgical Instruments, Inc., downloaded from http://www.bioptome.com/pages.php?page=Products, 2001, first date of publication unknown, printed on Nov. 1, 2005, pp. 2.
Bird et al., "The Human Adult Cardiomyocyte Phenotype", Cardiovascular Research, May 1, 2003, vol. 58, No. 2, pp. 423-434.
Birks et al., "Left Ventricular Assist Device and Drug Therapy for the Reversal of Heart Failure", The New England Journal of Medicine, 2006, vol. 355, No. 18, pp. 1873-1884.
Bjelakovic et al., "Mortality in Randomized Trials of Antioxidant Supplements for Primary and Secondary Prevention: Systematic Review and Meta-Analysis", JAMA, 2007, vol. 297, pp. 842-857.
Bosnali et al., "Generation of Transducible Versions of Transcription Factors Oct4 and Sox2", Biological Chemistry, Jul. 2008, vol. 389, pp. 851-861.
Bredemeyer et al., "ATM Stabilizes DNA Double-Strand-Break Complexes During V(D)J Recombination", Nature, Jul. 27, 2006, vol. 442, pp. 466-470.
Burstein et al., "Systemic and Coronary Delivery of Marrow Stromal Cells for Cellular Cardiomyoplasty: Advantages and Precautions", Basic and Applied Myology, 2003, vol. 13, No. 1, pp. 7-10.
Cai et al., "Injectable Glycosaminoglycan Hydrogels for Controlled Release of Human Basic Fibroblast Growth Factor," Biomaterials, 2005, vol. 26, pp. 6054-6067.
"CArdiosphere-Derived aUtologous StemCElls to Reverse ventricUlar dysfunction (CADUCEUS)", ClinicalTrials.gov, Identifier NCT00893360, 2009, pp. 6.
Chambers et al., "Functional Expression Cloning of Nanog, a Pluripotency Sustaining Factor in Embryonic Stem Cells", Cell, May 30, 2003, vol. 113, No. 5, pp. 643-655.
Chen et al., "Enhanced Tumorigenesis in p53 Knockout Mice Exposed in Utero to High-Dose Vitamin E", Carcinogenesis, 2006, vol. 27, No. 7, pp. 1358-1368.
Chen et al., "Mesenchymal Stem Cell Secretes Microparticles Enriched in Pre-MicroRNAs", Nucleic Acids Research, 2010, vol. 38, No. 1, pp. 215-224.
Chen et al., "Reduced Tumorigenesis in p53 Knockout Mice Exposed in Utero to Low-Dose Vitamin E", Cancer, Apr. 1, 2009, vol. 115, pp. 1563-1575.
Chen et al., "The Role of Notch 1 Activation in Cardiosphere Derived Cell Differentiation", Stem Cells and Development, 2012, pp. 2122-2129, vol. 21, No. 12.
Chen et al., "Vascular Endothelial Growth Factor Promotes Cardiomyocyte Differentiation of Embryonic Stem Cells", American Journal of Physiology—Heart and Circulatory Physiology, Oct. 2006, vol. 291, No. 4, pp. H1653-H1658.

(56) References Cited

OTHER PUBLICATIONS

Cheng et al., "Functional Performance of Human Cardiosphere-Derived Cells Delivered in an in situ Polymerizable Hyaluronan-Gelatin Hydrogel", Biomaterials, 2012, pp. 8.
Cheng et al., "Magnetic Targeting Enhances Engraftment and Functional Benefit of Iron-Labeled Cardiosphere-Derived Cells in Myocardial Infarction", Circulation Research, 2010, pp. 1570-1581, vol. 106.
Cheng et al., "Relative Roles of CD90 and c-Kit to the Regenerative Efficacy of Cardiosphere-Derived Cells in Humans and in a Mouse Mode of Myocardial Infarction", Journal of the American Heart Association, Oct. 9, 2014, pp. 1-10, vol. 3, No. 5.
Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 2012, vol. 33, pp. 2872-2879.
Chimenti et al., "Abstract 3182: Paracrine Contribution versus Direct Regeneration in Cardiosphere-Derived Cell Therapy for Acute Myocardial Infarction", Circulation, 2009, vol. 120, p. S756.
Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.
Chlopčíková et al., "Neonatal Rat Cardiomyocytes—A Model for the Study of Morphological Biochemical and Electrophysiological Characteristics of the Heart", Biomedical Papers, 2001, vol. 145, No. 2, pp. 49-55.
Cho et al., "Secondary Sphere Formation Enhances the Functionality of Cardiac Progenitor Cells", Molecular Therapy, Sep. 2012, vol. 20, No. 9, pp. 1750-1766.
Christman et al., "Biomaterials for the Treatment of Myocardial Infarction", Journal of the American College Of Cardiology, 2006, vol. 48, No. 5, pp. 907-913.
Conkright et al., "A Gene Encoding an Intestinal-Enriched Member of the Krüppel-Like Factor Family Expressed in Intestinal Epithelia Cells", Nucleic Acids Research, 1999, vol. 27, No. 5, pp. 1263-1270.
Crisostomo et al., "Embryonic Stem Cells Attenuate Myocardial Dysfunction and Inflammation After Surgical Global Ischemia via Paracrine Actions", American Journal of Physiology—Heart and Circulatory Physiology, 2008, vol. 295, pp. H1726-H1735.
Csete, Marie, "Oxygen in the Cultivation of Stem Cells", Annals New York Academy of Sciences, 2005, vol. 1049, pp. 1-8.
"Culture Media Database", EGM-2 (Endothelial Growth Medium 2)—ID 63, downloaded from http://bio.lonza.com/3018.html#ext-comp-1003:tab_63:chanqe, printed on Jan. 14, 2013, p. 1.
Davis et al., "Human Cardiospheres are a Source of Stem Cells with Cardiomyogenic Potential", Stem Cells, 2010, vol. 28, No. 5, pp. 903-904.
Davis et al., "Isolation and Expansion of Functionally-Competent Cardiac Progenitor Cells Directly from Heart Biopsies", Journal of Molecular and Cellular Cardiology, Aug. 2010, vol. 49, No. 2, pp. 312-321.
Davis et al., "Validation of the Cardiosphere Method to Culture Cardiac Progenitor Cells from Myocardial Tissue", PLoS One, 2009, vol. 4, No. 9, e7195, pp. 1-8.
De Bakker et al., "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
De Pomerai et al., "Influence of Serum Factors on the Prevalence of 'Normal' and 'Foreign' Differentiation Pathways in the Cultures of Chick Embryo Neuroretinal Cells", Journal of Embryology and Experimental Morphology, 1981, pp. 291-308, vol. 62.
Deal et al., "Molecular Physiology of Cardiac Potassium Channels", Physiological Reviews, Jan. 1996, vol. 76, No. 1, pp. 49-67.
Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), Apr. 13, 2004, vol. 101, No. 15, pp. 5622-5627.
Deregibus et al., "Endothelial Progenitor Cell-Derived Microvesicles Activate an Angiogenic Program in Endothelial Cells by a Horizontal Transfer of mRNA", Blood, Oct. 1, 2007, vol. 110, No. 7, pp. 2440-2448.
Derossi et al., "The Third Helix of the Antennapedia Homeodomain Translocates through Biological Membranes", The Journal of Biological Chemistry, Apr. 8, 1994, vol. 269, No. 14, pp. 10444-10450.
Di Meglio et al., "In Vitro Cultured Progenitors and Precursors of Cardiac Cell Lineages from Human Normal and Post-Ischemic Hearts", European Journal of Histochemistry, Oct.-Dec. 2007, vol. 51, No. 4, pp. 275-285.
Dispersyn et al., "Adult Rabbit Cardiomyocytes Undergo Hibernation-Like Dedifferentiation When Co-Cultured with Cardiac Fibroblasts", Cardiovascular Research, 2001, vol. 51, pp. 230-240.
Dispersyn et al., "Dissociation of Cardiomyocyte Apoptosis and Dedifferentiation in Infarct Border Zones", European Heart Journal, 2002, vol. 23, pp. 849-857.
Dixon et al., "Quantitative Analysis of Potassium Channel mRNA Expression in Atrial and Ventricular Muscle of Rats", Circulation Research, Aug. 1994, vol. 75, No. 2, pp. 252-260.
Dixon et al., "Role of the Kv4.3 $K^+$ Channel in Ventricular Muscle", Circulation Research, 1996, vol. 79, pp. 659-668.
Djokic et al., "Post-Transplant Lymphoproliferative Disorder Subtypes Correlate with Different Recurring Chromosomal Abnormalities", Genes, Chromosomes & Cancer, 2006, vol. 45, pp. 313-318.
Donahue et al., "Ultrarapid, Highly Efficient Viral Gene Transfer to the Heart", Proceedings of the National Academy of Sciences of the United States of America, Apr. 1997, vol. 94, pp. 4664-4668.
Dong et al., "Islet Cell and Extrapancreatic Expression of the LIM Domain Homeobox Gene is/-1", Molecular Endocrinology, 1991, vol. 5, No. 11, pp. 1633-1641.
Drakos et al., "Impact of Mechanical Unloading on Microvasculature and Associated Central Remodeling Features of the Failing Human Heart", Journal of the American College of Cardiology, Jul. 27, 2010, vol. 56, No. 5, pp. 382-391.
Driesen et al., "Structural Adaptation in Adult Rabbit Ventricular Myocytes: Influence of Dynamic Physical Interaction With Fibroblasts", Cell Biochemistry and Biophysics, 2006, vol. 44: 119-128.
Driesen et al., "Structural Remodeling of Cardiomyocytes in the Border Zone of Infarcted Rabbit Heart", Molecular and Cellular Biochemistry, 2007, pp. 225-232, vol. 302.
Duff et al., "CD105 is Important for Angiogenesis: Evidence and Potential Applications," FASEB Journal, Jun. 2003, vol. 17, No. 9, pp. 984-992.
Eguchi, Masakatsu, "Recent Advances in Selective Opioid Receptor Agonists and Antagonists", Medicinal Research Reviews, 2004, vol. 24, No. 2, pp. 182-212.
Elliott et al., "Intercellular Trafficking and Protein Delivery by a Herpesvirus Structural Protein", Cell, Jan. 24, 1997, vol. 88, pp. 223-233.
Elliott et al., "Intercellular Trafficking of VP22-GFP Fusion Proteins", Gene Therapy, 1999, vol. 6, pp. 149-151.
Engel et al. "p38 MAP Kinase Inhibition Enables Proliferation of Adult Mammalian Cardiomyocytes", Genes & Development, May 2005, vol. 19, No. 10, pp. 1175-1187.
Engel et al., FGF1/p38 MAP Kinase Inhibitor Therapy Induces Cardiomyocyte Mitosis, Reduces Scarring, and Rescues Function after Myocardial Infarction, Proceedings of the National Academy of Sciences of the United States of America (PNAS), Oct. 17, 2006, vol. 103, No. 42, pp. 15546-15551.
Eppenberger-Eberhardt et al., "Reexpression of α-Smooth Muscle Acting Isoform in Cultured Adult Rat Cardiomyocytes", Developmental Biology, Jun. 1990, vol. 139, No. 2, pp. 269-278.
Eschenhagen et al., "Engineering Myocardial Tissue", Circulation Research, 2005, vol. 97, pp. 1220-1231.
Falck et al., "Conserved Modes of Recruitment of ATM, ATR and DNA-PKcs to Sites of DNA Damage", Nature, Mar. 31, 2005, vol. 434, pp. 605-611.

(56) References Cited

OTHER PUBLICATIONS

Fehrer et al., "Reduced Oxygen Tension Attenuates Differentiation Capacity of Human Mesenchymal Stem Cells and Prolongs their Lifespan", Aging Cell, 2007, vol. 6, pp. 745-757.

Fiset et al., Shal-Type Channels Contribute to the $Ca^{2+}$ -Independent Transient Outward $K^+$ Current in Rat Ventricle, Journal of Physiology, 1997, vol. 500, No. 1, pp. 51-64.

Foreman et al., "Reactive Oxygen Species Produced by NADPH Oxidase Regulate Plant Cell Growth", Nature, Mar. 27, 2003, vol. 422, pp. 442-446.

Frankel et al., "Cellular Uptake of the Tat Protein from Human Immunodeficiency Virus", Cell, vol. 55, Dec. 23, 1988, pp. 1189-1193.

Freyman et al., "A Quantitative, Randomized Study Evaluating Three Methods of Mesenchymal Stem Cell Delivery Following Myocardial Infarction", European Heart Journal, 2006, vol. 27, pp. 1114-1122.

Furlani et al., "A Transformed Cell Population Derived From Cultured Mesenchymal Stem Cells Has no Functional Effect After Transplantation Into the Injured Heart", Cell Transplantation, 2009, vol. 18, pp. 319-331.

Gallet et al., "Intracoronary Delivery of Self-Assembling Heart-Derived Microtissues (Cardiospheres) for Prevention of Adverse Remodeling in a Pig Model of Convalescent Myocardial Infarction", http://circinterventions.ahajournals.org, Dec. 8, 2015, pp. 21.

Galli et al., "Neural Stem Cells: An Overview", Circulation Research, 2003, vol. 92, No. 6, pp. 598-608.

Gatti et al., Microvesicles Derived from Human Adult Mesenchymal Stem Cells Protect Against Ischaemia-Reperfusion-Induced Acute and Chronic Kidney Injury, Nephrology Dialysis Transplantation, 2011, vol. 26, No. 5, pp. 1474-1483.

George et al., "Echocardiographic Assessment of Flow Across Continuous-Flow Ventricular Assist Devices at Low Speeds", The Journal of Heart and Lung Transplantation, Nov. 2010, vol. 29, No. 11, pp. 1245-1252.

Gibco, "Insulin-Transferrin-Selenium", Product Sheet, 2014.

Gibco, "Insulin-Transferrin-Selenium: 100X (For General Tissue Culture Applications)", Product Sheet, Form No. 2672, Jun. 2001, p. 1.

Gidh-Jain et al., Differential Expression of Voltage-Gated $K^+$ Channel Genes in Left Ventricular Remodeled Myocardium After Experimental Myocardial Infarction, Circulation Research, 1996, vol. 79, pp. 669-675.

Glover et al., "Reduction of Infarct Size and Postischemic Inflammation from ATL-146e, a Highly Selective Adenosine $A_{2A}$ Receptor Agonist in Reperfused Canine Myocardium", American Journal of Physiology—Heart and Circulatory Physiology, Apr. 2005, vol. 288, No. 4, pp. H1851-H1858.

Gómez-Márquez et al., "Thymosin-β4 Gene: Preliminary Characterization and Expression in Tissues, Thymic Cells, and Lymphocytes", The Journal of Immunology, Oct. 15, 1989, vol. 143, No. 8, pp. 2740-2744.

Good et al., "ß-Amyloid Peptide Blocks the Fast-Inactivating $K^+$ Current in Rat Hippocampal Neurons", Biophysical Journal, Jan. 1996, vol. 70, pp. 296-304.

Goumans et al., "TGF-β1 Induces Efficient Differentiation of Human Cardiomyocyte Progenitor Cells into Functional Cardiomyocytes In Vitro", Stem Cell Research, 2008, vol. 1, pp. 138-149.

Grayson et al. "Hypoxia Enhances Proliferation and Tissue Formation of Human Mesenchymal Stem Cells", Biochemical and Biophysical Research Communications, 2007, vol. 358, pp. 948-953.

Green et al., "Autonomous Functional Domains of Chemically Synthesized Human Immunodeficiency Virus Tat Trans-Activator Protein", Dec. 23, 1988, Cell, vol. 55, pp. 1179-1188.

Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.

Grigorian-Shamagian et al., "Harnessing the Heart's Resistance to Malignant Tumors; Cardiac-Derived Extracellular Vesicles Decrease Fibrosarcoma Growth and Leukemia-Related Mortality in Rodents", Oncotarget, 2017, vol. 8, No. 59, pp. 99624-99636.

Grossman et al., "Contractile State of the Left Ventricle in Man as Evaluated from End-Systolic Pressure-Volume Relations", Circulation, vol. 56, No. 5, Nov. 1977, pp. 845-852.

Gu, Yiping, "Bispecific Antibody Targeted Stem Cell Therapy for Myocardial Repair", Dissertation, University of California San Francisco and University of California Berkeley, 2008, pp. 94.

Gubbay et al., "A Gene Mapping to the Sex-Determining Region of the Mouse Y Chromosome is a Member of a Novel Family of Embryonically Expressed Genes", Nature, Jul. 19, 1990, vol. 346, pp. 245-250.

Hacien-Bey-Abina et al., "LMO2-Associated Clonal T Cell Proliferation in Two Patients after Gene Therapy for SCID-X1", Science, Oct. 17, 2003, vol. 302, pp. 415-419 with Erratum in 1 page.

Hagège, MD, PhD, et al., "Skeletal Myoblast Transplantation in Ischemic Heart Failure: Long-Term Follow-Up of the First Phase I Cohort of Patients", Circulation, Jul. 4, 2006, vol. 114, No. 1, pp. 1108-1113.

Haider et al., "Bone Marrow Stem Cell Transplantation for Cardiac Repair", American Journal of Physiology—Heart and Circulatory Physiology, 2005, H2557-H2567, vol. 288.

Hainsworth et al., "The Nitrone Disodium 2,4-Sulphophenyl-N-Tert-Butylnitrone is Without Cytoprotective Effect on Sodium Nitroprusside-Induced Cell Death in N1E-115 Neuroblastoma Cells in vitro", Journal of Cerebral Blood Flow & Metabolism, 2008, vol. 28, pp. 24-28.

Haj-Yahia et al., "Limited Surgical Approach for Explanting the HeartMate II Left Ventricular Assist Device after Myocardial Recovery", The Journal of Thoracic and Cardiovascular Surgery, 2008, vol. 135, No. 2, pp. 453-454.

Harvey, "Molecular Determinants of Cardiac Development and Congenital Disease," Mouse Development, Patterning, Morphogenesis, and Organogensis, 2002, pp. 331-370, Chapter 16.

Heng et al., "Incorporating Protein Transduction Domains (PTD) Within Recombinant 'Fusion' Transcription Factors. A Novel Strategy for Directing Stem Cell Differentiation?" Biomedicine and Pharmacotherapy, Apr. 1, 2005, vol. 59, No. 3, pp. 132-134.

Hergenreider et al., "Atheroprotective Communication Between Endothelial Cells and Smooth Muscle Cells Through miRNAs", Nature Cell Biology, Mar. 2012, vol. 14, No. 3, pp. 249-256.

Herrera et al., "Human Liver Stem Cell-Derived Microvesicles Accelerate Hepatic Regeneration in Hepatectomized Rats", Journal of Cellular and Molecular Medicine, 2010, vol. 14, No. 6B, pp. 1605-1618.

Hierlihy et al., "The Post-Natal Heart Contains a Myocardial Stem Cell Population", FEBS Letters, 2002, vol. 530, No. 1-3, pp. 239-243.

Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.

Hochedlinger et al., "Nuclear Reprogramming and Pluripotency", Nature, Jun. 29, 2006, vol. 441, pp. 1061-1067.

Hu et al., "MicroRNA-210 as a Novel Therapy for Treatment of Ischemic Heart Disease", Circulation, Sep. 14, 2010, vol. 122, Supplement 11, S124-S131, pp. 17.

Hullinger et al., Inhibition of miR-15 Protects Against Cardiac Ischemic Injury, Circulation Research, Jan. 6, 2012, vol. 110, No. 1, pp. 71-81.

Ibrahim et al., "Exosomes as Critical Agents of Cardiac Regeneration Triggered by Cell Therapy", Stem Cell Reports, May 6, 2014, vol. 2, pp. 606-619.

Ibrahim et al., "Exosomes: Fundamental Biology and Roles in Cardiovascular Physiology", Annual Review of Physiology, 2016, vol. 78, pp. 67-83.

Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.

(56) References Cited

OTHER PUBLICATIONS

Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
International Preliminary Report on Patentability and Written Opinion received in PCT/US2017/035846, dated Dec. 13, 2018 in 7 pages.
International Search Report and Written Opinion received in PCT Application No. PCT/US2017/035846, dated Sep. 5, 2017 in 8 pages.
Ivanovic, Zoran, "Hypoxia or In Situ Normoxia: The Stem Cell Paradigm", Journal of Cellular Physiology, 2009, vol. 219, pp. 271-275.
Jackson et al., "Regeneration of Ischemic Cardiac Muscle and Vascular Endothelium by Adult Stem Cells", The Journal of Clinical Investigation, Jun. 2001, pp. 1395-1402, vol. 107, No. 11.
Jayawardena et al., "MicroRNA-Mediated In Vitro and In Vivo Direct Reprogramming of Cardiac Fibroblasts to Cardiomyocytes, Circulation Research, 2012, vol. 110, No. 11, pp. 1465-1473.
Johnston, MD, et al., "Engraftment, Differentiation, and Functional Benefits of Autologous Cardiosphere-Derived Cells in Porcine Ischemic Cardiomyopathy", Circulation, Sep. 22, 2009, vol. 120, pp. 1075-1083.
Jutkiewicz, Emily, The Antidepressant-Like Effects of Delta-Opioid Receptor Agonists, Molecular Interventions, 2006, vol. No. 3, pp. 162-169.
Kääb et al., "Ionic Mechanism of Action Potential Prolongation in Ventricular Myocytes From Dogs With Pacing-Induced Heart Failure", Circulation Research, 1996, vol. 78, No. 2, pp. 262-273.
Kamdar et al., "Dystrophin-Deficient Cardiomyopathy", Journal of the American College of Cardiology, 2016, vol. 67, No. 21, pp. 2533-2546.
Karlsson et al., "Insulin Gene Enhancer Binding Protein Isl-1 is a Member of a Novel Class of Proteins Containing Both a Homeo-and a Cys-His Domain", Nature, Apr. 26, 1990, vol. 344, pp. 879-882.
Karoubi et al., "Single-Cell Hydrogel Encapsulation for Enhanced Survival of Human Marrow Stromal Cells", Biomaterials, 2009, vol. 30, pp. 5445-5455.
Kawaguchi et al., "Cell Shape and Cardiosphere Differentiation: A Revelation by Proteomic Profiling", Hindawi Publishing Corporation, Biochemistry Research International, vol. 2013, Article ID 730874, pp. 1-9.
Kim et al., "Generation of Human Induced Pluripotent Stem Cells by Direct Delivery of Reprogramming Proteins", Cell Stem Cell, Jun. 5, 2009, vol. 4, No. 6, pp. 472-476.
Kisselbach et al., "CD90 Expression on Human Primary Cells and Elimination of Contaminating Fibroblasts from Cell Cultures", Cytotechnology, 2009, pp. 31-44, vol. 59.
Kühn et al., "Periostin Induces Proliferation of Differentiated Cardiomyocytes and Promotes Cardiac Repair", Nature Medicine, Aug. 2007, vol. 13, No. 8, pp. 962-969.
Kutschka et al., "Collagen Matrices Enhance Survival of Transplanted Cardiomyoblasts and Contribute to Functional Improvement of Ischemic Rat Hearts", Circulation, Jul. 4, 2006, vol. 114, pp. 1167-1173.
Kwon et al., "Cellular Manipulation of Human Embryonic Stem Cells by TAT-PDX1 Protein Transduction," Molecular Therapy, Jul. 1, 2005, vol. 12, No. 1, pp. 28-32.
Kyrtatos et al., "Magnetic Tagging Increases Delivery of Circulating Progenitors in Vascular Injury", Journal of the American College of Cardiology: Cardiovascular Interventions, 2009, pp. 794-802, vol. 2, No. 8.
Laflamme et al., "Cardiomyocytes Derived from Human Embryonic Stem Cells in Pro-Survival Factors Enhance Function of Infarcted Rat Hearts", Nature Biotechnology, Sep. 2007, vol. 25, No. 9, pp. 1015-1024.
Lai et al., "Exosome Secreted by MSC Reduces Myocardial Ischemia/Reperfusion Injury", Stem Cell Research, 2010, vol. 4, pp. 214-222.
Landázuri et al., "Complexation of Retroviruses with Charged Polymers Enhances Gene Transfer by Increasing the Rate that Viruses are Delivered to Cells", The Journal of Gene Medicine, 2004, vol. 6, pp. 12, pp. 1304-1319.
Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, vol. 307, Sep. 2018, pp. 109-117.
Lavon et al., "Derivation of Euploid Human Embryonic Stem Cells from Aneuploid Embryos", Stem Cells, 2008, vol. 26, pp. 1874-1882.
Lee et al., "Antibody Targeting of Stem Cells to Infarcted Myocardium", Stem Cells: Translational and Clinical Research, 2007, pp. 712-717, vol. 25.
Lee et al., "Cardiac Gene Transfer by Intracoronary Infusion of Adenovirus Vector-Mediated Reporter Gene in the Transplanted Mouse Heart", The Journal of Thoracic and Cardiovascular Surgery, 1996, pp. 246-252, vol. 111.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Leferovich et al., "Heart Regeneration in Adult MRL Mice", Proceedings of the National Academy of Sciences of the United States of America (PNAS), Aug. 14, 2001, vol. 98, No. 17, pp. 9830-9835.
Leor, MD, et al., "Transplantation of Fetal Myocardial Tissue Into the Infarcted Myocardium of Rat", Circulation, Nov. 1, 1996, vol. 94, No. 9, II-332-II-336.
Levenberg at al., "Endothelial Cells Derived from Human Embryonic Stem Cells", Proceedings of the National Academy of Sciences of the United States of America (PNAS), Developmental Biology, Apr. 2, 2002, pp. 4391-4396, vol. 99, No. 7.
Levine et al., "Vitamin C Pharmacokinetics in Healthy Volunteers: Evidence for a Recommended Dietary Allowance", Proceedings of the National Academy of Sciences of the United States of America, Apr. 1996, vol. 93, pp. 3704-3709.
Li et al., "Cardiospheres Recapitulate a Niche-Like Microenvironment Rich in Sternness and Cell-Matrix Interactions, Rationalizing Their Enhanced Functional Potency for Myocardial Repair", Stem Cells: Translational and Clinical Research, 2010, pp. 2088-2098, vol. 28.
Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.
Li et al., "Expansion of Human Cardiac Stem Cells in Physiological Oxygen Improves Cell Production Efficiency and Potency for Myocardial Repair", Cardiovascular Research, Jul. 29, 2010, pp. 1-9.
Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions, Abstract 5173, Circulation Research, Dec. 4, 2009, vol. 105, No. 12, pp. e56-e62.
Li et al., "Molecular, Cellular, and Functional Phenotypes of Human Cardiac Stem Cells Dependent Upon Monolayer Versus Three-Dimensional Culture Conditions", Circulation Research, Dec. 4, 2009, Abs. 5173, vol. 105, No. 12, p. e58.
Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, May 4, 2010, vol. 28, pp. 1178-1185.
Li, MD, PhD et al., "Imaging Survival and Function of Transplanted Cardiac Resident Stem Cells", Journal of the American College of Cardiology, Apr. 7, 2009, vol. 53, No. 14, pp. 1229-1240.
Liao et al., "Enhanced Efficiency of Generating Induced Pluripotent Stem (iPS) Cells from Human Somatic Cells by a Combination of Six Transcription Factors", Cell Research, 2008, vol. 18, pp. 600-603.

(56) References Cited

OTHER PUBLICATIONS

Lin et al., "Accelerated Growth and Prolonged Lifespan of Adipose Tissue-Derived Human Mesenchymal Stem Cells in a Medium Using Reduced Calcium and Antioxidants", Stem Cells and Development, 2005, vol. 14, pp. 92-102.
Lindsay, Mark A., "Peptide-Mediated Cell Delivery: Application in Protein Target Validation", Current Opinion in Pharmacology, 2002, vol. 2, pp. 587-594.
Lindsley et al., "The PI3K/Akt Pathway: Recent Progress in the Development of ATP-Competitive and Allosteric Akt Kinase Inhibitors", Current Cancer Drug Targets, 2008, vol. 8, pp. 7-18.
Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 2007, vol. 50, No. 18, pp. 1761-1767.
Liu et al. "Autologous Stem Cell Transplantation for Myocardial Repair", American Journal of Physiology, Heart and Circulatory Physiology, 2004, pp. H501-H511, vol. 287.
Liu et al., "Osteochondral Defect Repair with Autologous Bone Marrow-Derived Mesenchymal Stem Cells in an Injectable, In Situ, Cross-Linked Synthetic Extracellular Matrix", Tissue Engineering, 2006, pp. 3405-3416, vol. 12, No. 12.
Lowry et al., "Generation of Human Induced Pluripotent Stem Cells from Dermal Fibroblasts", Proceedings of the National Academy of Sciences of the United States of America (PNAS), Feb. 26, 2008, vol. 105, No. 8, pp. 2883-2888.
Lum et al., "The New Face of Bispecific Antibodies: Targeting Cancer and Much More", Experimental Hematology, 2006, pp. 1-6, vol. 34.
Lyngbaek et al., "Cardiac Regeneration by Resident Stem and Progenitor Cells in the Adult Heart", Basic Research in Cardiology, 2007, vol. 102, pp. 101-114.
Maitra et al., "Genomic Alterations in Cultured Human Embryonic Stem Cells, Nature Genetics, Oct. 2005, vol. 37, No. 10, pp. 1099-1103.
Maletic-Savatic et al., "Differential Spatiotemporal Expression of $K^+$ Channel Polypeptides in Rat Hippocampal Neurons Developing In Situ and In Vitro", The Journal of Neuroscience, May 1995, vol. 15, No. 5, pp. 3840-3851.
Mangi et al., "Mesenchymal Stem Cells Modified with Akt Prevent Remodeling and Restore Performance of Infarcted Hearts," Nature Medicine, Sep. 2003, vol. 9, No. 9, pp. 1195-1201.
Marbán, Eduardo, "Big Cells, Little Cells, Stem Cells: Agents of Cardiac Plasticity", Circulation Research, 2007, vol. 100, No. 4, pp. 445-446.
Marshall et al., "The Jellyfish Green Fluorescent Protein: A New Tool for Studying Ion Channel Express and Function", Neuron, Feb. 1995, vol. 14, pp. 211-215.
Martens et al., "Percutaneous Cell Delivery Into the Heart Using Hydrogels Polymerizing In Situ", Cell Transplantation, 2009, vol. 18, No. 3, pp. 297-304.
Matsuura et al., "Adult Cardiac Sca-1-positive Cells Differentiate into Beating Cardiomyocytes", The Journal of Biological Chemistry, Mar. 19, 2004, vol. 279, No. 12, pp. 11384-11391.
McGann et al., "Mammalian Myotube Dedifferentiation Induced by Newt Regeneration Extract", Proceedings of the National Academy of Sciences of the United States of America (PNAS), Nov. 20, 2001, vol. 98, No. 24, pp. 13699-13704.
Mehmel et al., "The Linearity of the End-Systolic Pressure-Volume Relationship in Man and its Sensitivity for Assessment of Left Ventricular Function", Circulation, 1981, vol. 63, pp. 1216-1222.
Messina et al., "Isolation and Expansion of Adult Cardiac Stem Cells from Human and Murine Heart", Oct. 29, 2004, Circulation Research, Cellular Biology, American Heart Association, vol. 95, pp. 911-921.
Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.
Miller III, et al., Meta-Analysis: High-Dosage Vitamin E Supplementation May Increase All-Cause Mortality, Annals of Internal Medicine, 2005, vol. 142, pp. 37-46.
Miltenyi et al., "High Gradient Magnetic Cell Separation With MACS[1]", Cytometry, 1990, pp. 231-238, vol. 11.
Mitsui et al., "The Homeoprotein Nanog is Required for Maintenance of Pluripotency in Mouse Epiblast and ES Cells", Cell, May 30, 2003, vol. 113, No. 5, pp. 631-642.
Miyazono et al. "Latent High Molecular Weight Complex of Transforming Growth Factor β1", May 5, 1988, vol. 263, No. 13, pp. 6407-6415.
Montessuit et al., "Regulation of Glucose Transporter Expression in Cardiac Myocytes: p38 MAPK is a Strong Inducer of GLUT4", Cardiovascular Research, Oct. 1, 2004, vol. 64, No. 1, pp. 94-104.
Montessuit et al., "Retinoic Acids Increase Expression of GLUT4 in Dedifferentiated and Hypertrophied Cardiac Myocytes", Basic Research in Cardiology, Jan. 1, 2006, vol. 101, No. 1, pp. 27-35.
Moss et al., "Conservation of the Heterochronic Regulator Lin-28, its Developmental Expression and MicroRNA Complementary Sites", Developmental Biology, 2003, vol. 258, No. 2, pp. 432-442.
Moss, M.D., et al., Prophylactic Implantation of a Defibrillator in Patients with Myocardial Infarction and Reduced Ejection Fraction, The New England Journal of Medicine, Mar. 21, 2002, vol. 346, No. 12, pp. 877-883.
Murata et al., "C4d Deposition and Cellular Infiltrates as Markers of Acute Rejection in Rat Models of Orthotopic Lung Transplantation", Transplantation, Jul. 15, 2008, vol. 86, No. 1, pp. 123-129.
Nadal-Ginard et al., "Myocyte Death, Growth, and Regeneration in Cardiac Hypertrophy and Failure", Circulation Research, 2003, vol. 92, pp. 139-150.
Nadal-Ginard et al., "A Matter of Life and Death: Cardiac Myocyte Apoptosis and Regeneration", Journal of Clinical Investigation, May 2003, vol. 111, No. 10, pp. 1457-1459.
Naka et al., "Regulation of Reactive Oxygen Species and Genomic Stability in Hematopoietic Stem Cells", Antioxidants & Redox Signaling, 2008, vol. 10, No. 11, pp. 1883-1894.
Nakagawa et al., "Generation of Induced Pluripotent Stem Cells without Myc from Mouse and Human Fibroblasts", Nature Biotechnology, Jan. 2008, vol. 26, No. 1, pp. 101-106.
Nakasa et al., "Acceleration of Muscle Regeneration by Local Injection of Muscle-Specific MicroRNAs in Rat Skeletal Muscle Injury Model", Journal of Cellular and Molecular Medicine, 2010, vol. 14, No. 10, pp. 2495-2505.
Nelson et al., "CXCR4[+]/FLK-1[+] Biomarkers Select a Cardiopoietic Lineage from Embryonic Stem Cells", Stem Cells, 2008, vol. 26, pp. 1464-1473.
Nelson, MD, PhD et al., "Repair of Acute Myocardial Infarction with iPS Induced by Human Sternness Factors", Circulation, Aug. 4, 2009, vol. 120, No. 5, pp. 408-416.
Niethammer et al., "A Tissue-Scale Gradient of Hydrogen Peroxide Mediates Rapid Wound Detection in Zebrafish", Nature, Jun. 18, 2009, vol. 459, pp. 996-999.
Noguchi et al., "Protein Transduction Technology: A Novel Therapeutic Perspective", Acta Medica Okayama, 2006, vol. 60, No. 1, pp. 1-11.
Nussbaum et al., "Transplantation of Undifferentiated Murine Embryonic Stem Cells in the Heart: Teratoma Formation and Immune Response", The FASEB Journal, Research Communication, May 2007, vol. 21, No. 7, pp. 1345-1357.
Odelberg et al., "Dedifferentiation of Mammalian Myotubes Induced by msx1", Cell, Dec. 22, 2000, vol. 103, No. 7, pp. 1099-1109.
Odelberg, Shannon J., Inducing Cellular Dedifferentiation: A Potential Method for Enhancing Endogenous Regeneration in Mammals., Seminars in Cell & Developmental Biology, 2002, vol. 13, No. 5, pp. 335-343.
Offord et al., "Photoprotective Potential of Lycopene, -Carotene, Vitamin E, Vitamin C and Carnosic in UVA-Irradiated Human Skin Fibroblasts", Free Radical Biology & Medicine, 2002, vol. 32, No. 12, pp. 1293-1303.
Oh et al., "Cardiac Muscle Plasticity in Adult and Embryo by Heart-Derived Progenitor Cells", Annals of the New York Academy of Sciences, 2004, vol. 1015, pp. 182-189.

(56) References Cited

OTHER PUBLICATIONS

Oh et al., "Cardiac Progenitor Cells from Adult Myocardium: Homing, Differentiation, and Fusion After Infarction", Proceedings of the National Academy of Sciences of the United States of America (PNAS), Oct. 14, 2003, p. 12313-12318, vol. 100, No. 21.
Okita et al., Generation of Mouse Induced Pluripotent Stem Cells Without Viral Vectors, Nov. 7, 2008, Science, vol. 322, pp. 949-953.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, http://circ.ahajournals.org/content/132/Suppl_3/A13881.short.
Owusu-Ansah et al., "Reactive Oxygen Species Prime *Drosophila* Haematopoietic Progenitors for Differentiation", Nature, Sep. 24, 2009, vol. 461, pp. 537-541.
Park et al., "Reprogramming of Human Somatic Cells to Pluripotency with Defined Factors", Nature, Jan. 10, 2008, vol. 451, pp. 141-146.
Passier et al., "Origin and Use of Embryonic and Adult Stem Cells in Differentiation and Tissue Repair", Cardiovascular Research, 2003, vol. 58, No. 2, pp. 324-335.
Passier et al., "Stem-Cell-Based Therapy and Lessons from the Heart", May 15, 2008, Nature, vol. 453, pp. 322-329.
Payne, Anthony G., "Using Immunomagnetic Technology and Other Means to Facilitate Stem Cell Homing", Medical Hypotheses, 2004, pp. 718-720, vol. 62.
Peterson, MD, MPH, et al., "Risk Stratification After Myocardial Infarction", Annals of Internal Medicine, 1997, vol. 126, No. 7, pp. 561-582.
Pike et al., "Heparin-Regulated Release of Growth Factors In Vitro and Angiogenic Response In Vivo to Implanted Hyaluronan Hydrogels Containing VEGF and bFGF," Biomaterials, 2006, vol. 27, pp. 5242-5241.
Piper et al. "Determinants of Cardiomyocyte Development in Long-Term Primary Culture", Journal of Molecular and Cellular Cardiology, 1988, vol. 20, pp. 825-835.
Plotnikov et al., "Biological Pacemaker Implanted in Canine Left Bundle Branch Provides Ventricular Escape Rhythms that Have Physiologically Acceptable Rates", Circulation, 2004, vol. 109, pp. 506-512.
Potapova et al., "Enhanced Recovery of Mechanical Function in the Canine Heart by Seeding an Extracellular Matrix Patch with Mesenchymal Stem Cells Committed to a Cardiac Lineage", American Journal of Physiology—Heart and Circulatory Physiology, 2008, vol. 295, pp. H2257-H2263.
Prestwich et al., "The Translational Imperative: Making Cell Therapy Simple and Effective", Acta Biomaterialia, 2012, vol. 8, pp. 4200-4207.
Prunier et al., "Delayed Erythropoietin Therapy Reduces Post-MI Cardiac Remodeling Only at a Dose that Mobilizes Endothelial Progenitor Cells", American Journal of Physiology—Heart and Circulatory Physiology, 2007, vol. 292, pp. H522-H529.
Puceat, Michel, "Role of Rac-GTPase and Reactive Oxygen Species in Cardiac Differentiation of Stem Cell", Antioxidants & Redox Signaling, 2005, vol. 7, No. 11 & 12, pp. 1435-1439.
Qin et al., "ATM-Mediated Transcriptional Elevation of Prion in Response to Copper-Induced Oxidative Stress", The Journal of Biological Chemistry, Feb. 13, 2009, vol. 284, No. 7, pp. 4582-4593.
Quaini et al., "Chimerism of the Transplanted Heart", The New England Journal of Medicine, Jan. 3, 2002, vol. 346, No. 1, pp. 5-15.
Quevedo et al., "Allogeneic Mesenchymal Stem Cells Restore Cardiac Function in Chronic Ischemic Cardiomyopathy via Trilineage Differentiating Capacity", Proceedings of the National Academy of Sciences of the United States of America (PNAS), Aug. 18, 2009, vol. 106, No. 33, pp. 14022-14027.
Rajasekaran et al., "Human αB-Crystallin Mutation Causes Oxido-Reductive Stress and Protein Aggregation Cardiomyopathy in Mice", Cell, 2007, vol. 130, No. 3, pp. 427-439.
Ranghino et al., "Endothelial Progenitor Cell-Derived Microvesicles Improve Neovascularization in a Murine Model of Hindlimb Ischemia", International Journal of Immunopathology and Pharmacology, 2012, vol. 25, No. 1, pp. 75-85.
Reiffel, James A., MD, FACC, "Ten Pearls for the Use of Antiarrhythmic Drugs for Atrial Fibrillation", Aug. 17, 2012, Retrieved from http://www.acc.org/latest-in-cardiology/articles/2014/07/18/15/12/ten-pearls-for-the-use-of-antiarrhythmic-drugs-for-atrial-fibrillation, pp. 17.
Riazifar et al., "Stem Cell Extracellular Vesicles: Extended Messages of Regeneration", Reviews in Advance, Oct. 19, 2016, vol. 14, No. 1, pp. 1-30.
Ribera, Angeles B., "Homogeneous Development of Electrical Excitability via Heterogeneous Ion Channel Expression", The Journal of Neuroscience, Feb. 1, 1996, vol. 16, No. 3, pp. 1123-1130.
Risebro et al., "Hand1 Regulates Cardiomyocyte Proliferation Versus Differentiation in the Developing Heart", Development, Nov. 2006, vol. 133, No. 22, pp. 4595-4606.
Rossi et al., "Deficiencies in DNA Damage Repair Limit the Function of Haematopoietic Stem Cells with Age", Nature, Jun. 7, 2007, vol. 447, pp. 725-729.
Rotwein et al., "Organization and Sequence of the Human Insulin-Like Growth Factor I Gene", The Journal of Biological Chemistry, Apr. 15, 1986, vol. 261, No. 11, pp. 4828-4832.
Rubio et al., "Spontaneous Human Adult Stem Cell Transformation", Cancer Research, 2005, vol. 65, pp. 3035-3039.
Rücker-Martin et al., "Dedifferentiation of Atrial Myocytes During Atrial Fibrillation: Role of Fibroblast Proliferation in Vitro", Cardiovascular Research, 2002, vol. 55, pp. 38-52.
Rudy, B. "Diversity and Ubiquity of K Channels", Neuroscience, 1988, vol. 25, No. 3, pp. 729-749.
Saito et al., "Cell Death Caused by Selenium Deficiency and Protective Effect of Antioxidants", The Journal of Biological Chemistry, Oct. 10, 2003, vol. 278, No. 41, pp. 39428-39434.
Sareen et al., Chromosome 7 and 19 Trisomy in Cultured Human Neural Progenitor Cells, PLoS One, Oct. 2009, vol. 4, No. 10, e7630, pp. 12.
Sasano et al., "Molecular Ablation of Ventricular Tachycardia after Myocardial Infarction", Natural Medicine, 2006, vol. 12, No. 11, pp. 1256-1258.
Sasano et al., "Ventricular Tachycardia from the Healed Myocardial Infarction Scar: Validation of an Animal Model and Utility of Gene Therapy", Heart Rhythm, Aug. 2009, vol. 6, No. 8, pp. S91-S97.
Scaria et al., "Host-Virus Genome Interactions: Marco Roles for MicroRNAs", Cellular Microbiology, 2007, vol. 9, No. 12, pp. 2784-2794.
Seifried et al., "A Review of the Interaction Among Dietary Antioxidants and Reactive Oxygen Species", Journal of Nutritional Biochemistry, 2007, vol. 18, pp. 567-579.
Sempere et al., Expression Profiling of Mammalian MicroRNAs Uncovers a Subset of Brain-Expressed MicroRNAs with Possible Roles in Murine and Human Neuronal Differentiation, Genome Biology, 2004, vol. 5, No. 3, pp. R13.1-R13.11.
Serôdio et al., "Cloning of a Novel Component of A-Type K+ Channels Operating at Subthreshold Potentials With Unique Expression in Heart and Brain", Journal of Neurophysiology, May 1996, vol. 75, No. 5, pp. 2174-2179.
Sert et al., "The Radioprotective Effect of Vitamins C, E and Vitamin E + Glutathione on the Small Intestine and the Thyroid Gland in Rats Irradiated with X-Rays", Turkish Journal of Medical Sciences, 2000, vol. 30, pp. 417-425.
Sesso, ScD, MPH, et al., "Vitamins E and C in the Prevention of Cardiovascular Disease in Men: The Physicians' Health Study II Randomized Controlled Trial", The Journal of the American Medical Association (JAMA), 2008, vol. 300, pp. 2123-2133.
Sharkey et al., "Stage-Specific Expression of Cytokine and Receptor Messenger Ribonucleic Acids in Human Preimplantation Embryos", 1995, Biology of Reproduction, 1995, vol. 53, pp. 955-962.
Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.

(56) References Cited

OTHER PUBLICATIONS

Shen et al. "Isolation of an Insulin-Like Growth Factor II cDNA with a Unique 5' Untranslated Region from Human Placenta", Mar. 1988, Proceedings of the National Academy of Sciences of the United States of America (PNAS), vol. 85, pp. 1947-1951.
Shenje et al., "Lineage Tracing of Cardiac Explant Derived Cells", PLoS One, Apr. 2008, vol. 3, No. 4, e1929, p. 10.
Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 2002, vol. 90, No. 3, pp. 1-10.
Shu et al., "Disulfide-Crosslinked Hyaluronan-Gelatin Hydrogel Films: A Covalent Mimic of the Extracellular Matrix for In Vitro Cell Growth", Biomaterials, 2003, vol. 24, pp. 3825-3834.
Sigma-Aldrich, Inc., "Nutrient Mixture F12 Ham Kaighn's Modification (F12K)", Product Description, May 2007, pp. 2.
Simpson et al., "A Tissue Engineering Approach to Progenitor Cell Delivery Results in Significant Cell Engraftment and Improved Myocardial Remodeling", Stem Cells, Sep. 2007, vol. 25, No. 9, pp. 2350-2357.
Singh, et al. "High-Dose α-Tocopherol Therapy Does Not Affect HDL Subtractions in Patients with Coronary Artery Disease on Statin Therapy", Clinical Chemistry, 2007, vol. 53, No. 3, pp. 525-528.
Singh, PhD, Jai Pal, "Enabling Technologies for Homing and Engraftment of Cells for Therapeutic Applications", JACC: Cardiovascular Interventions, Aug. 2009, vol. 2, No. 8, pp. 803-804.
Slaughter, MD et al., "Clinical Management of Continuous-Flow Left Ventricular Assist Devices in Advanced Heart Failure", The Journal of Heart and Lung Transplantation, Apr. 2010, vol. 29, No. 4S, pp. S1-39.
Smart et al., "De Novo Cardiomyocytes from Within the Activated Adult Heart After Injury", Nature, Jun. 30, 2011, vol. 474, pp. 640-646.
Smith et al., "Regenerative Potential of Cardiosphere-Derived Cells Expanded From Percutaneous Endomyocardial Biopsy Specimens", Circulation, Feb. 5, 2007, pp. 896-908, vol. 115.
Smith et al., "Unique Phenotype of Cardiospheres Derived from Human Endomyocardial Biopsies", Circulation, Supplement II, Oct. 25, 2005, pp. 2, vol. 112, No. 17.
Smith et al., "Unselected Human Cardiosphere-derived Cells are Functionally Superior to c-Kit- or CD90-Purified Cardiosphere-Derived Cells", Circulation, Supplement 2, Oct. 28, 2008, vol. 118, No. 17, p. 1.
Smith, PhD et al., "Stem Cells in the Heart: What's the Buzz all About? Part 1: Preclinical Considerations", Heart Rhythm, May 2008, vol. 5, No. 5, pp. 749-757.
Smith, PhD et al., "Stem Cells in the Heart: What's the Buzz all About? Part 2: Arrhythmic Risks and Clinical Studies", Heart Rhythm, Jun. 2008, vol. 5, No. 6, pp. 880-887.
Smits, Anke Maria, "Cell-Based Cardiac Repair", Thesis, Utrecht University, The Netherlands, 2009, pp. 180.
Srivastava et al., "Thymosin β4 Is Cardioprotective after Myocardial Infarction", Annals of the New York Academy of Sciences, Sep. 2007, vol. 1112, pp. 161-170. Abstract only.
Stańczyk, et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 2005, vol. 15, No. 1, pp. 131-137.
Stewart et al. "Revision of the 1990 Working Formulation for the Standardization of Nomenclature in the Diagnosis of Heart Rejection", The Journal of Heart and Lung Transplantation, 2005, vol. 24, No. 11, pp. 1710-1720.
Sussman, Mark A., "Myocardial Aging and Senescence: Where Have the Stem Cells Gone?" Annual Review of Physiology, 2004, vol. 66, pp. 29-48.
Takahashi et al., "Induction of Pluripotent Stem Cells from Adult Human Fibroblasts by Defined Factors," Cell, vol. 131, Nov. 30, 2007, pp. 861-872.
Takahashi et al., "Induction of Pluripotent Stem Cells from Fibroblast Cultures, Nature Protocols", 2007, vol. 2 No. 12, pp. 3081-3089.
Takeda et al., "Human Oct3 Gene Family: cDNA Sequences, Alternative Splicing, Gene Organization, Chromosomal Location, and Expression at Low Levels in Adult Tissues", Nucleic Acids Research, 199?, vol. 20, No. 17, pp. 4613-4620.
Takehara, MD, PhD, et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology, 2008, vol. 52, No. 23, pp. 1858-1865.
Takeshita et al. "Osteoblast-Specific Factor 2: Cloning of a Putative Bone Adhesion Protein with Homology with the Insect Protein Fasciclin I", Biochemical Journal, 1993, vol. 294, pp. 271-278.
Tateishi et al., "Clonally Amplified Cardiac Stem Cells are Regulated by Sca-1 Signaling for Efficient Cardiovascular Regeneration", Journal of Cell Science, 2007, vol. 120, No. 10, pp. 1791-1800.
Ten Dijke et al. "Identification of Another Member of the Transforming Growth Factor Type β Gene Family", Proceedings of the National Academy of Sciences of the United States of America (PNAS), 1988, vol. 85, pp. 4715-4719.
Terrovitis, MD, et al., "Assessment and Optimization of Cell Engraftment after Transplantation into the Heart", Circulation Research, Feb. 19, 2010, vol. 106, No. 3, pp. 479-494.
Terrovitis, MD, et al., "Noninvasive Quantification and Optimization of Acute Cell Retention by In Vivo Positron Emission Tomography after Intramyocardial Cardiac-Derived Stem Cell Delivery", Journal of the American College of Cardiology, Oct. 20, 2009, vol. 54, No. 17, pp. 1619-1626.
The Exosomes Derived from CDCs Experimental Data to Show that Unexpectedly Improved Characteristics are Exhibited, p. 1.
Tomita et al., "Cardiac Neural Crest Cells Contribute to the Dorman Multipotent Stem Cell in the Mammalian Heart", Journal of Cell Biology, Sep. 26, 2005, vol. 170, No. 7, pp. 1135-1148.
Torella et al., "Cardiac Stem Cell and Myocyte Aging, Heart Failure, and Insulin-Like Growth Factor-1 Overexpression", Circulation Research, 2004, vol. 95, pp. 514-524.
Torella et al., Resident Human Cardiac Stem Cells: Role in Cardiac Cellular Homeostasis and Potential for Myocardial Regeneration, Nature Clinical Practice: Cardiovascular Medicine, Mar. 2006, vol. 3, No. 1, pp. S8-S13.
Trevethick et al., "Treating Lung Inflammation with Agonists from the Adenosine A2A Receptor: Promises, Problems and Potential Solutions", British Journal of Pharmacology, 2008, vol. 155, pp. 463-474.
Tsagalou, MD, et al., "Depressed Coronary Flow Reserve is Associated with Decreased Myocardial Capillary Density in Patients with Heart Failure Due to Idiopathic Dilated Cardiomyopathy", Journal of the American College of Cardiology, 2008, vol. 52, No. 17, pp. 1391-1398.
Tseliou et al., "Abstract 15925: Newt Exosomes are Bioactive on Mammalian Heart, Enhancing Proliferation of Rat Cardiomyocytes and Improving Recovery After Myocardial Infarction", Circulation, Nov. 10, 2015, vol. 132, No. 3, pp. 2.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
Uemura et al., "Bone Marrow Stem Cells Prevent Left Ventricular Remodeling of Ischemic Heart Through Paracrine Signaling", Circulation Research, 2006, vol. 98, pp. 1414-1421.
Ueno et al., "Biphasic Role for Wnt/βCatenin Signaling in Cardiac Specification in Zebrafish and Embryonic Stem Cells", Proceedings of the National Academy of Sciences of the United States of America (PNAS), Jun. 5, 2007, vol. 104, No. 23, pp. 9685-9690.
Ulloa-Montoya et al., "Culture Systems for Pluripotent Stem Cells", Journal of Bioscience and Bioengineering, 2005, vol. 100, No. 1, pp. 12-27.

(56) References Cited

OTHER PUBLICATIONS

Urbanek et al., "Cardiac Stem Cells Possess Growth Factor Receptor Systems That After Activation Regenerate the Infarcted Myocardium, Improving Ventricular Function and Long-term Survival", Circulation Research, 2005, vol. 97, pp. 663-673.

Urbanek et al., "Intense Myocyte Formation from Cardiac Stem Cells in Human Cardiac Hypertrophy", Proceedings of the National Academy of Sciences of the United States of America (PNAS), Sep. 2, 2003, vol. 100, No. 18, pp. 10440-10445.

Urbanek et al., Myocardial Regeneration by Activation of Multipotent Cardiac Stem Cells in Ischemic Heart Failure, Proceedings of the National Academy of Sciences of the United States of America (PNAS), Jun. 14, 2005, vol. 102, No. 24, pp. 8692-8697.

Van Der Geest et al., "Quantification in Cardiac MRI", Journal of Magnetic Resonance Imaging, 1999, vol. 10, pp. 602-608.

Van Gent et al., "Chromosomal Stability and the DNA Double-Stranded Break Connection", Nature, Mar. 2001, vol. 2, pp. 196-206.

Van Vliet et al., "Progenitor Cells Isolated from the Human Heart: a Potential Cell Source for Regenerative Therapy", Netherlands Heart Journal, May 2008, vol. 16, No. 5, pp. 163-169.

Van Winkle et al., "Cardiogel: A Biosynthetic Extracellular Matrix for Cardiomyocyte Culture", In Vitro Cellular & Developmental Biology—Animal, Sep. 1996, vol. 21, pp. 478-485.

Vela et al., "Quest for the Cardiovascular Holy Grail: Mammalian Myocardial Regeneration", Cardiovascular Pathology, 2008, vol. 17, No. 1-5.

Ventura et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry, May 11, 2007, vol. 282, No. 19, pp. 14243-14252.

Von Harsdorf, R., "Can Cardiomyocytes Divide?" Heart, 2001, vol. 86, pp. 481-482.

Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.

Wagner, Richard, "The State of the Art in Antisense Research", Nature Medicine, Nov. 1995, vol. 1, No. 11, pp. 1116-1118.

Walder et al., "Up-Regulation of Neural Stem Cell Markers Suggests the Occurrence of Dedifferentiation in Regenerating Spinal Cord", Development Genes and Evolution, 2003, vol. 213, pp. 625-630.

Walravens et al., "Cardiosphere-Derived Cell and Mesenchymal Stem Cell Extracellular Vesicles Contain Distinct RNA Cargo", Scientific Program, ISEV2017, Dec. 2017, p. 173.

Wang et al. "The LIM Domain Homeobox Gene isl-1: Conversation of Human, Hamster, and Rat Complementary Deoxyribonucleic Acid Sequences and Expression in Cell Types of Non-neuroendocrine Lineage", Endocrinology, 1994, vol. 134, No. 3, pp. 1416-1422.

Wang et al., "Establishment of New Mouse Embryonic Stem Cell Lines is Improved by Physiological Glucose and Oxygen", Cloning and Stem Cells, 2006, vol. 8, No. 2, pp. 108-116.

Wernig el al., "c-Myc Is Dispensable for Direct Reprogramming of Mouse Fibroblasts", Cell Stem Cell, Jan. 2008, vol. 2, pp. 10-12.

White et al. "Intrinsic Cardiac Origin of Human Cardiosphere-Derived Cells", European Heart Journal, 2013, vol. 34, pp. 68-75.

Wilmut et al., "Viable Offspring Derived from Fetal and Adult Mammalian Cells", Nature, Feb. 27, 1997, vol. 385, pp. 810-813.

Wilson et al., "Bioluminescence Reporter Gene Imaging of Human Embryonic Stem Cell Survival, Proliferation, and Fate", Methods in Molecular Biology, 2009, vol. 574, pp. 87-103.

Wong et al., "Loss of the Y Chromosome: An Age-Related or Clonal Phenomenon in Acute Myelogenous Leukemia/Myelodysplastic Syndrome?" Archives of Pathology & Laboratory Medicine, Aug. 2008, vol. 132, pp. 1329-1332.

Wu et al., "Cellular Therapy and Myocardial Tissue Engineering: The Role of Adult Stem and Progenitor Cells", European Journal of Cardio-Thoracic Surgery, 2006, vol. 30, pp. 770-781.

Yamada et al., "Type V Collagen-Induced Oral Tolerance Plus Low-Dose Cyclosporine Prevents Rejection of MHC Class 1 and II Incompatible Lung Allografts", The Journal Immunology, Jul. 1, 2009, vol. 183, No. 1, pp. 237-245.

Yang et al., "Human Cardiovascular Progenitor Cells Develop from a $KDR^+$ Embryonic-Stem-Cell-Derived Population", Nature, May 22, 2008, vol. 453, pp. 524-528.

Yau MD et al., "Beneficial Effect of Autologous Cell Transplantation on Infarcted Heart Function: Comparison Between Bone Marrow Stromal Cells and Heart Cells", The Annals of Thoracic Surgery, 2003, vol. 75, No. 1, pp. 169.

Yee et al. "Allogeneic Cardiospheres Delivered via Percutaneous Transendocardial Injection Increase Viable Myocardium, Decrease Scar Size, and Attenuate Cardiac Dilation in Porcine Ischemic Cardiomyopathy", PLOS One, Dec. 2, 2014, pp. 1-29.

Yu et al., "Induced Pluripotent Stem Cell Lines Derived from Human Somatic cells," Science, Dec. 21, 2007, vol. 318, pp. 1917-1920.

Yu et al., "miR-221 and miR-222 Promote Schwann Cell Proliferation and Migration by Targeting LASS2 after Sciatic Nerve Injury", Journal of Cell Science, Jan. 25, 2012, vol. 125, No. 11, pp. 2675-2683.

Zammit et al., "The Skeletal Muscle Satellite Cell: Stem Cell or Son of Stem Cell?" Differentiation, 2001, vol. 68, pp. 193-204.

Zha et al., "Complementary Functions of ATM and H2AX in Development and Suppression of Genomic Instability", Proceedings of the National Academy of Sciences of the United States of America (PNAS), Jul. 8, 2008, vol. 105, No. 27, pp. 9302-9306.

Zhang et al., "Do Cardiac Stem Cells Arise from Cardiomyocyte Dedifferentiation?" Circulation Research, Nov. 2006, vol. 99, No. 11, p. 1278. Abstract only.

Zhao et al., "Targeting Human $CD34^+$ Hematopoietic Stem Cells With Anti-CD45 x Anti-Myosin Light-Chain Bispecific Antibody Preserves Cardiac Function in Myocardial Infarction", Journal of Applied Physiology, Feb. 21, 2008, pp. 1793-1800, vol. 104.

Zhou et al., "Down-Regulation of microRNA-26a Promotes Mouse Hepatocyte Proliferation During Liver Regeneration", PLoS ONE, Apr. 2012, vol. 7, No. 4, e33577, pp. 1-7.

Zhou et al., "Generation of Induced Pluripotent Stem Cells Using Recombinant Proteins", Cell Stem Cell, May 1, 2009, vol. 4, No. 5, pp. 381-384.

Zuo et al., Assessment of Myocardial Blood Perfusion Improved by CD151 in a Pig Myocardial Infarction Model, Acta Pharmacologica Sinica, Jan. 2009, vol. 30, No. 1, pp. 70-77.

Aminzadeh et al., "Exosome-Mediated Benefits of Cell Therapy in Mouse and Human Models of Duchenne Muscular Dystrophy", Stem Cell Reports, Mar. 13, 2018, vol. 10, No. 3, pp. 942-955.

Barile et al., "Human Cardiospheres as a Source of Multipotent Stem and Progenitor Cells", Hindawi Publishing Corporation, Stem Cells International, 2013, vol. 2013, pp. 10.

Cambier et al., "Y RNA Fragment in Extracellular Vesicles Confers Cardioprotection via Modulation of IL-10 Expression and Secretion", EMBO Molecular Medicine, 2017, vol. 9, No. 3, pp. 337-352.

Gallet et al., "Cardiosphere-Derived Cells Reverse Heart Failure With Preserved Ejection Fraction in Rats by Decreasing Fibrosis and Inflammation", JACC: Basic to Translational Science, Jan. 1, 2016, vol. 1, No. 1-2, pp. 14-28.

Haderk et al., "Tumor-Derived Exosomes Modulate PD-L1 Expression in Monocytes", Science Immunology, Jul. 28, 2017, vol. 2, No. 13, pp. 1-11.

Kaspar et al., "Current Understanding and Management of Dilated Cardiomyopathy in Duchenne and Becker Muscular Dystrophy", Journal of the American Association of Nurse Practitioners, May 2009, vol. 21, No. 5, pp. 241-249.

Kooijmans et al., "PEGylated and Targeted Extracellular Vesicles Display Enhanced Cell Specificity and Circulation Time", Journal of Controlled Release, 2016, vol. 224, pp. 77-85.

Li et al., "IL-6 Contributes to the Defective Osteogenesis of Bone Marrow Stromal Cells from the Vertebral Body of the Glucocorticoid-Induced Osteoporotic Mouse", PLoS ONE, Apr. 29, 2016, vol. 11, No. 4, pp. 19.

(56) References Cited

OTHER PUBLICATIONS

Makkar et al., "Intracoronary Cardiosphere-Derived Cells for Heart Regeneration After Myocardial Infarction (Caduceus): A Prospective, Randomised Phase 1 Trial", Lancet, Mar. 10, 2012, vol. 379, pp. 895-904.
Malliaras et al., "Intracoronary Cardiosphere-Derived Cells After Myocardial Infarction", Journal of the American College of Cardiology, 2014, vol. 63, No. 2, pp. 110-121.
Matsumura, Tsuyoshi, "Cardiaphal Association in Muscular Dystrophy", Nanbyo To Zaitaku Care (Intractable Diseases and Home Care), 2013, vol. 19, No. 8, pp. 55-57.
Naito-Matsui, Yuko, "Lack of Neu5Gc Expression Contributes to the Severity of Duchenne Muscular Dystrophy in Humans", Trends in Glycoscience and Glycotechnology, 2011, vol. 23, No. 132, pp. 194-196.
North et al., "The Intersection Between Aging and Cardiovascular Disease", Circulation Research, Apr. 13, 2012, pp. 1097-1108.
Stull et al., "Chronic Treatment With Allopurinol Boosts Survival and Cardiac Contractility in Murine Postischemic Cardiomyopathy", Circulation Research, Cellular Biology, Nov. 12, 2004, pp. 1005-1011.
Takeda et al., "Induced Pluripotant Stem(IPS) Cell-Based Cell Therapy for Duchenne Muscular Dystrophy", History of Medicine, Dec. 31, 2011, vol. 239, No. 14, pp. 1440-1444.
Shi et al., "3,3'-Diindolylmethane Stimulates Exosomal Wnt11 Autocrine Signaling in Human Umbilical Cord Mesenchymal Stem Cells to Enhance Wound Healing", Theranostics, 2017, vol. 7, No. 6, pp. 1674-1688.
Tsutsui, Hiroyuki, "Cardiomyopathy: Progress in Diagnosis and Treatments Topics: 1. New classification based on etiology of cardiomyopathy; 1. Classification of cardiomyopathy—its past and present status", The Japanese Society of Internal Medicine, Feb. 2014, vol. 103, No. 2, pp. 277-284.
Aminzadeh et al., "Mitigation of Skeletal Myopathy After Intramyocardial Injection of Cardiosphere-derived Cells in the Mdx Mouse Model of Duchenne Muscular DysLiophy", Circulation Research, Dec. 4, 2015, No. 22919, pp. e122-e127.
Gallet et al., "Exosomes Secreted by Cardiosphere-Derived Cells Reduce Scarring, Attenuate Adverse Remodeling, and Improve Function in Acute and Chronic Porcine Myocardial Infarction", European Heart Journal, Jan. 14, 201,7, vol. 38, pp. 201-211.
Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1, pp. 3.
Anastasiou-Nana et al., "Relative Efficiency and Risk of Endomyocardial Biopsy: Comparisons in Heart Transplant and Nontransplant Patients," Catheter Cardiovascular Diagnosis Journal, Sep. 1989, vol. 18, No. 1, pp. 7-11.
Carr et al., "Cardiosphere-Derived Cells Improve Function in the Infarcted Rat Heart for at Least 16 Weeks—an MRI Study", PLoS One, Oct. 2011, vol. 6, No. 10, pp. 1-10.
Declaration of Rachel Smith, PH.D., Curriculum Vitae, Exhibit A U.S. Appl. No. 13/412,051, 13 pages.
Edelberg et al., "Platelet-Derived Growth Factor-AB Limits the Extent of Myocardial Infarction in a Rat Model: Feasibility of Restoring Impaired Angiogenic Capacity in the Aging Heart", Circulation, 2002, vol. 150, No. 5, pp. 608-613.
Fernandez-Aviles et al., "Experimental and Clinical Regenerative Capability of Human Bone Marrow Cells After Myocardial Infarction", Circulation Research, 2004, vol. 95, pp. 742-748.
Heng et al., "Strategies for Directing the Differentiation of Stem Cells into the Cardiomyogenic Lineage in Vitro", Cardiovascular Research, 2004, vol. 62, pp. 34-42.
Hoppe et al., "Distinct Gene-Specific Mechanisms of Arrhythmia Revealed by Cardiac Gene Transfer of Two Long QT Disease Genes, HERG and KCNE1", Proceedings of the National Academy of Sciences of the United States of America, Apr. 24, 2001, vol. 98, No. 9, pp. 5335-5340.

Kobashigawa et al., "A Randomized Active-Controlled Trial of Mycophenolate Mofetil in Heart Transplant Recipients", Transplantation, Aug. 27, 1998, vol. 66, No. 4, pp. 507-515.
Li et al., "Skeletal Myoblast-Seeded Vascularized Tissue Scaffolds in the Treatment of a Large Volumetric Muscle Defect in the Rat Biceps Femoris Muscle", Termis, Tissue Engineering: Part A, vol. 23, No. 17 & 18, 2017, pp. 989-1000.
Limana et al., "Exogenous High-Mobility Group Box 1 Protein Induces Myocardial Regeneration after Infarction via Enhanced Cardiac C-Kit+ Cell Proliferation and Differentiation", Circulation Research, Oct. 14, 2005, vol. 97, No. 8, pp. 73-83.
Magarotto et al., "Muscle Functional Recovery is Driven by Extracellular Vesicles Combined with Muscle Extracellular Matrix in a Volumetric Muscle Loss Murine Model", Biomaterials 269, 2021, pp. 1-15.
Mason, "Techniques for Right and Left Ventricular Endomyocardial Biopsy", American Journal of Cardiology, 1978, vol. 41, No. 5, pp. 887-892.
Menasché et al., "Autologous Skeletal Myoblast Transplantation for Severe Postinfarction Left Ventricular Dysfunction", Journal of the American College of Cardiology, vol. 41, No. 7, Apr. 2, 2003, pp. 1078-1083.
Pfeffer et al., "Myocardial Infarct Size and Ventricular Function in Rats", Circulation Research, Apr. 1979, vol. 44, No. 4, pp. 503-512.
Pilia et al., "Transplantation and Perfusion of Microvascular Fragments in a Rodent Model of Volumetric Muscle Loss Injury", European Cells and Materials, vol. 28, 2014, pp. 11-24.
Schächinger et al., "Transplantation of Progenitor Cells and Regeneration Enhancement in Acute Myocardial Infarction: Final One-Year Results of the TOPCARE-AMI Trial", Journal of the American College of Cardiology, Oct. 19, 2004, vol. 44, No. 8, pp. 1690-1699.
Sicari et al., "An Acellular Biologic Scaffold Promotes Skeletal Muscle Formation in Mice and Humans with Volumetric Muscle Loss", Science Translational Medicine, Apr. 30, 2014, vol. 6, No. 234, pp. 1-10.
Siminiak et al., "Autologous Skeletal Myoblast Trans plantation for the Treatment of Postinfarction Myocardial Injury: Phase I Clinical Study with 12 Months of Follow-Up", American Heart Journal, Sep. 2004, vol. 148, No. 3, pp. 531-537.
Smits et al., "Catheter-Based Intramyocardial Injection of Autologous Skeletal Myoblasts as a Primary Treatment of Ischemic Heart Failure: Clinical Experience with Six-Month Follow-Up", Journal of the American College of Cardiology, 2003, vol. 42, No. 12, pp. 2063-2069.
Strauer et al., "Repair of infarcted Myocardium by Autologous Intracoronary Mononuclear Bone Marrow Cell Transplantation in Humans", Circulation, Oct. 8, 2002, vol. 106, No. 15, pp. 1913-1918.
Taylor et al., "A Randomized, Multicenter Comparison of Tacrolimus and Cyclosporine Immunosuppressive Regimens in Cardiac Transplantation: Decreased Hyperlipidemia and Hypertension with Tacrolimus", Journal Heart Lung Transplant, Apr. 1, 1999, vol. 18, No. 4, pp. 336-345.
USPTO Patent Trial and Appeal Board., "Decision on Appeal", in U.S. Appl. No. 13/412,051, dated Jun. 8, 2020, 12 pages.
USPTO Patent Trial and Appeal Board., "Declaration of Rachel R. Smith, PhD," in U.S. Appl. No. 13/412,051, dated Oct. 13, 2017, 32 pages.
Zeger et al., "Longitudinal Data Analysis for Discrete and Continuous Outcomes", Biometrics, Mar. 1986, vol. 42, No. 1, pp. 121-130.
Barile et al., "Beneficial Effects of Exosomes Secreted by Cardiac-Derived Progenitor Cells and Other Cell Types in Myocardial Ischemia", Stem Cell Investigation, Nov. 18, 2017, pp. 93-99.
Catalano, Mariadelva, "Engineering Exosomes Toward Folate Receptor Expressing Cells", Dec. 7, 2017, pp. 3.
Chen et al., "Transformation of Cell-Derived Microparticles into Quantum-Dot-Labeled Nanovectors for Antitumor siRNA Delivery", Angewandte Chemie International Edition, vol. 54, No. 3, Nov. 20, 2014, pp. 1036-1040.
De Couto et al., "Exosomal MicroRNA Transfer into Macrophages Mediates Cellular Postconditioning", Circulation, American Heart Association, vol. 136, No. 2, Jul. 11, 2017, pp. 200-214 (47 pages total).

(56) References Cited

OTHER PUBLICATIONS

Girard et al., "A Germline-Specific Class of Small RNAs Binds Mammalian Piwi Proteins", Nature, Jul. 13, 2006, vol. 442, pp. 199-202.

Ibrahim et al., "Augmenting Canonical Wnt Signaling in Therapeutically Inert Cells Converts them into Therapeutically Potent Exosome Factories", Nature Biomedical Engineering, Sep. 2019, vol. 3, pp. 695-705.

Ibrahim et al., "Small Molecule Inhibitors and Culture Conditions Enhance Therapeutic Cell and EV Potency via Activation of Beta-Catenin and Suppression of THY1", Nanomedicine: Nanotechnology, Biology, and Medicine, Dec. 13, 2020, vol. 33, pp. 7.

Kasai-Brunswick et al., "Cardiosphere-Derived Cells do not Improve Cardiac Function in Rats with Cardiac Failure," Stem Cell Research & Therapy, 2017, vol. 8, No. 36, 9 pages.

Kim, PhD et al., "Engineering Macrophage-Derived Exosomes for Targeted Paclitaxel Delivery to Pulmonary Metastases: in Vitroandin Vivoevaluations", Nanomedicine, Nanotechnology, Biology, and Medicine, vol. 14, 2018, pp. 195-204.

Kim, PhD et al., "Exosome Mediated Delivery of Paclitaxel for the Treatment of Multi Drug Resistant Pulmonary Metastases", Dissertation, Chapel Hill, Dec. 31, 2016, pp. 112.

Shen et al., "The Early Cryptic Transmission and Evolution of SARS-CoV-2 in Human Hosts", Available at SSRN 3724275, Aug. 2019, https://www.oyeyeah.com/wp-content/uploads/2020/11/SSRN-is3724275.pdf, pp. 22.

Smyth et al., "Surface Functionalization of Exosomes Using Click Chemistry", Bioconjugate Chemistry, vol. 25, No. 10, Sep. 30, 2014, pp. 1777-1784.

USPTO Patent Trial and Appeal Board., "Decision on Appeal", in U.S. Appl. No. 14/437,812, dated Jun. 19, 2020, 22 pages.

Vella et al., "PIWI-Interacting RNA (piRNA) Signatures in Human Cardiac Progenitor Cells", The International Journal of Biochemistry & Cell Biology, 2016, vol. 76, pp. 1-11.

Wan et al., "Aptamer-Conjugated Extracellular Nanovesicles for Targeted Drug Delivery", Cancer Research, vol. 78, No. 3, Dec. 7, 2017, pp. 798-808.

Wang et al., "The Use of RGD-Engineered Exosomes for Enhanced Targeting Ability and Synergistic Therapy Toward Angiogenesis", Nanoscale, vol. 9, No. 40, Jan. 1, 2017, pp. 15598-15605.

Zhang et al., "Magnetic and Folate Functionalization Enables Rapid Isolation and Enhanced Tumor-Targeting of Cell-Derived Microvesicles", ACS Nano, vol. 11, No. 1, Jan. 24, 2017, pp. 277-290.

\* cited by examiner

CDC-DERIVED EXOSOMES FOR TREATMENT OF VENTRICULAR TACHYARRYTHMIAS

CROSS REFERENCE TO RELATED APPLICATIONS

This application is the U.S. National Phase of International Application PCT/US2017/035846, filed Jun. 2, 2017, which claims the benefit of priority to U.S. Provisional Application Nos. 62/345,694 and 62/504,805, filed Jun. 3, 2016 and May 11, 2017, respectively. The disclosures of each of the foregoing applications are hereby incorporated by reference in their entireties.

GOVERNMENT SUPPORT

This invention was made with government support under R01 HL124074 awarded by the National Institutes of Health. The government has certain rights in the invention.

FIELD OF THE INVENTION

Described herein are methods and compositions related to exosomes, including extracellular vesicles for treatment and prevention of heart related disease and conditions, such as ventral arrhythmias, such as tachycardias.

BACKGROUND

Acute myocardial infarction (AMI) is experienced by more than 800,000 people in the United States annually and 75% of AMI victims survive 1 year. Approximately 300,000-350,000 of surviving patients die annually due to sudden cardiac death. Post-AMI, residual scarring of heart tissue can lead to ventricular tachycardia, which imparts a substantial risk of death. Ventricular tachycardia (VT) is a ventricular arrhythmia characterized by a fast pulse rate originating below the bundle of his and dissociated from the atria. Ventricular tachycardia may lead to Ventricular fibrillation (VF) which usually causes the person to collapse within seconds, and ends in death within minutes unless prompt corrective measures are instituted (CPR, defibrillation).

Placement of an implantable cardioverter-defibrillator (ICD) significantly reduces risk of death from VT and are implanted in more than 100,000 patients annually in the United States. Approximately 15% of patients receiving ICDs are initially treated with concomitant antiarrhythmic drug (AAD) therapy. ICDs can be very effective in terminating ventricular tachycardia, but recurrent arrhythmias and ICD shocks may cause impairment in the quality of life and are associated with an increased risk of death, heart failure, and hospitalization. Suppressive therapy, most commonly with AADs can prove problematic as pro-arrythmic, potential long term toxicity and systemic tolerance. Catheter ablation or radio frequency ablation can serve as alternatives to escalation in AAD drug therapy. However, ablation may introduce other adverse effects such as myocardial necrosis, cardiac perforation, bleeding and new arrhythmias. There is a great need in the art to develop therapeutic strategies that can reduce risk from post-MI scarring, VT and VF, and without adverse effects.

The death of cardiac myocytes is a major cause of myocardial infarct and heart failure, which may be addressed by the potential of cardiac regeneration in adult mammals. Stem cells, such as cardiosphere-derived cells (CDCs) have shown a proven therapeutic benefit by possibly tapping into the aforementioned repair and regeneration mechanisms. In addition, indirect mechanisms are responsible, where cellular exosomes (the lipid bilayer nanovesicles secreted by cells when multivesicular endosomes fuse with the plasma membrane) are central actors in the maintenance, repair and regeneration processes.

Described herein are compositions and methods related to use of exosomes, including CDC-derived exosomes for treatment and prevention of ventral arrhythmias, including tachycardias. In particular, the Inventors have discovered that extracellular vesicles, such as exosomes secreted from the cardiosphere derived cells (CDCs), are effective in reducing the propensity of the heart to lethal ventricular arrhythmias. The use of CDC-derived exosomes provides a less destructive alternative to radiofrequency ablation or cryoabalation of heart tissue, in patients susceptible to lethal ventricular arrhythmias. Focally injecting exosomes is capable of regrowing healthy heart muscle. Such result terminates the propensity to ventricular arrhythmias in subjects that have suffered a myocardial infarction.

SUMMARY OF THE INVENTION

Described herein is a method of treating a cardiac arrhythmia, including administering a therapeutically effective amount of a composition including extracellular vesicles to a subject afflicted with a cardiac arrhythmia, thereby treating the subject. In various embodiments, the method includes a subject that had a myocardial infarction. In various embodiments, the method includes subject with an implantable cardioverter-defibrillator (ICD). In various embodiments, the method includes a subject treated with initial antiarrhythmic drug (AAD) therapy. In various embodiments, the method includes a subject treated with escalating antiarrhythmic drug (AAD) therapy. In various embodiments, the method includes administering a composition comprises focal delivery at a site of isolated late potentials. In various embodiments, treating the subject comprises a reduction in the number of isolated late potentials. In various embodiments, treating the subject comprises a reduction in the isoelectric interval between late abnormal ventricular activity. In various embodiments, treating the subject comprises a decrease the incidence of inducible ventricular arrhythmias. In various embodiments, the cardiac arrhythmia comprises ventricular tachycardia. In various embodiments, the extracellular vesicles are obtained from cardiospheres, cardiosphere-derived cells (CDCs) or newt A1 cell line.

Described herein is a method of improving cardiac performance in a subject, including administering a composition including extracellular vesicles to a subject. In various embodiments, the subject is afflicted with abnormal electrical activity in the heart. In various embodiments, the subject is afflicted with slow zones of conduction in the heart. In various embodiments, the subject has heterogeneous areas of scarred myocardium. In various embodiments, the subject has had a myocardial infarction. In various embodiments, the subject has an implantable cardioverter-defibrillator (ICD). In various embodiments, administering a composition comprises focal delivery at a site of isolated late potentials.

Also described herein is a method of preventing arrhythmias in a subject including administering a composition comprising extracellular vesicles to a subject. In various embodiments, preventing arrhythmias in a subject comprises a reduction in the number of isolated late potentials. In various embodiments, preventing arrhythmias comprises a reduction in the isoelectric interval between late abnormal ventricular activity.

BRIEF DESCRIPTION OF FIGURES

FIG. 22A: Experimental protocol: 17 Yucatan mini pigs had an MI induced by 90-minute balloon occlusion of the proximal ⅓ of the LAD followed by 8 weeks of reperfusion. Cardiac function and scar size was examined by MRI (n=12). Arrhythmia Inducibility was probed by programmed electrical stimulation near the scar border of the LV. If no sustained arrhythmia was induced, PES was repeated at the RV apex. High density 3D electro-anatomic mapping was then performed (Rhythmia, Boston Scientific, Cambridge, Mass.). Inducible animals were then randomly assigned to receive a focal injection of either 7.5 mg of $CDC_{EXO}$ in 2 mls of IMDM, or 2 mls of IMDM alone. Injections were localized around the arrhythmogenic substrate where late potentials were identified (Rhythmia, Boston Scientific, Cambridge, Mass.), (NOGA, Biosense Webster). MRI, EAM, and PES was repeated 2 weeks later. Animals were then euthanized and the heart was removed en bloc and sectioned for histological analysis (n=5). FIG. 22B, left panel High density EAM (Rhythmia, Boston Scientific, Cambridge, Mass.) of the arrhythmogenic substrate with an identified late potential. FIG. 22B, right panel NOGA (Biosense Webster) guided injection site (Myostar, Biosense Webster) and representative catheter tip-potential.

FIG. 23 A, FIG. 23B: Short axis MRI images at end-diastole and end-systole from a vehicle injected control. FIG. 23C, FIG. 23D: A similar short axis view of a pig injected with $CDC_{EXO}$. FIG. 23E, FIG. 23F, FIG. 23G: At endpoint, significant improvement and preservation of LV ejection fraction was evident in $CDC_{EXO}$ pigs while a decrease in EF was seen in the controls, (P=0.01). FIG. 23H: Cardiac output was significantly improved in $CDC_{EXO}$ pigs relative to controls, P=0.01 FIG. 23I, FIG. 23J: Adverse changes in LV end-diastolic (LVEDV) and end-systolic (LVESV) volumes were observed in the vehicle treated group but not in $CDC_{EXO}$ pigs (LVESV, P=0.04). Chamber volumes were normalized to body 40.575 surface area ($0.121 \times BW^{A0.575}$).

FIG. 24A, FIG. 24B: 4-chamber MRI image of infarcted ventricular myocardium identified by late gadolinium enhancement (LGE). Left) Image pre injection of $CDC_{EXO}$ with follow up examination on the right. FIG. 24C, FIG. 24D: Representative 3D reconstruction of infarcted left ventricular myocardium pre and post injection with $CDC_{EXO}$. FIG. 24E, FIG. 24F, FIG. 24G: Contrasting an increase in scar in control (n=7) animals, there was a significant reduction in scar following focal injection of $CDC_{EXO}$ (n=7, P=0.009) at endpoint. There was no significant change in LV mass between timepoints in either group (supplement fig #).

FIG. 25A, FIG. 25B: Late potential map with a corresponding electrogram tracing from a $CDC_{EXO}$ treated pig pre- and post-injection. Of note is the isolated activation channel going through the identified substrate suggestive of a potential re-entrant pathway. This early channel is not as evident post treatment. FIG. 25C: There was no change in identifiable late potentials in the control animals following injection however FIG. 25D: there was a significant overall reduction in late potentials in the animals injected with $CDC_{EXO}$ (P=0.02). The white arrows identify the electrogram tracings pre- and post-treatment with an FIG. 25E:

identifiable reduction in timing of the late component of the electrogram post therapy within the same anatomic location (P=0.0004).

Figure 26:
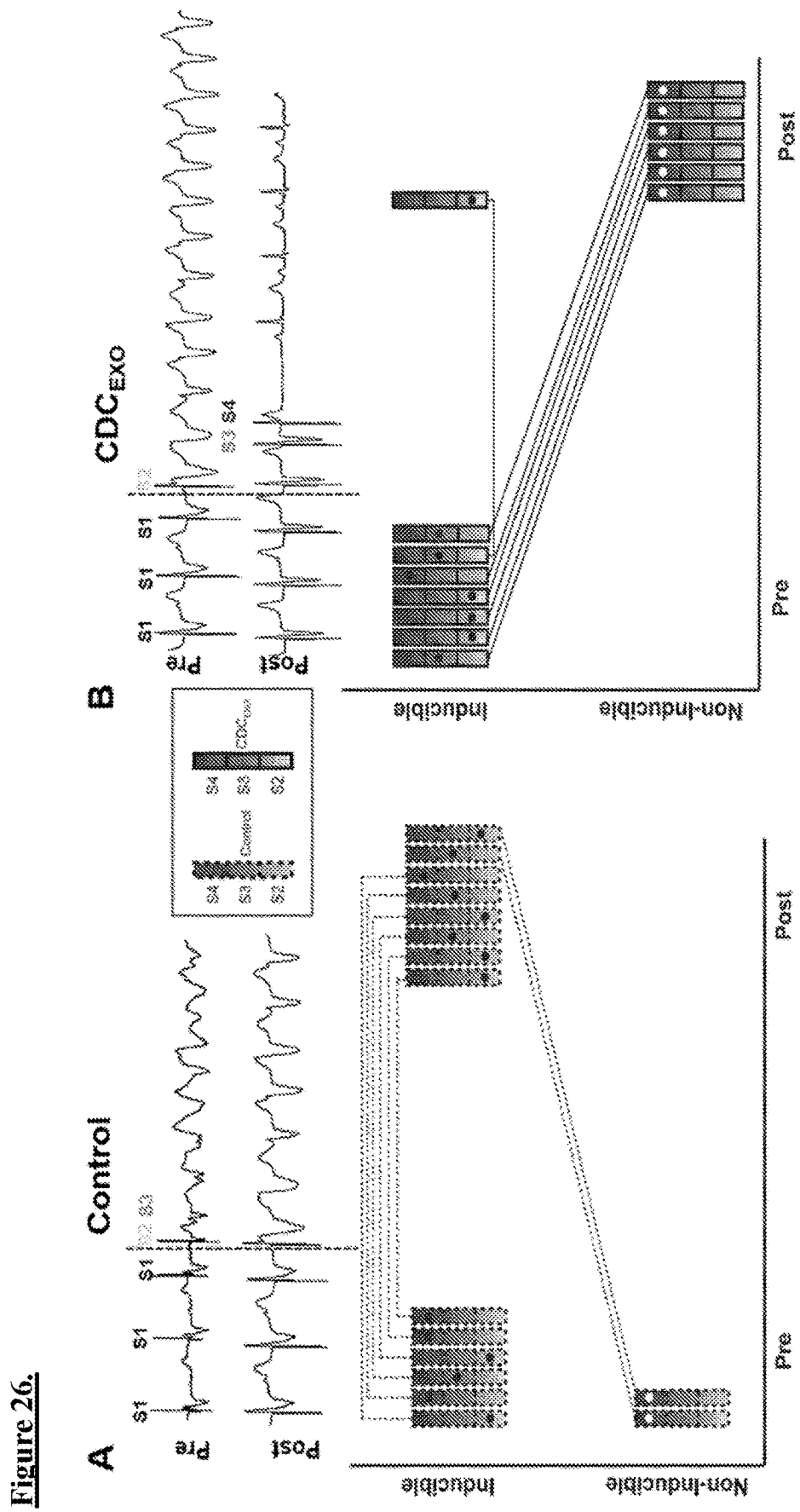

FIG. 26. FIG. 26A, FIG. 26B: Representative electrocardiogram tracings of programmed electrical stimulation (PES) with corresponding extra stimuli in the same animal performed 2 months post MI, and repeated 2 weeks following injection with left) vehicle alone or right) $CDC_{EXO}$. 7 inducible pigs allocated to the $CDC_{EXO}$ group displayed sustained ventricular arrhythmias at baseline, however only 1 pig was inducible at endpoint, demonstrating an 87.5% reduction in sustained inducible arrhythmias (P=0.015 Fisher's exact test). There was no change in arrhythmia Inducibility in the pigs injected with vehicle only. 2 of the control pigs were not inducible at baseline but were inducible at endpoint.

Figure 27:
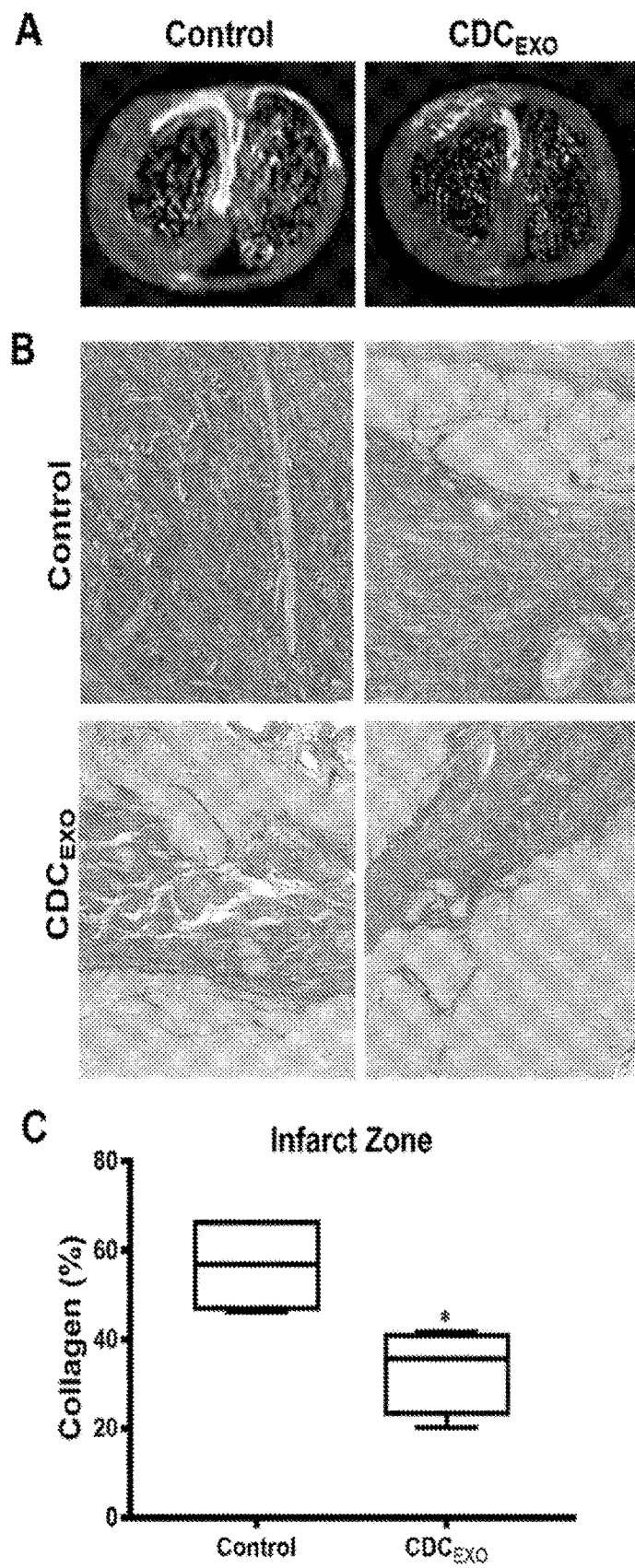

FIG. 27. FIG. 27A: Ex vivo LGE images of a control vs. a $CDC_{EXO}$ pig acquired at the same slice position. Note the moth-eaten pattern of gadolinium enhancement identifiable in the pig injected with $CDC_{EXO}$ whereas there is a transmural gadolinium pattern in the vehicle injected control. FIG. 27B, FIG. 27C: Picrosirius red stained sections of the infarct zone within the left ventricular myocardium revealed significantly reduced areas of fibrosis not identified in border and remote zones in $CDC_{EXO}$ injected pigs (P=0.02).

Figure 28:
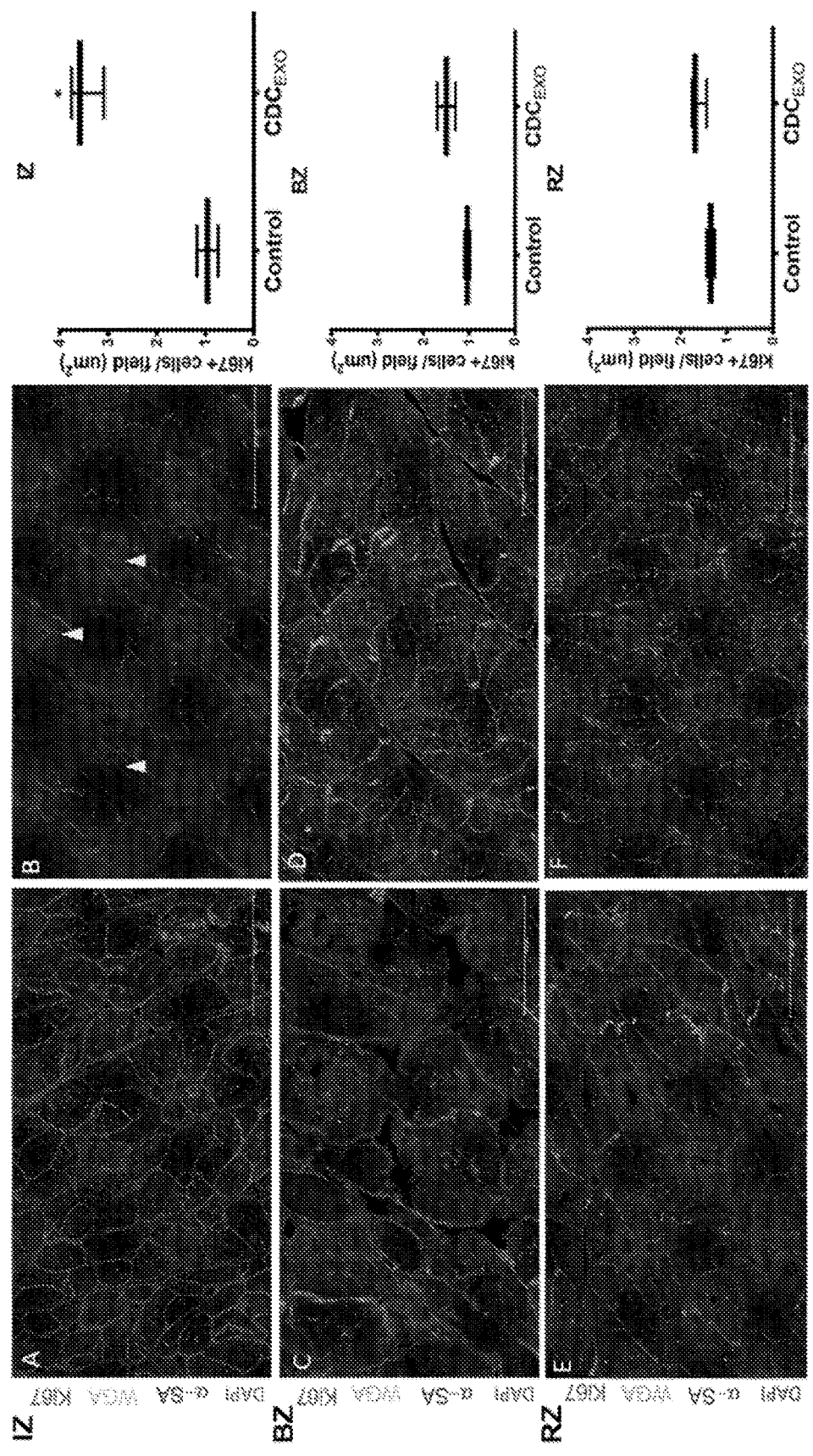

FIG. 28. Following euthanasia, hearts were sectioned into 1 cm slices from apex to base. The second most apical slices were sectioned into 3 anatomical zones including the anteroseptal infarct (IZ) and border (BZ) zones, as well a remote zones (RZ) acquired from the posterior wall. Paraffin embedded sections from the IZ, BZ, and RZ were then cut into ten 8 um sections from base to apex stained for DAPI (blue), WGA (green), α-SA (red), and Ki67 (magenta). Around the densest areas of injection there was a significant number of cells positive for both Ki67 and α-SA within the infarct zone of $CDC_{EXO}$ injected pigs compared to controls. Representative images from the infarct zone of a control animal (FIG. 28A) 0.95±0.21 cells/field ($\mu m^2$) n=2 and an animal injected with $CDC_{EXO}$ (FIG. 28B) 3.47±0.19 cells/field ($\mu m^2$), (n=3; P=0.0036). (FIG. 28C) Border zone images of a control animal 1.04±0.06 cells/field ($\mu m^2$), and (FIG. 28D) an animal injected with $CDC_{EXO}$ 1.5±0.11 cells/field ($\mu m^2$) (P=NS). Remote zone images from a control animal (FIG. 28E) 1.35±0.09% cells/field ($\mu m^2$), and an animal injected with $CDC_{EXO}$ (FIG. 29F) 1.62±0.10 cells/field ($\mu m^2$) (P=NS).

Figure 29:
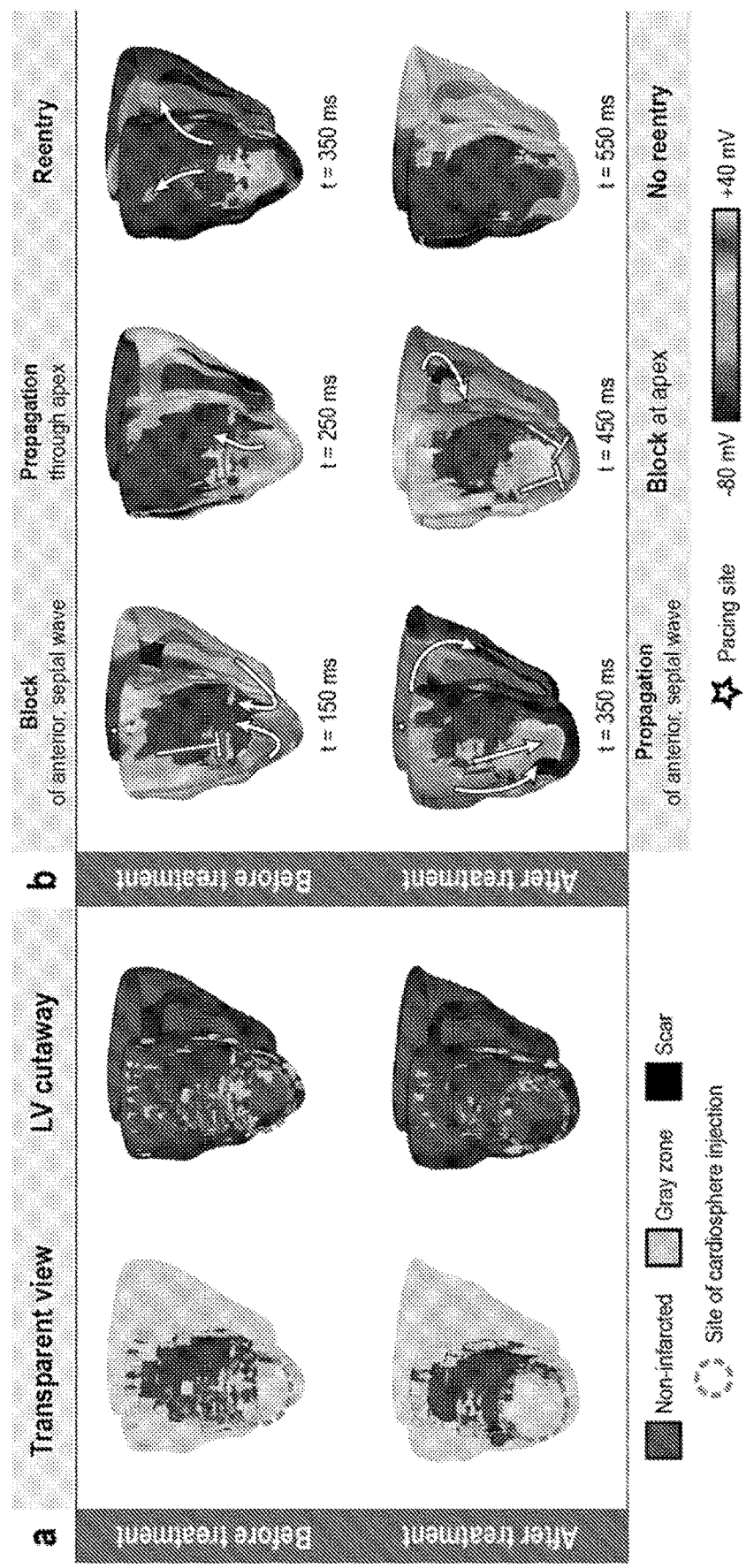

FIG. 29. Simulations with 3D computational models of a porcine heart before and after $CDC_{EXO}$ treatment. FIG. 29A: Reconstructed 3D models of ventricles before (top) and after (bottom) $CDC_{EXO}$ treatment. CDC-exosomes were injected in the inferior, anterior septum as outlined by the dotted green circle. Shown are scar and gray zone (GZ) in a transparent view of the ventricles (left) and in LV cutaways (right). FIG. 29B: Mechanisms demonstrating the conversion of the arrhythmogenic ventricular substrate into non-arrhythmogenic following $CDC_{EXO}$ injection. Transmembrane potential maps of ventricles before (top) and after (bottom) $CDC_{EXO}$ treatment are shown at three time points. The model ventricles were paced from the right ventricular outflow tract (star). The time instant below each map is counted from the delivery of last pacing stimulus. White arrows indicate direction of electrical propagation.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies *A Laboratory Manual* $2^{nd}$ ed., Cold Spring Harbor Press (Cold Spring Harbor N.Y., 2013); Kohler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Figure 1:
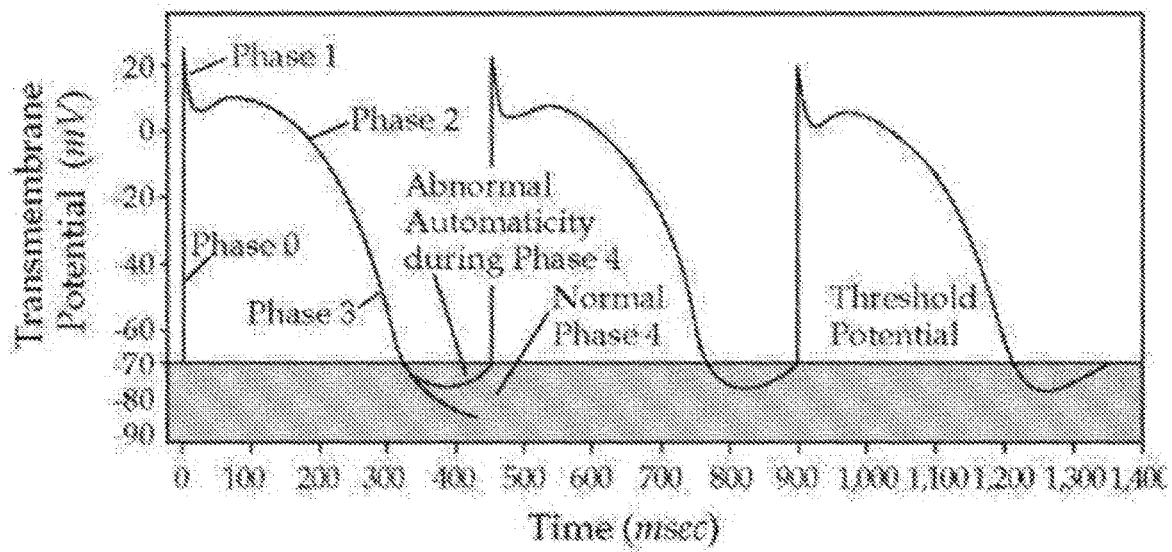
FIG. 1. Mechanisms of ventricular tachycardia (VT) are depicted.
Figure 1:
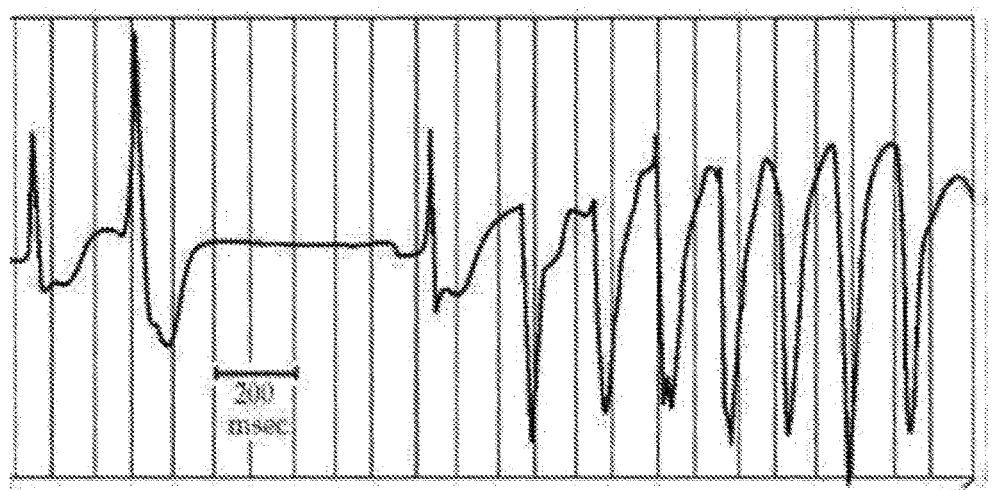
Figure 1:
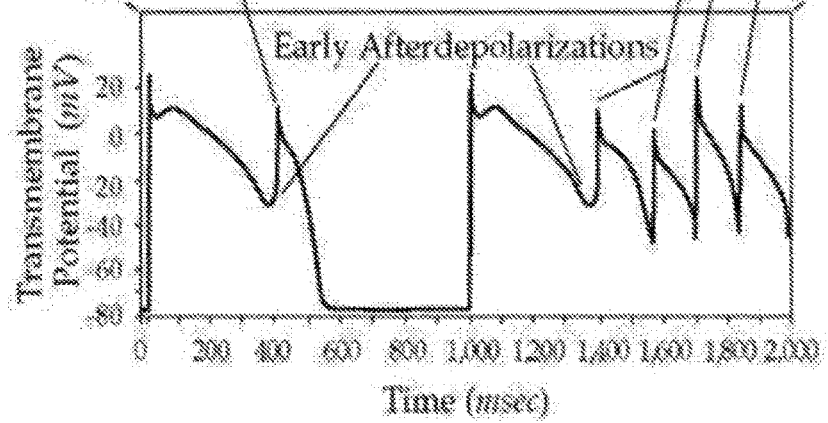
Figure 2:
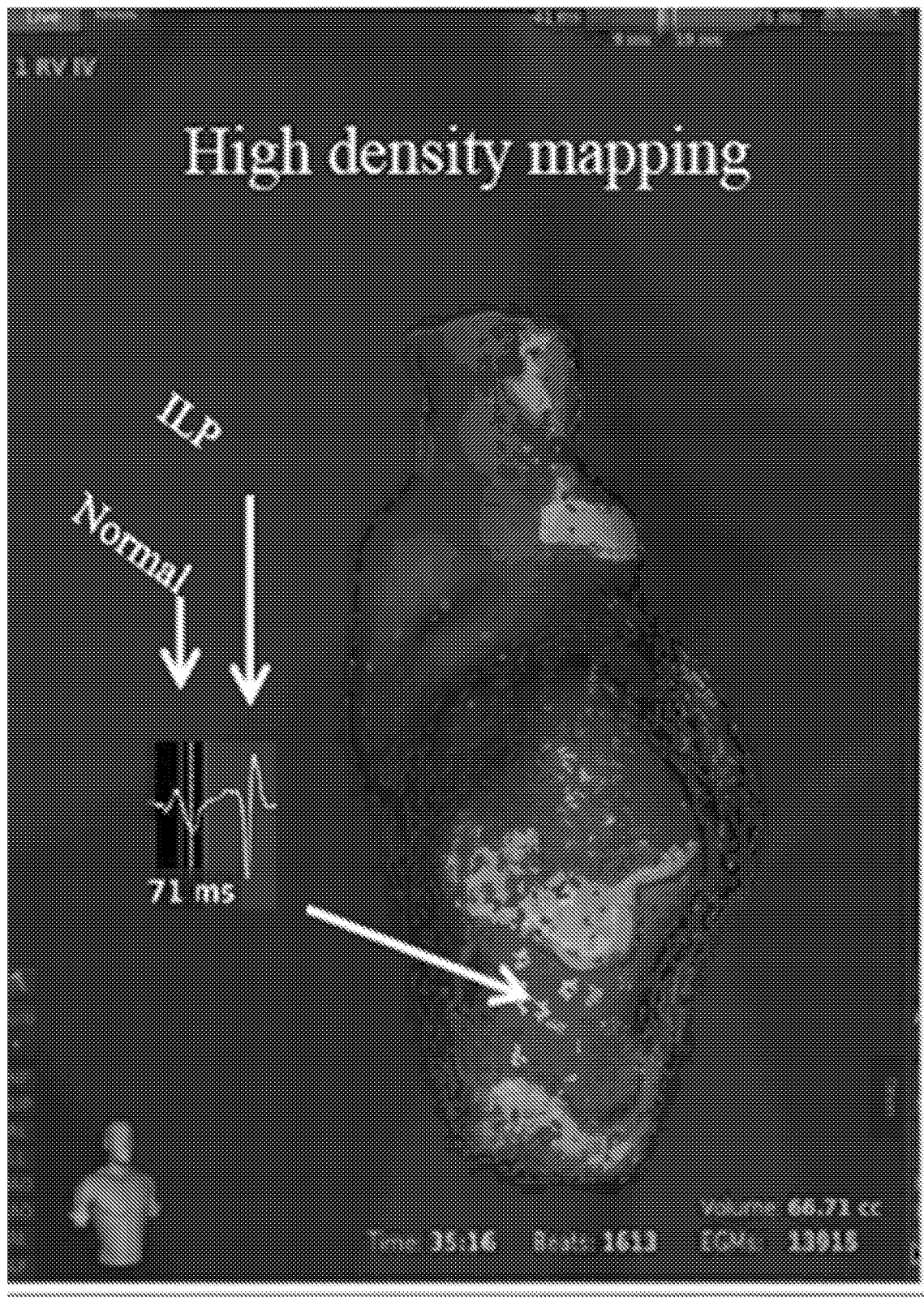
FIG. 2. Electroanatomic Mapping (EAM) demonstrating the presence of isolated late potentials (ILP), slow and fast arms associated with VT.

As described, after acute myocardial infarct, residual scarring of heart tissue can lead to ventricular tachycardia (VT), which imparts a substantial risk of death. As a ventricular arrhythmia, VT is characterized by a fast pulse rate originating below the bundle of his and dissociated from the atria. Current understanding of these mechanisms has resulted in 3 classification (FIG. 1). First, hypoxic cardiomyocytes may become exhibit abnormal automaticity and act as pacemaker cells. Second, triggered activity associated with afterdepolarizations (EAD, DAD). Third, reentrant ventricular tachycardia (VT) is the most common sustained arrhythmia leading to ventricular fibrillation (VF) post MI (FIG. 2). Reentrant VT in post-infarction cardiomyopathy depends on an isthmus of slow conduction near the border or within the infarct that is electrically isolated from the rest of the myocardium. In serious cases, electrical storm, an increasingly common and life-threatening emergency, is characterized by 3 or more sustained VT or VF episodes or appropriate ICD shocks within 24 hours, and despite drawbacks, early stage intervention radiofrequency ablation has been increasingly deployed as therapeutic intervention or prophylactically (including with ICD implantation).

Figure 3:
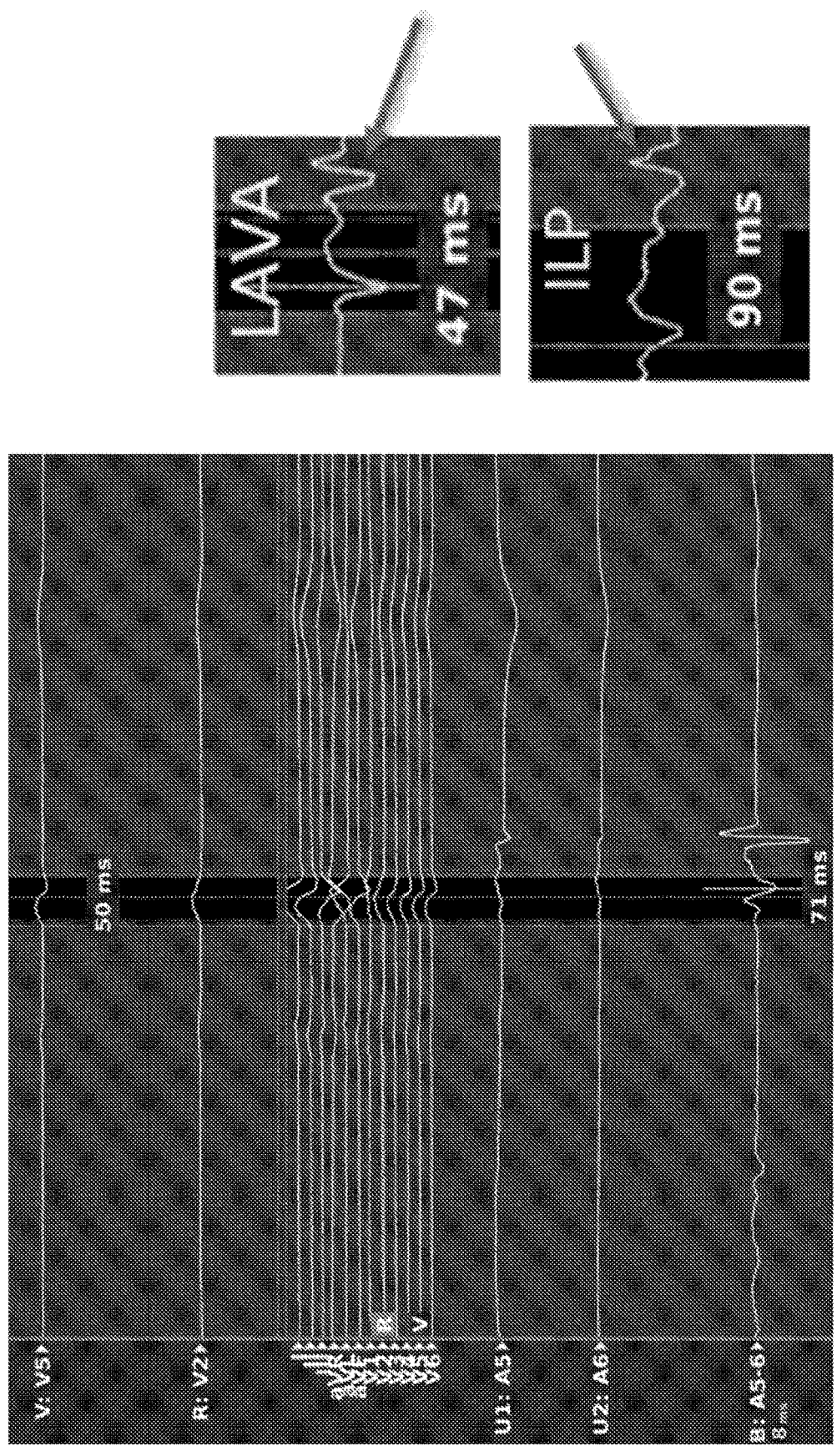
FIG. 3. Isolated late potentials and late abnormal ventricular activity as evidencing VTs, late potentials are shown relative to a normal QRS.
Figure 4:
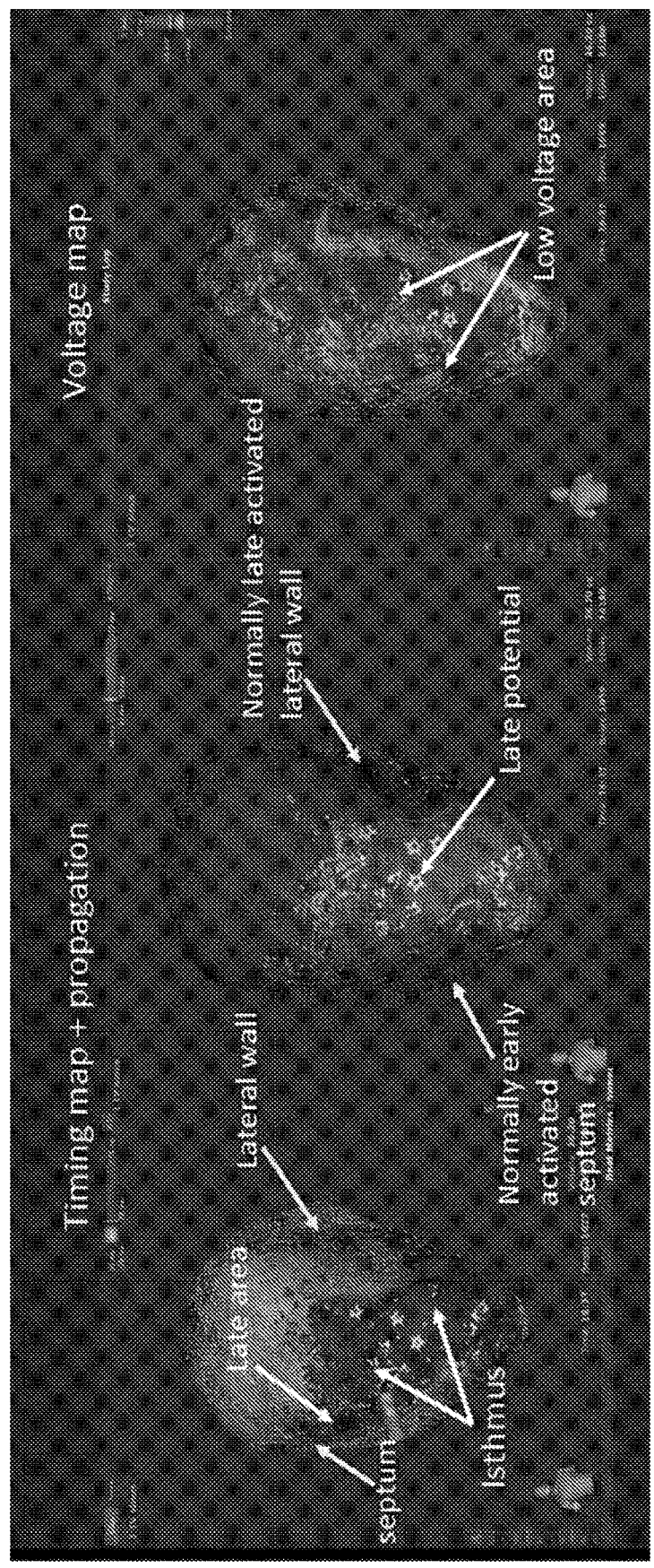
FIG. 4. Conduction during sinus rhythm including timing map and propagation, and voltage is depicted. Late potentials and low voltage areas are indicated.
Figure 5:
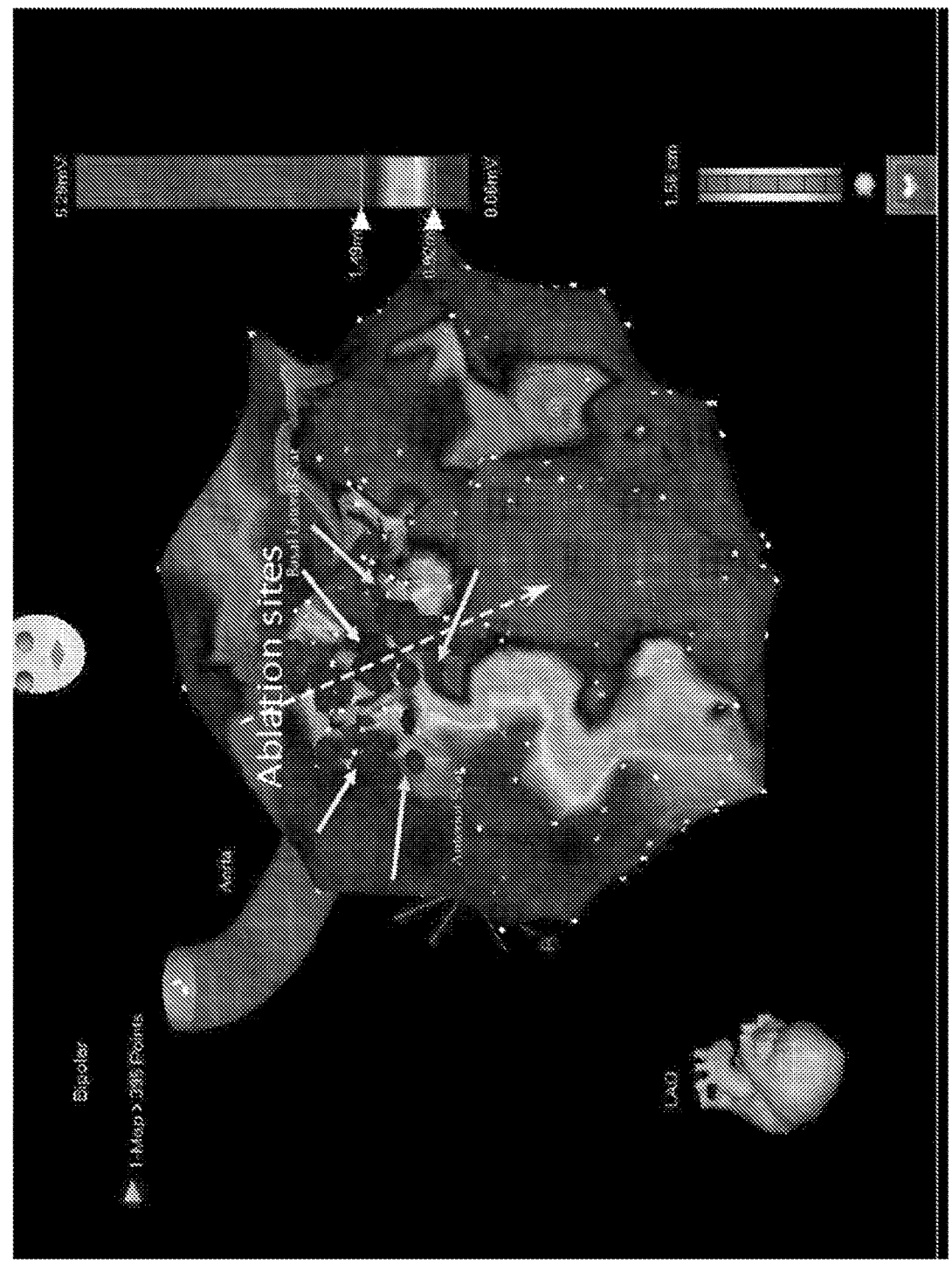
FIG. 5. Substrate ablation, Areas targeted for ablation are depicted.

Previous studies have demonstrated that these corridors of slow conduction within the scar provide the substrate for reentrant VT and often contain isolated late potentials (ILPs) (FIG. 3). VF is associated with a reentrant mechanism. These VT hallmarks of isolated late potentials and late abnormal ventricular activity are associated with bundles of viable myofibers within a zone of slow conduction, fractionated late activity during mid-diastole commonly associated with scar, occurrence when a single wavefront is split by a unidirectional block and normal QRS: 45-55 ms. In ischemic or nonischemic cardiomyopathy, the vulnerable substrate for reentry lies within heterogeneous areas of scarred myocardium. After an acute MI, or as nonischemic cardiomyopathy progresses, structural changes in the heart can lead to scar formation that creates areas of conduction block. However, surviving bundles of exist around the border of a scar. Slow conduction through these regions provides a pathway for electrically stable reentry. Otherwise harmless triggers, such as premature ventricular depolarization, is all that is required to initiate VT.

As described, current therapies include antiarrhythmic drugs (AAD) drugs such as Amiodarone, Lidocaine, Procainamide etc. Other approaches rely on RF Ablation, including targeted ablation (inducible/stable patients), substrate modification-(non-inducible/unstable patients) 3D mapping and identification of late potentials and area of slow conduction. When subjects have proven refractory to AAD therapy, radio frequency (RF) catheter ablation has been reported as more effective than escalated AAD therapy in reducing the rate of the combined outcome of death at any time or ventricular tachycardia storm or ICD shocks after 30 days. RF ablation has been increasingly deployed as therapeutic intervention or prophylactically (including with ICD implantation). This includes in serious conditions such as electrical storm, characterized by 3 or more sustained VT or VF episodes or appropriate ICD shocks within 24 hours. Many adverse effects are associated with the aforementioned techniques.

Cardiosphere-Derived Cells (CDCs)

CDCs are a population of cells generated by manipulating cardiospheres, cultured cells initially obtained from heart sample biopsies, subsequently cultured as explants and suspension cultured cardiospheres. For example, CDCs can be generated by plating cardiospheres on a solid surface which is coated with a substance which encourages adherence of cells to a solid surface of a culture vessel, e.g., fibronectin, a hydrogel, a polymer, laminin, serum, collagen, gelatin, or poly-D-lysine, and expanding same as an adherent monolayer culture. CDCs can be repeatedly passaged, e.g., passaged two times or more, according to standard cell culturing methods.

Extracellular Vesicles

Extracellular vesicles include lipid bilayer structures generated by cells, and include exosomes, microvesicles, membrane particles, membrane vesicles, exosome-like vesicles, ectosomes, ectosome-like vesicles, or exovesicles. Exosomes are vesicles formed via a specific intracellular pathway involving multivesicular bodies or endosomal-related regions of the plasma membrane of a cell. Exosomes can range in size from approximately 20-150 nm in diameter. In some cases, they have a characteristic buoyant density of approximately 1.1-1.2 g/mL, and a characteristic lipid composition. Their lipid membrane is typically rich in cholesterol and contains sphingomyelin, ceramide, lipid rafts and exposed phosphatidylserine. Exosomes express certain marker proteins, such as integrins and cell adhesion molecules, but generally lack markers of lysosomes, mitochondria, or caveolae. In some embodiments, the exosomes contain cell-derived components, such as but not limited to, proteins, DNA and RNA (e.g., microRNA and noncoding RNA). In some embodiments, exosomes can be obtained from cells obtained from a source that is allogeneic, autologous, xenogeneic, or syngeneic with respect to the recipient of the exosomes.

Certain types of RNA, e.g., microRNA (miRNA), are known to be carried by exosomes. miRNAs function as post-transcriptional regulators, often through binding to complementary sequences on target messenger RNA transcripts (mRNAs), thereby resulting in translational repression, target mRNA degradation and/or gene silencing. For example, miR146a exhibits over a 250-fold increased expression in CDCs, and miR210 is unregulated approximately 30-fold, as compared to the exosomes isolated from normal human dermal fibroblasts.

Methods for preparing exosomes can include the steps of: culturing cardiospheres or CDCs in conditioned media, isolating the cells from the conditioned media, purifying the exosome by, e.g., sequential centrifugation, and optionally, clarifying the exosomes on a density gradient, e.g., sucrose density gradient. In some instances, the isolated and purified exosomes are essentially free of non-exosome components, such as components of cardiospheres or CDCs. Exosomes can be resuspended in a buffer such as a sterile PBS buffer containing 0.01-1% human serum albumin. The exosomes may be frozen and stored for future use.

Extracellular vesicles originating from newt A1 cell line (Newt-EVs) are obtained after filtering A1 cell line CM containing EVs through a 10 KDa pore size filter following a similar process as for CDC-EV production. Newt-EVs are a non-cellular, filter sterilized product obtained from newt A1 cells cultured under defined, serum-free conditions. The final product, composed of secreted EVs and concentrated CM, is formulated in PlasmaLyte A and stored frozen. The frozen final product is ready to use for direct subconjunctival injection after thawing.

Exosomes can be prepared using a commercial kit such as, but not limited to the ExoSpin™ Exosome Purification Kit, Invitrogen® Total Exosome Purification Kit, PureExo® Exosome Isolation Kit, and ExoCap™ Exosome Isolation kit. Methods for isolating exosome from stem cells are found in, e.g., Tan et al., Journal of Extracellular Vesicles, 2:22614 (2013); Ono et al., Sci Signal, 7(332):ra63 (2014) and methods for isolating exosome from cardiosphere-derived cells are found in, e.g., Ibrahim et al., Stem Cell Reports, 2:606-619 (2014), each of which is incorporated by reference herein. Collected exosomes can be concentrated and/or purified using methods known in the art. Specific methodologies include ultracentrifugation, density gradient, HPLC, adherence to substrate based on affinity, or filtration based on size exclusion.

For example, differential ultracentrifugation has become a leading technique wherein secreted exosomes are isolated from the supernatants of cultured cells. This approach allows for separation of exosomes from nonmembranous particles, by exploiting their relatively low buoyant density. Size exclusion allows for their separation from biochemically similar, but biophysically different microvesicles, which possess larger diameters of up to 1,000 nm. Differences in flotation velocity further allows for separation of differentially sized exosomes. In general, exosome sizes will possess a diameter ranging from 30-200 nm, including sizes of 40-100 nm. Further purification may rely on specific properties of the particular exosomes of interest. This includes, e.g., use of immunoadsorption with a protein of interest to select specific vesicles with exoplasmic or outward orientations.

Among current methods, e.g., differential centrifugation, discontinuous density gradients, immunoaffinity, ultrafiltration and high performance liquid chromatography (HPLC), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/mL) or application of a discrete sugar cushion in preparation.

Importantly, ultrafiltration can be used to purify exosomes without compromising their biological activity. Membranes with different pore sizes—such as 100 kDa molecular weight cut-off (MWCO) and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. HPLC can also be used to purify exosomes to homogeneouslysized particles and preserve their biological activity as the preparation is maintained at a physiological pH and salt concentration.

Other chemical methods have exploited differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick®, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to microsized particles (e.g., organelles and cells) and which has been successfully applied to fractionate exosomes from culture media.

Beyond these techniques relying on general biochemical and biophysical features, focused techniques may be applied to isolate specific exosomes of interest. This includes relying on antibody immunoaffinity to recognizing certain exosome-associated antigens. As described, exosomes further express the extracellular domain of membrane-bound receptors at the surface of the membrane. This presents a ripe opportunity for isolating and segregating exosomes in connections with their parental cellular origin, based on a shared antigenic profile. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

Described herein are compositions and methods providing significant benefits in the treatment of abnormal cardiac electrical activity or cardiac arrhythmia, including repair or regeneration of damaged or diseased tissues using extracellular vesicles, including exosomes such as CDC-derived exosomes and newt A1 cell line exosomes. Certain supporting techniques are described in, for example, U.S. application Ser. Nos. 11/666,685, 12/622,143, 12/622,106, 14/421, 355, PCT App. No. PCT/US2013/054732, PCT/US2015/ 053853, PCT/US2015/054301 and PCT/US2016/035561, which are fully incorporated by reference herein.

Described herein is a method of treatment for a heart related disease and/or condition. In various embodiments, the heart related disease and/or condition includes abnormal cardiac electrical activity or cardiac arrhythmia. In various embodiments, the method is for treating abnormal cardiac electrical activity, including administering a composition including extracellular vesicles to a subject, thereby treating the subject. In various embodiments, the method is for treating a cardiac arrhythmia, including administering a composition including extracellular vesicles to a subject, thereby treating the subject. In various embodiments, the method of treatment includes, selecting a subject in need of treatment, administering a composition including extracellular vesicles to the individual, wherein administration of the composition treats the subject. In various embodiments, the subject is afflicted with incessant ventricular tachycardia (VT). In various embodiments, the subject is afflicted with ischaemic heart disease and recurrent implantable cardioverter-defibrillator (ICD) shocks. In various embodiments, the subject has experienced a first episode of sustained VT, afflicted with ischaemic heart disease, without or without an implanted ICD. In various embodiments, the subject is afflicted with electrical storm, including electrical storm arising from ventricular arrhythmias such as VT, ventricular fibrillation (VF), or appropriate ICD shocks. In various embodiments, the subject is afflicted with recurrent electrical storm, including electrical storm arising from ventricular arrhythmias such as VT, ventricular fibrillation (VF), or appropriate implantable cardioverter-defibrillator (ICD) shocks.

In various embodiments, the cardiac arrhythmia includes extra beats, supraventricular tachycardias, ventricular arrhythmias, and bradyarrhythmias. In various embodiments, the cardiac arrhythmia includes premature atrial contractions and premature ventricular contractions. In various embodiments, the cardiac arrhythmia includes atrial fibrillation, atrial flutter, and paroxysmal supraventricular tachycardia. In various embodiments, the cardiac arrhythmia includes ventricular fibrillation and ventricular tachycardia. In various embodiments, ventricular tachycardia (VT) is monomorphic VT or polymorphic VT. In various embodiments, monomorphic VT is characterized by ventricular activation sequence without any variation in the QRS complexes. In various embodiments, polymorphic VT is characterized by beat-to-beat variations in the QRS complexes.

In various embodiments, the abnormal cardiac electrical includes sick sinus syndrome, sinus bradycardia, tachycardia-bradycardia syndrome, atrial fibrillation, atrioventricular block, chronotropic incompetence, prolonged QT syndrome, and heart failure.

In various embodiments, the subject has had a myocardial infarction. In various embodiments, the subject is post-myocardial infarct. In various embodiments, the subject is afflicted with abnormal cardiac electrical activity or cardiac arrhythmia. In various embodiments, the subject was treated with initial antiarrhythmic drug (AAD) therapy. In various embodiments, the subject was treated with escalating AAD therapy. In various embodiments, the method is administered concurrently, or sequential to initial and/or escalating AAD therapy. In various embodiments, AAD therapeutic agents include Amiodarone, Lidocaine, Procainamide, among others. In various embodiments, the subject is refractory to AAD therapy.

In various embodiments, administration of extracellular vesicles, including exosomes, includes focal delivery at a site of isolated late potentials, isthmus and/or slow zones of conduction. In various embodiments, a site of isolated potential (i.e. arrhythmogenic substrate), isthmus and/or slow zones of conduction has been identified by electrical anatomic mapping. In various embodiments, a 12-lead electrocardiogram has identified a region of interest for electrical anatomic mapping. In various embodiments, administration includes injection in the intra and peri-infarct zone of the left ventricle. In various embodiments, this includes, 3, 4, 5, 6, 7, 8, 9, 10 or more injection at the aforementioned sites. In various embodiments, administration of extracellular vesicles, including exosomes, to the subject occurs through any of known techniques in the art. In some embodiments, this includes percutaneous delivery and/or injection into heart muscle. Additional delivery sites include any one or more compartments of the heart, such as myocardium, associated arterial, venous, and/or ventricular locations. In certain embodiments, administration can include delivery to a tissue or organ site that is the same as the site of diseased and/or dysfunctional tissue. In certain embodiments, administration can include delivery to a tissue or organ site that is different from the site or diseased and/or dysfunctional tissue.

In various embodiments, the extracellular vesicles are exosomes, microvesicles, membrane particles, membrane vesicles, exosome-like vesicles, ectosomes, ectosome-like vesicles, or exovesicles. In various embodiments, the exosomes are CDC-derived exosomes or newt A1 cell line derived exosomes. In other embodiments, the exosomes include one or more microRNAs. In various embodiments, these microRNAs can include miR-146a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and/or miR-23a. In several embodiments, the exosomes includes one or more exosomes enriched in at least one of miR-146a, miR-22, miR-24. In other embodiments, the exosomes can include one or more exosomes containing microRNAs. This includes various microRNAs known in the art, such as miR-1469, miR-762, miR-574-3p, miR-574-5p, miR-3197, miR-4281, miR-1976, miR-1307, miR-1224-3p, miR-187, miR-3141, miR-1268, miR-155, miR-122, miR-638, miR-3196, miR-223, miR-4267, miR-1281, miR-885-5p, miR-663, miR-let-7b, miR-29d, miR-144, miR-let-7e 143, miR-lrt-7g, miR-17a, miR-125a-5p, miR-128, miR-720, miR-21, miR-30c, miR-30b, miR-lb.

In various embodiments, administration of the extracellular vesicles includes administration of a therapeutically effective amount of the extracellular vesicles. In various embodiments, a therapeutically effective amount include an amount capable of altering gene expression in damaged or dysfunctional tissue, improves viability of the damaged tissue, and/or enhances regeneration or production of new tissue in the individual. In various embodiments, the quantities of extracellular vesicles, including exosomes, that are administered to achieved these effects range from $1 \times 10^6$ to $1 \times 10^7$, $1 \times 10^7$ to $1 \times 10^8$, $1 \times 10^8$ to $1 \times 10^9$, $1 \times 10^9$ to $1 \times 10^{10}$, $1 \times 10^{10}$ to $1 \times 10^{11}$, $1 \times 10^{11}$ to $1 \times 10^{12}$, $1 \times 10^{12}$ or more. In other embodiments, the numbers of exosomes is relative to the number of cells used in a clinically relevant dose for a cell-therapy method. For example, it has been demonstrated that 3 mL/$3 \times 10^5$ human cardiac-derived cells (CDCs), is capable of providing therapeutic benefit in intracoronary administration, and therefore, a quantity of extracellular vesicles, including exosomes, as derived from that number of cells in a clinically relevant dose for a cell-therapy method. In various embodiments, administration can be in repeated doses. For example, defining an effective dose range, dosing regimen and route of administration, may be guided by studies using fluorescently labeled exosomes, and measuring target tissue retention, which can be >10×, >50×, or >100× background, as measured 5, 10, 15, 30, or 30 or more min as a screening criterion. In certain embodiments, >100× background measured at 30 mins is a baseline measurement for a low and high dose that is then assessed for safety and bioactivity (e.g., using MRI endpoints: scar size, global and regional function). In various embodiments, single doses are compared to two, three, four, four or more sequentially-applied doses. In various embodiments, the repeated or sequentially-applied doses are provided for treatment of an acute disease and/or condition. In various embodiments, the repeated or sequentially-applied doses are provided for treatment of a chronic disease and/or condition.

In some embodiments, the method of treatment results in a reduction in scar mass, reduction in the formation of scar mass, improvements in ejection fraction, reductions in diastolic volume and systolic volume. In other embodiments, this includes a reduction in the number, timing and magnitude of late potentials, or reduction in inducibility of potentials. For example, this includes reducing the isoelectric interval between late abnormal ventricular activity, and decreasing the incidence of inducible ventricular arrhythmias. In other embodiments, the method of treatment results in increases in viable tissue, reduction in scar mass, improvements in wall thickness, regenerative remodeling of injury sites, enhanced angiogenesis, improvements in cardiomyogenic effects, reduction in apoptosis, reduction in fibrosis, and/or decrease in levels of pro-inflammatory cytokines. In various embodiments, the methods of treatment results in reduction of slow conduction zones. In various embodiments, the method of treatment includes assessing one or more of the aforementioned electrophysiological properties.

In various embodiments, the damaged or dysfunctional tissue is in need of repair, regeneration, or improved function due to an acute event. Acute events include, but are not limited to, trauma such as laceration, crush or impact injury, shock, loss of blood or oxygen flow, infection, chemical or heat exposure, poison or venom exposure, drug overuse or overexposure, and the like. In certain embodiments, the damaged tissue is pulmonary, arterial or capillary tissue, such as the endothelial lining of distal pulmonary arteries. In other embodiments, the damaged tissue is cardiac tissue and the acute event includes a myocardial infarction. In some embodiments, administration of the exosomes results in an increase in cardiac wall thickness in the area subjected to the infarction.

In other embodiments, damaged or dysfunctional tissue is due to chronic disease, such as for example congestive heart failure, including as conditions secondary to diseases such as emphysema, ischemic heart disease, hypertension, valvular heart disease, connective tissue diseases, HIV infection, liver disease, sickle cell disease, dilated cardiomyopathy, infection such as Schistosomiasis, diabetes, and the like. In various embodiments, the administration can be in repeated doses, such as two, three, four, four or more sequentially-applied doses. In various embodiments, the repeated or sequentially-applied doses are provided for treatment of an acute disease and/or condition. In various embodiments, the repeated or sequentially-applied doses are provided for treatment of a chronic disease and/or condition.

Described herein is a method of preventing a heart related disease and/or condition. In various embodiments, the heart related disease and/or condition includes abnormal cardiac electrical activity or cardiac arrhythmia. In various embodiments, the method of prevention is for abnormal cardiac electrical activity, includes administering a composition including extracellular vesicles to a subject, thereby preventing abnormal cardiac electrical activity in the subject. In various embodiments, the method of prevention is for a cardiac arrhythmia, including administering a composition including extracellular vesicles to a subject, thereby preventing cardiac arrhythmia in the subject. In various embodiments, administration of extracellular vesicles, including exosomes, includes focal delivery at a site of isolated late potentials (i.e., arhythmogenic substrate), isthmus and/or slow zones of conduction. In various embodiments, a site of isolated potential (i.e., arrhythmogenic substrate), isthmus and/or slow zones of conduction have been identified by electrical anatomic mapping. In various embodiments, a 12-lead electrocardiogram has identified a region of interest for electrical anatomic mapping. In various embodiments, administration includes injection in the intra and pen-infarct zone of the left ventricle. In various embodiments, this includes 3, 4, 5, 6, 7, 8, 9, 10 or more injection at the aforementioned sites. In various embodiments, administration of extracellular vesicles, including exosomes, to the subject occurs through any of known techniques in the art.

In various embodiments, the subject is afflicted with incessant ventricular tachycardia (VT). In various embodiments, the subject is afflicted with ischaemic heart disease and recurrent implantable cardioverter-defibrillator (ICD) shocks. In various embodiments, the subject has experienced a first episode of sustained VT, afflicted with ischaemic heart disease, without or without an implanted ICD. In various embodiments, the subject is afflicted with electrical storm, including electrical storm arising from ventricular arrhythmias such as VT, ventricular fibrillation (VF), or appropriate ICD shocks. In various embodiments, the subject is refractory to AAD therapy. In various embodiments, the subject is afflicted with a decline in left ventricle function.

In some embodiments, the method of prevention includes a reduction in the number, timing and magnitude of late potentials, or reduction in inducibility of potentials. For example, this includes reducing the isoelectric interval between late abnormal ventricular activity, and decreasing the incidence of inducible ventricular arrhythmias. In various embodiments, the methods of prevention results in reduction of slow conduction zones. In various embodiments, the method of prevention reduces the incidence and/or recurrence of implantable cardioverter-defibrillator (ICD) shocks, electrical storm. In various embodiments, the method of prevention includes assessing one or more of the aforementioned electrophysiological properties.

Further described herein is a method of improving cardiac performance in a subject. In various embodiments, the method includes administering a composition including extracellular vesicles to a subject, thereby improving cardiac performance in the subject. In various embodiments, the method of improving cardiac performance includes, selecting a subject afflicted with a heart related disease/condition, administering a composition including extracellular vesicles to a subject, thereby improving cardiac performance in the subject. In various embodiments, the subject has previously suffered myocardial infarct. In various embodiments, the subject is post-myocardial infarct. In various embodiments, the subject is afflicted with abnormal cardiac electrical activity or cardiac arrhythmia. In various embodiments, the subject is afflicted with recurrent electrical storm, including electrical storm arising from ventricular arrhythmias such as ventricular tachycardia (VT), ventricular fibrillation (VF), or appropriate implantable cardioverter-defibrillator (ICD) shocks. In various embodiments, the extracellular vesicles are exosomes, microvesicles, membrane particles, membrane vesicles, exosome-like vesicles, ectosomes, ectosome-like vesicles, or exovesicles. In various embodiments, the exosomes are CDC-derived exosomes or newt A1 cell line derived exosomes. In various embodiments, administration of extracellular vesicles, including exosomes, includes focal delivery at a site of isolated late potentials, isthmus and/or slow zones of conduction. In various embodiments, a site of isolated potential, isthmus and/or slow zones of conduction have been identified by electrical anatomic mapping. In various embodiments, a 12-lead electrocardiogram has identified a region of interest for electrical anatomic mapping. In various embodiments, administration includes injection in the intra and pen-infarct zone of the left ventricle. In various embodiments, this includes 3, 4, 5, 6, 7, 8, 9, 10 or more injection at the aforementioned sites. In various embodiments, administration of extracellular vesicles, including exosomes, to the subject occurs through any of known techniques in the art.

In some embodiments, improving cardiac performance includes a reduction in scar mass, reduction in the formation of scar mass, improvements in ejection fraction, reductions in diastolic volume and systolic volume. In other embodiments, this includes a reduction in the number, timing and magnitude of late potentials, or reduction in inducibility of potentials. For example, this includes reducing the isoelectric interval between late abnormal ventricular activity, and decreasing the incidence of inducible ventricular arrhythmias. In other embodiments, improving cardiac performance relates to increases in viable tissue, improvements in wall thickness, regenerative remodeling of injury sites, enhanced angiogenesis, improvements in cardiomyogenic effects, reduction in apoptosis, reduction in fibrosis, and/or decrease in levels of pro-inflammatory cytokines. In various embodiments, the methods results in reduction of slow conduction zones. In various embodiments, the method includes assessing one or more of the aforementioned electrophysiological properties.

In various embodiments, the subject has had a myocardial infarction. In various embodiments, the subject is post-myocardial infarct. In various embodiments, the subject is afflicted with abnormal cardiac electrical activity or cardiac arrhythmia. In other embodiments, improving cardiac performance includes a decrease in the incidence of electrical storm.

In various embodiments, administration of the extracellular vesicles includes administration of a therapeutically effective amount of the extracellular vesicles. In various embodiments, a therapeutically effective amount include an amount capable of altering gene expression in damaged or dysfunctional tissue, improves viability of the damaged tissue, and/or enhances regeneration or production of new tissue in the individual. In various embodiments, administering a composition includes multiple dosages of the exosomes. In various embodiments, the repeated or sequentially-applied doses are provided for treatment of an acute disease and/or condition. In various embodiments, the repeated or sequentially-applied doses are provided for treatment of a chronic disease and/or condition. In other embodiments, administering a composition includes percutaneous injection. In other embodiments, administering a composition includes injection into heart muscle. In other embodiments, administering a composition includes myocardial infusion. In other embodiments, administering a composition includes use of a intracoronary catheter. In other embodiments, administration a composition includes intra-arterial or intravenous delivery. Additional delivery sites include any one or more compartments of the heart, such as myocardium, associated arterial, venous, and/or ventricular locations. In certain embodiments, administration can include delivery to a tissue or organ site that is the same as the site of diseased and/or dysfunctional tissue. In certain embodiments, administration can include delivery to a tissue or organ site that is different from the site or diseased and/or dysfunctional tissue. In other embodiments, extracellular vesicle, including exosomes, therapy is provided in combination with standard therapy for a disease and/or condition. This may include co-administration of the extracellular vesicle, including exosomes, with a therapeutic agent.

Example 1

Study Design

Figure 6:
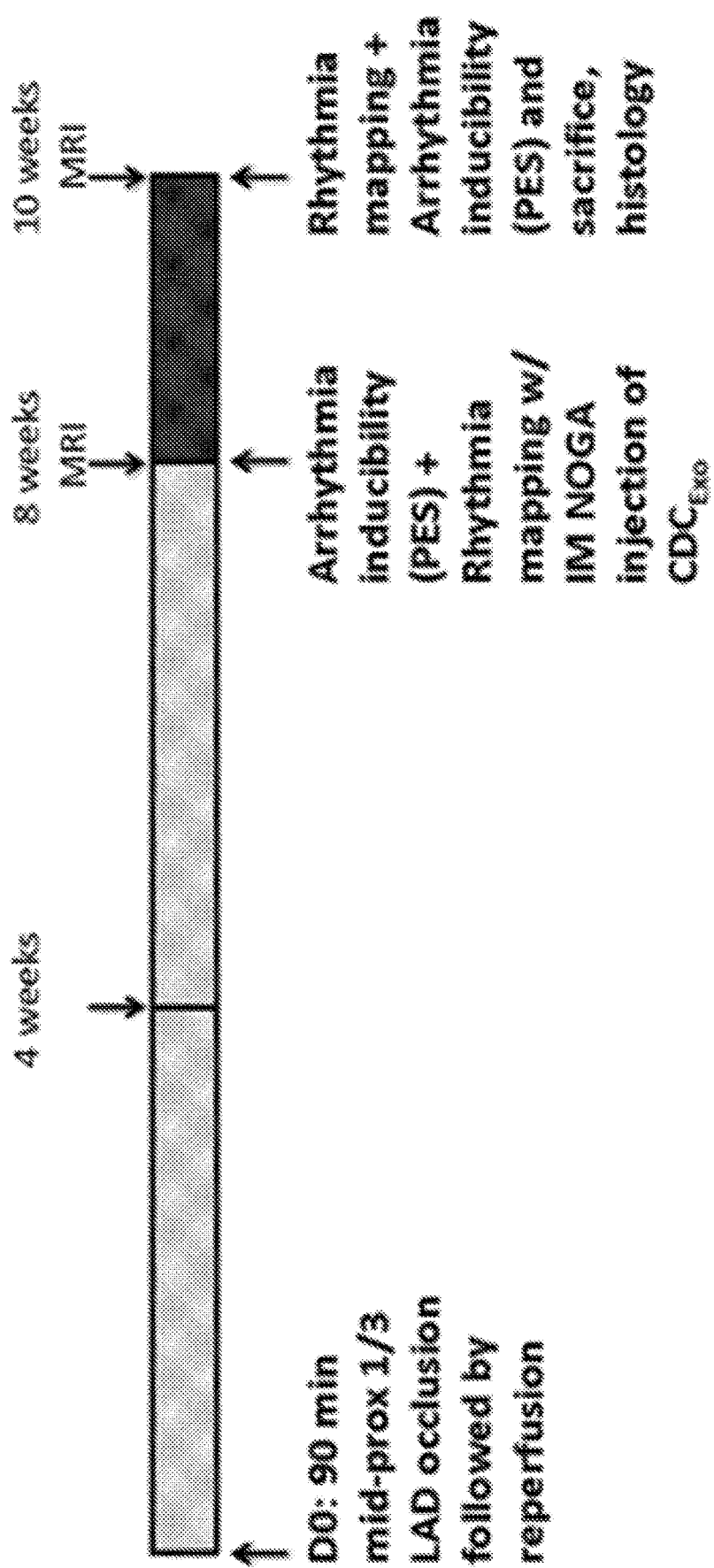
FIG. 6. Study design. Arrthymia inducibility was measured, and electroanatomic mapping (EAM) according to the described timeline.

Previous data suggest CDC's and CDC-derived exosomes reduce infarct size and fibrosis while exhibiting anti-inflammatory properties. Here the Inventors sought to determine if substrate modification with CDC-derived exosomes could diminish late potentials associated with zones of slow conduction and reduce the incidence of inducible ventricular arrhythmias. Study protocol is depicted in FIG. 6.

Arrhythmia Inducibility including programmed electrical stimulation (PES). Arrhythmia susceptibility was probed using programmed electrical stimulation (S1 train of 8 beats at 350-400 ms+1-4 extra-stimuli to ERP). At the LV infarct border zone, and in healthy tissue near the posterolateral wall. If non inducible from the LV the RV was paced. During follow up, animals were paced at the previous site of induction.

Electroanatomic Mapping (EAM) High density mapping (Orion, Boston Scientific, Cambridge, Mass.) with 64 electrodes, 2.5 mm interelectrode spacing, 0.4 mm2 electrode area). Use of 0.5-1.5 mV identified as scar. <0.5 mV dense, transmural scar.

Figure 7:
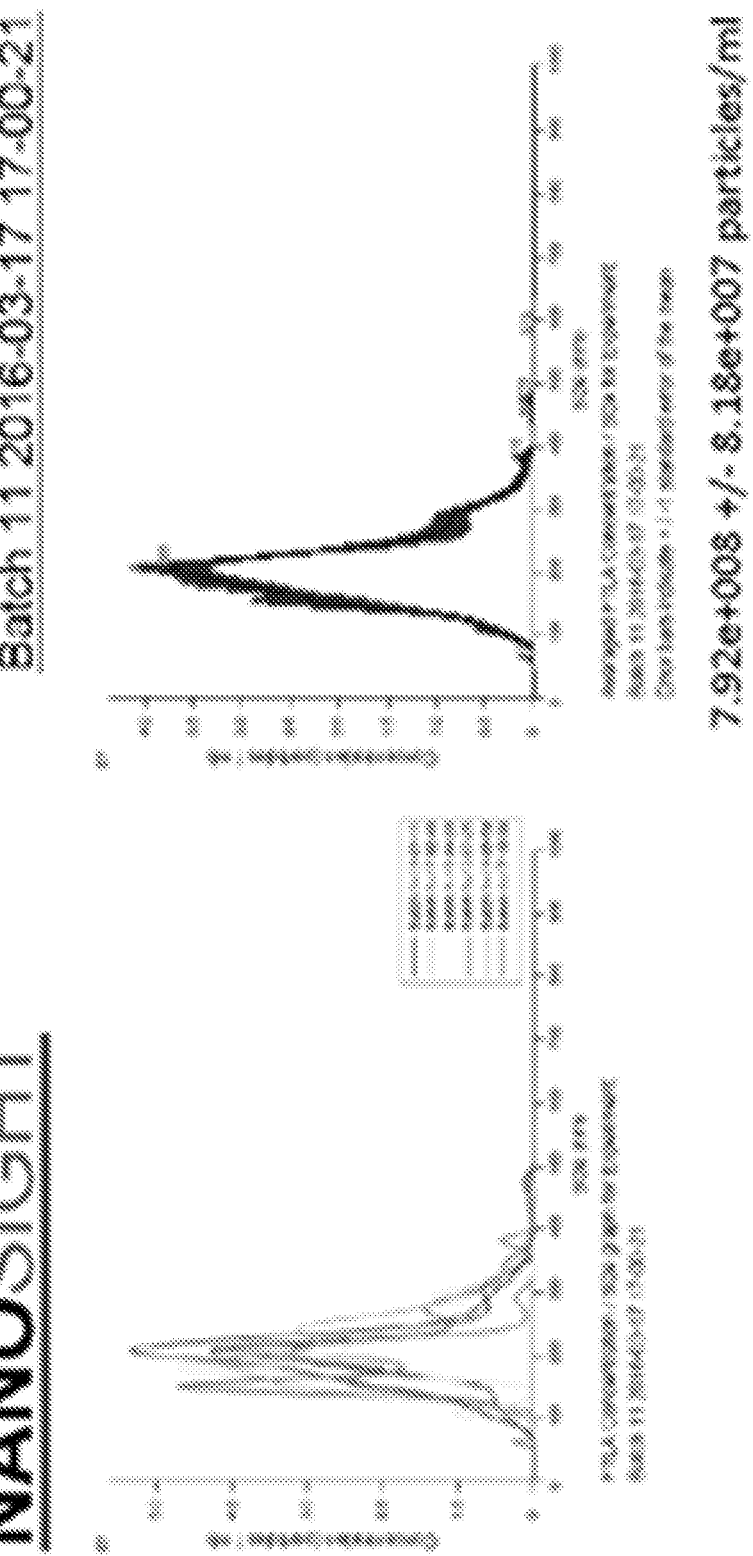
FIG. 7. CDC-derived exosomes design. Nanosight particle tracking was used to determine the number of exosomes.
Figure 8:
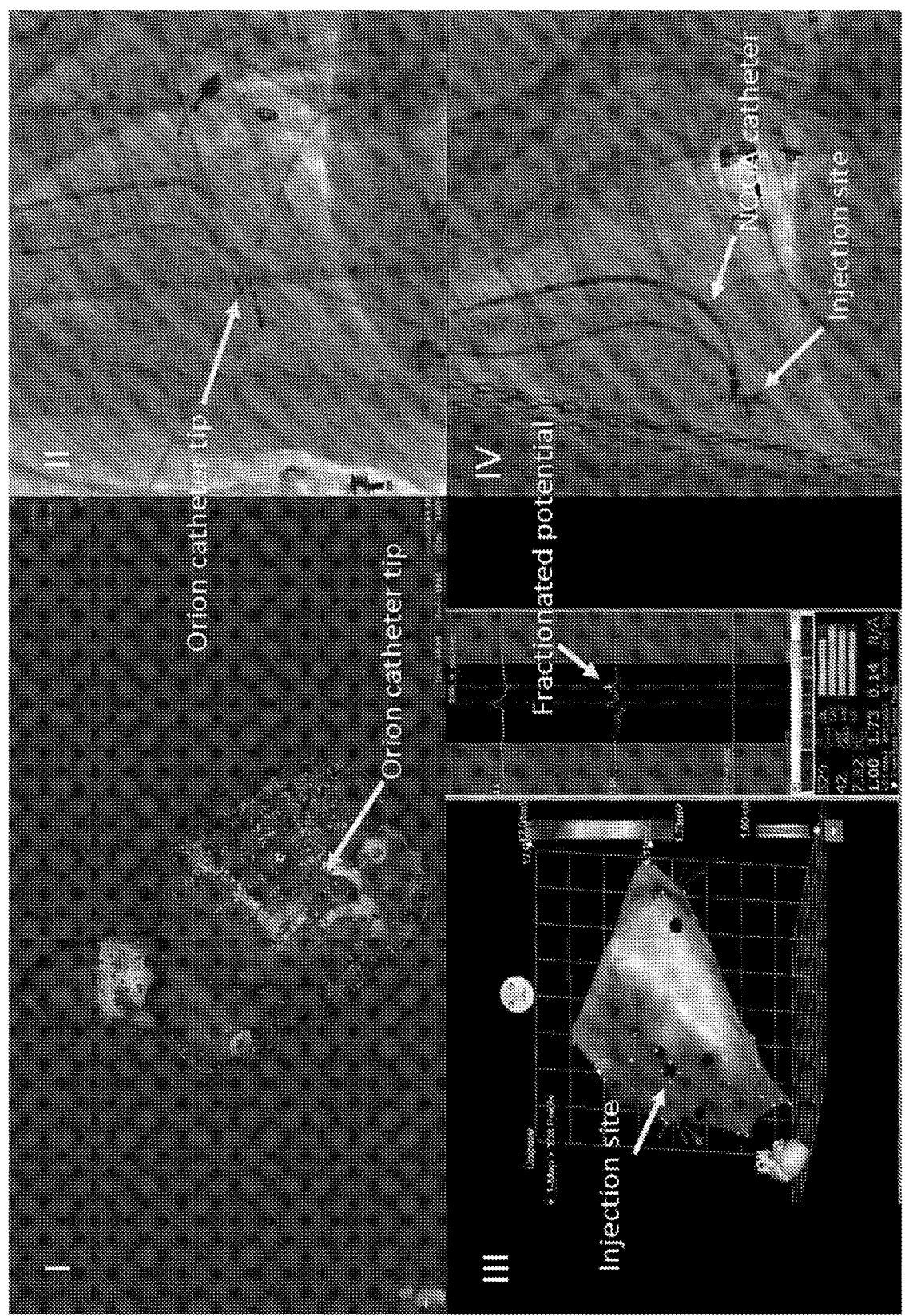
FIG. 8. Electroanatomic Mapping (EAM). High density mapping and tip positioning as shown, with 64 electrodes, 2.5 mm interelectrode spacing, 0.4 mm2 electrode area). 0.5-1.5 mV identified as scar. <0.5 mV dense, transmural scar.

For CDC-derived exosomes dosing, 7.5 mg of CDC-derived exosomes in delivered in 2 ml of IMDM, 6-8 injections of 250 ul-330 ul. Particle tracking is shown in FIG. 7 with sample batch results shown in Table 1.

TABLE 1

Representative Exosome Batch Particle Results

| Batch | Calculated mg/ml | RIPA | Sample | Mg/ml |
|---|---|---|---|---|
| 11 | 13.196 | 300 | 20 | 0.19794 |

Example 2

Results

Figure 9:
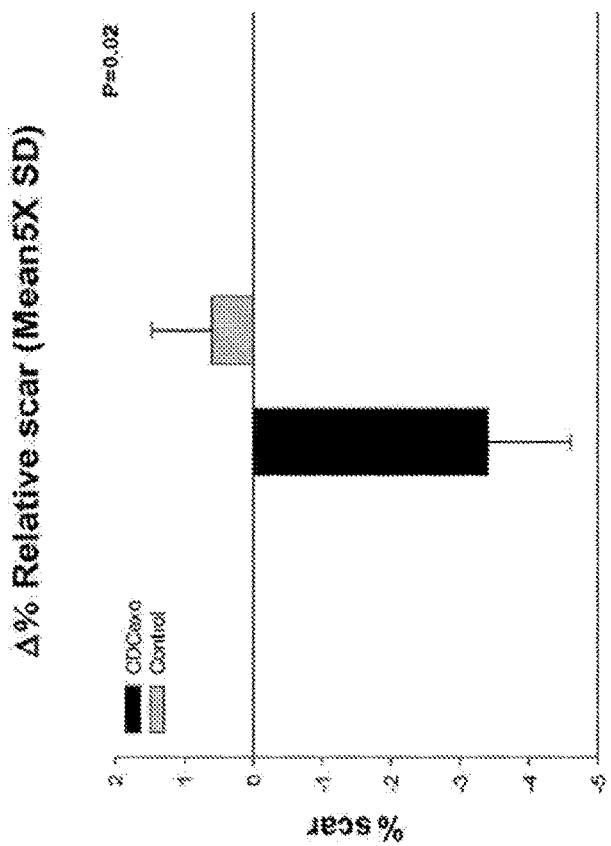
FIG. 9. MRI Data (scar). Changes in both full width and mean standard deviation for CDC-derived exosomes (CDCexo) administered, and control are shown. N=5 for CDCexo and control.
Figure 9:
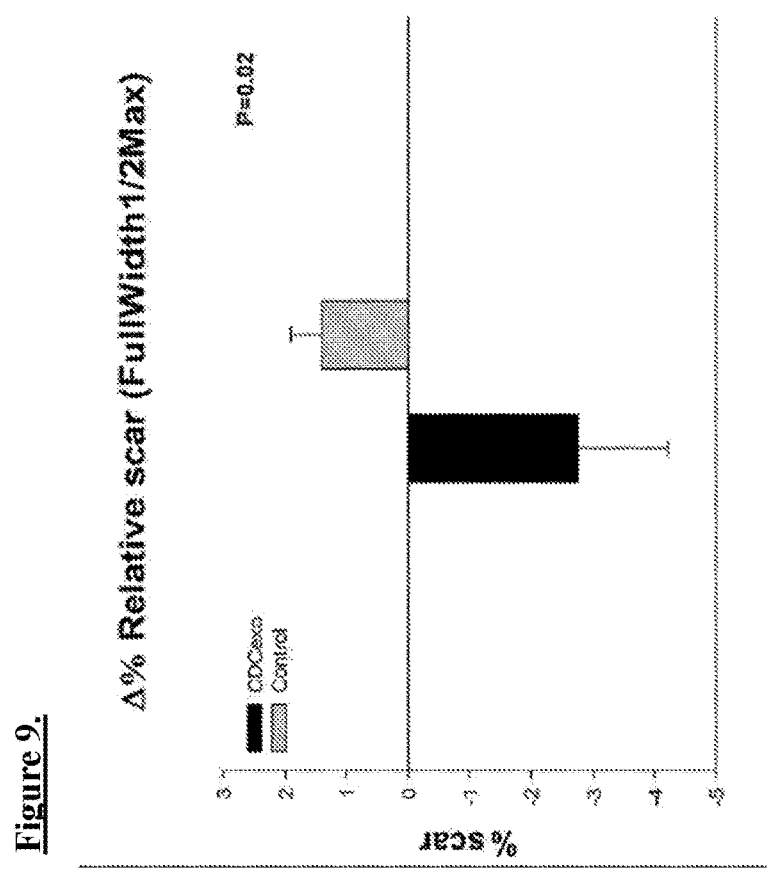
Figure 10:
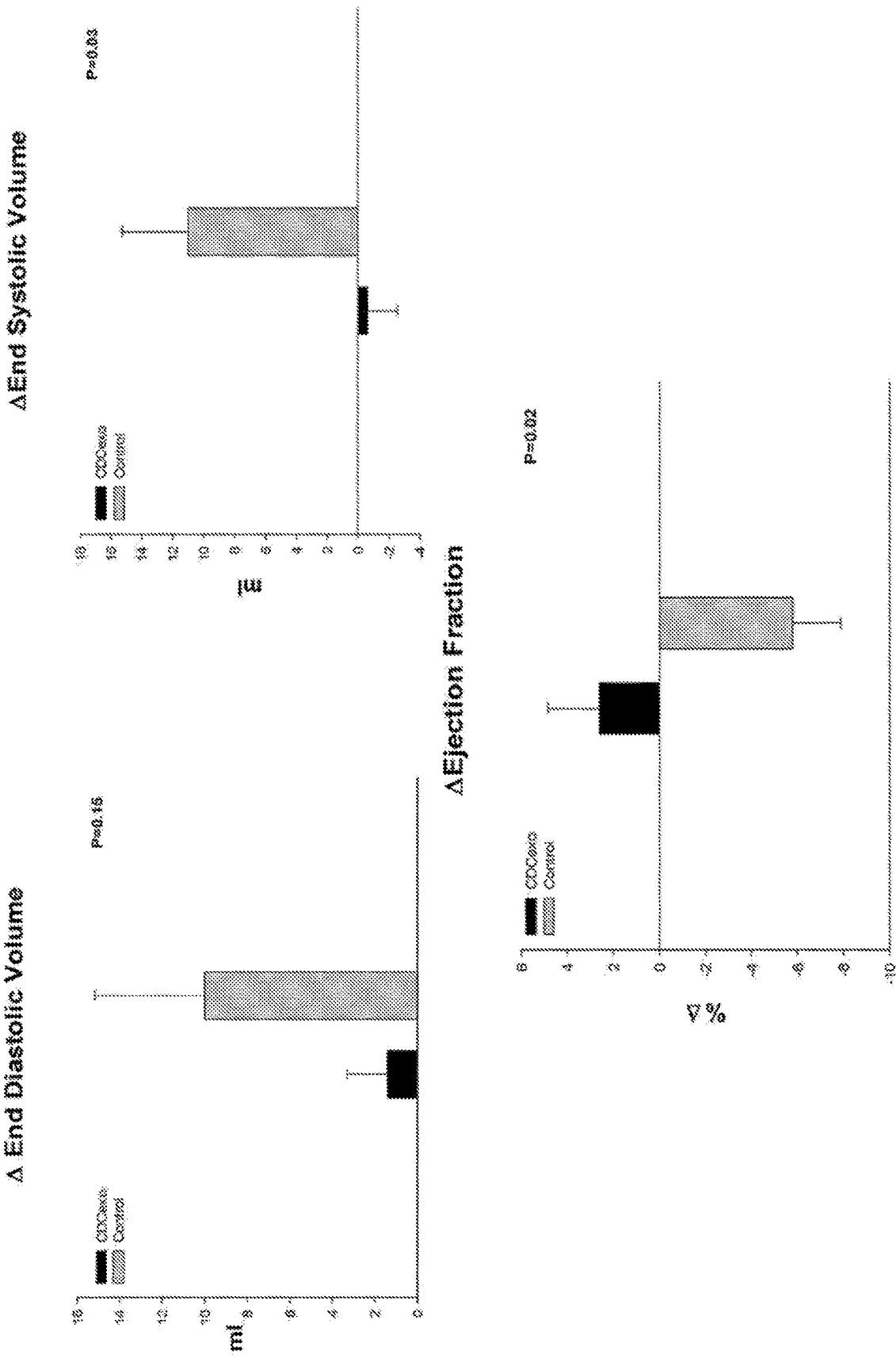
FIG. 10. MRI Data (function). Changes in end diastolic, systolic and ejection fractions are shown for CDC-derived exosomes (CDCexo) administered, and control are shown. N=5 for CDCexo and control.
Figure 11:
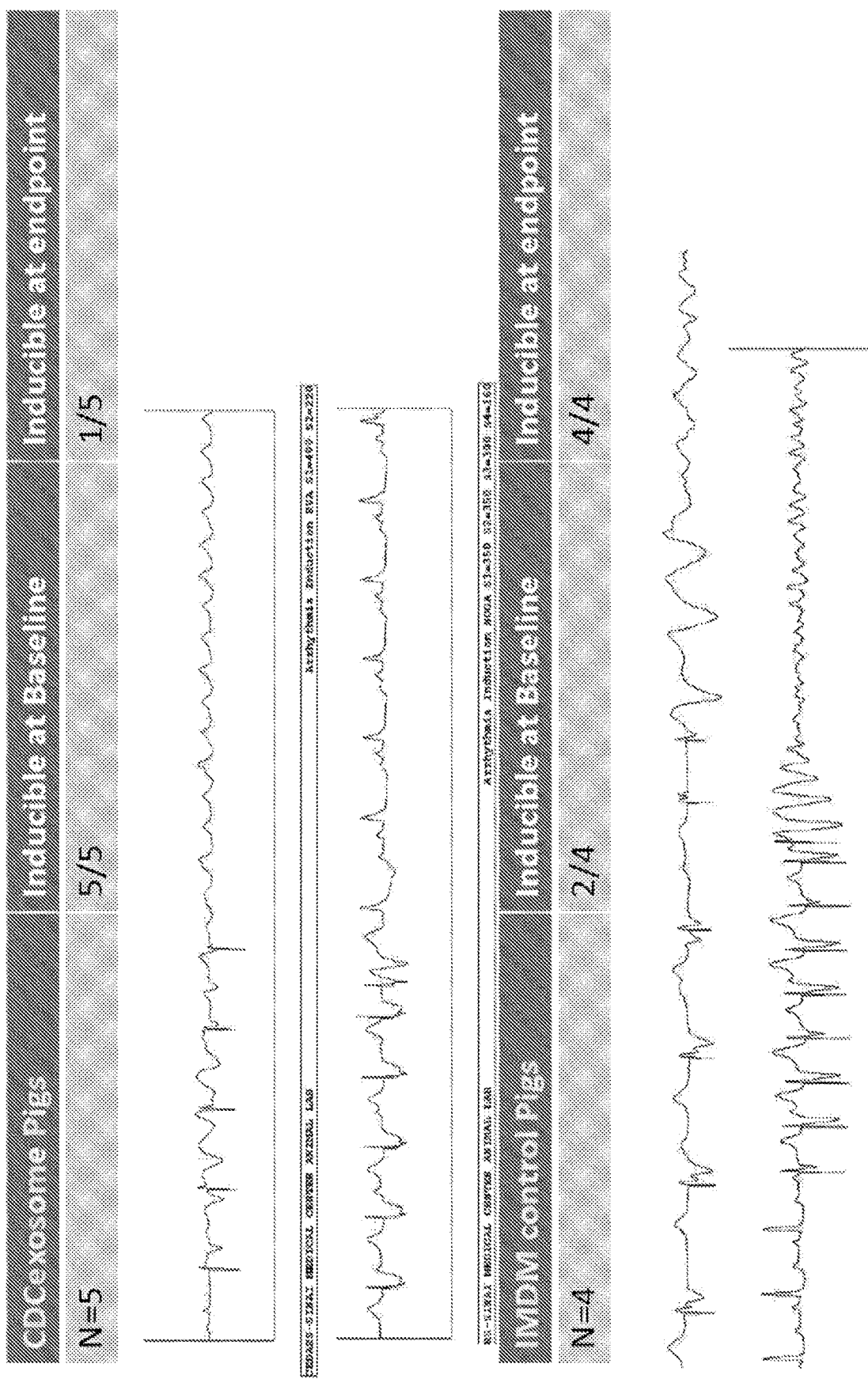
FIG. 11. Arrthymia inducibility. Programmed electrical stimulation (PES) results shown for CDC-derived exosomes administered and control animals.

Following exosome administration, a striking decrease in scar formation was observed in CDC-derived exosomes animals compared to control a shown in FIG. 9. Functional improvements were also observed in diastolic and systolic volume and ejection fraction as shown in FIG. 10. Programmed electrical stimulation also revealed that CDC exosome administered animals had reduced induction at endpoint compared to controls, as shown in FIG. 11.

Example 3

Additional Results

Figure 12:
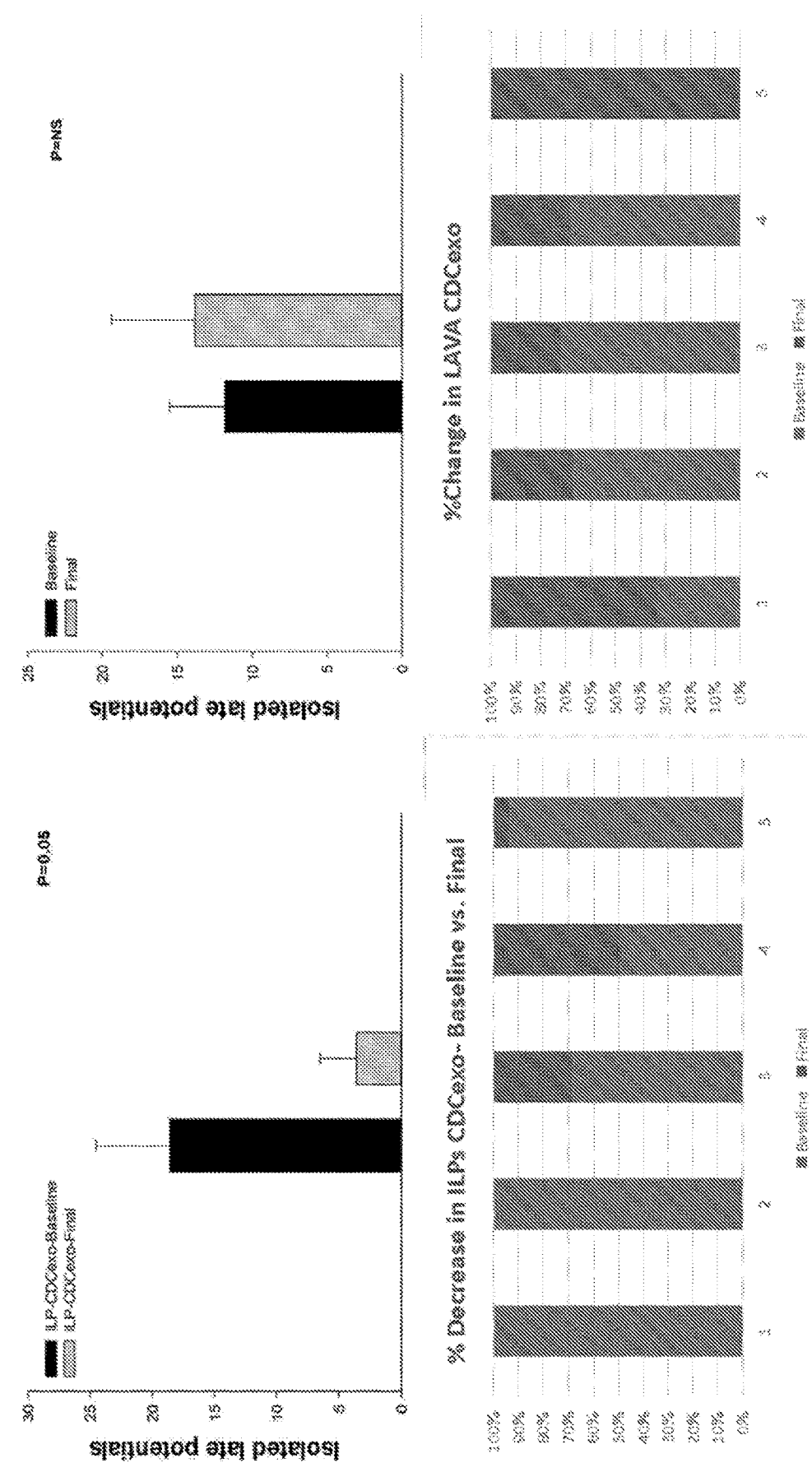
FIG. 12. Electroanatomic Mapping (EAM) demonstrating results for change in number and percentage of late potentials as baseline and final measurements for CDC-derived exosomes (CDCexo) administered, and control. N=5 for CDCexo and control.
Figure 13:
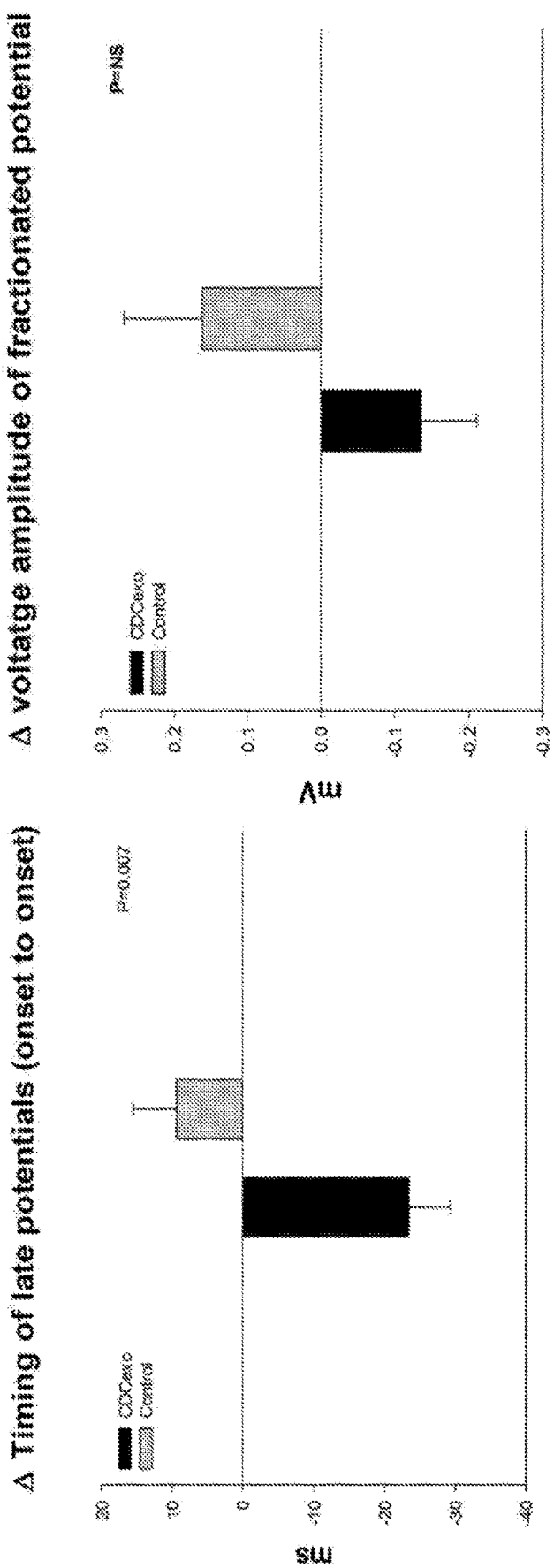
FIG. 13. Electroanatomic Mapping (EAM) demonstrating results for change in timing of late potentials and voltage amplitude of fractionated potential for CDC-derived exosomes (CDCexo) administered, and control.
Figure 14:
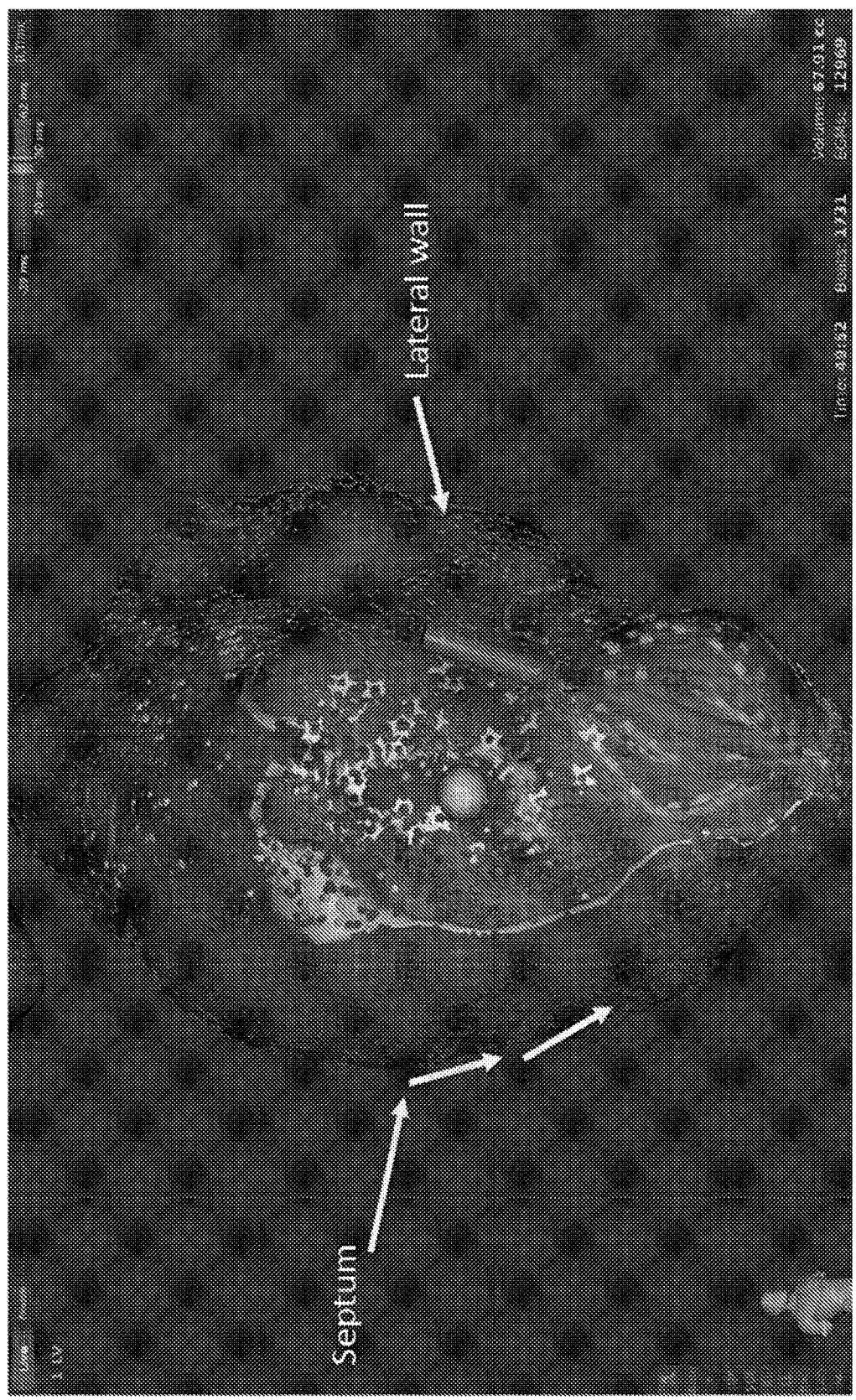
FIG. 14. Electroanatomic map. Representation of CDC-derived exosomes (CDCexo) administered heart at baseline measurement with septum and lateral wall regions highlighted.
Figure 15:
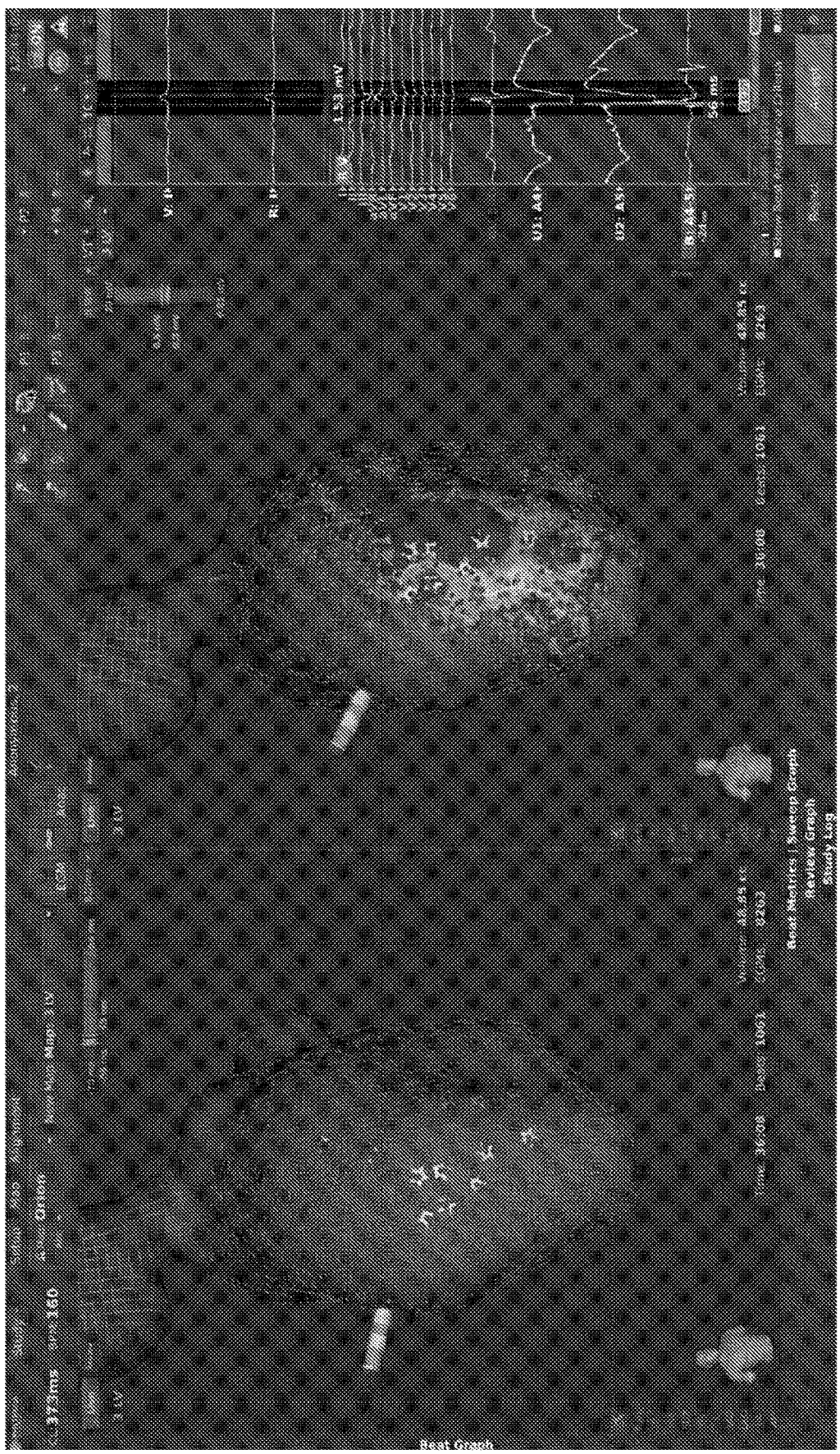
FIG. 15. Electroanatomic map. Representation of CDC-derived exosomes (CDCexo) administered heart at final measurement.
Figure 16:
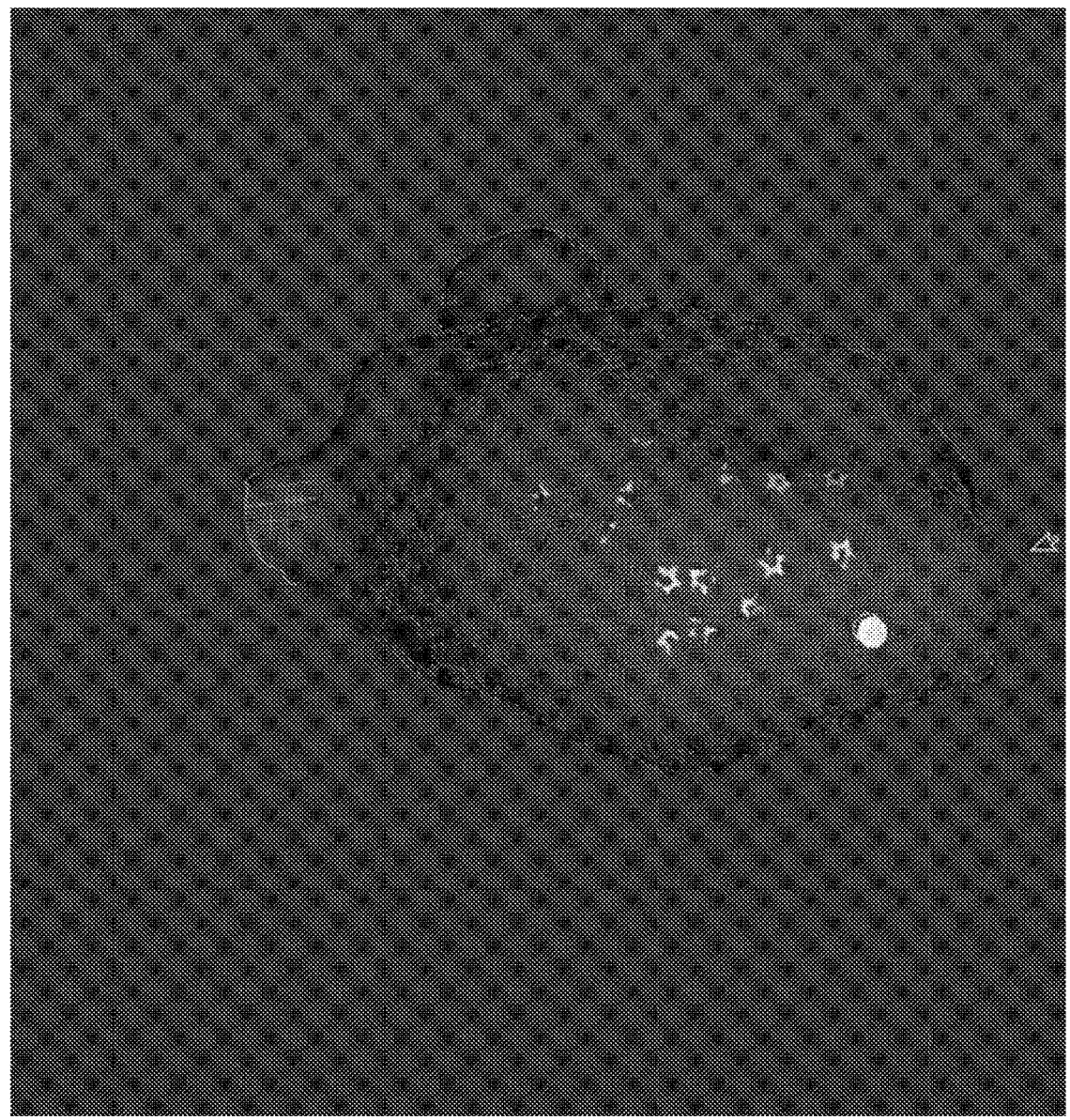
FIG. 16. Electroanatomic map. Additional representation of CDC-derived exosomes (CDCexo) administered heart at final measurement.
Figure 17:
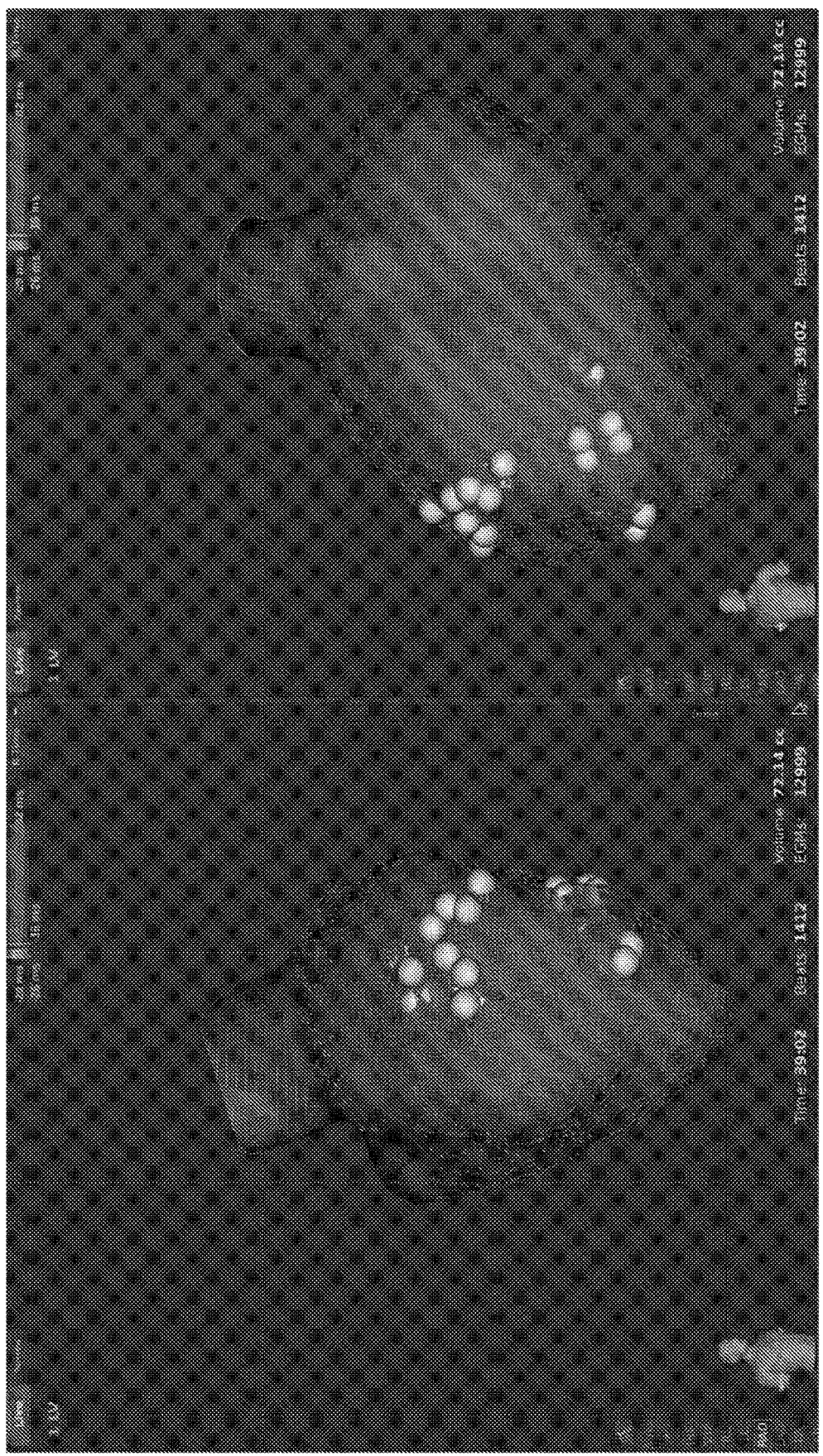
FIG. 17. Electroanatomic map. Second Representation of CDC-derived exosomes (CDCexo) administered heart at baseline measurement.
Figure 18:
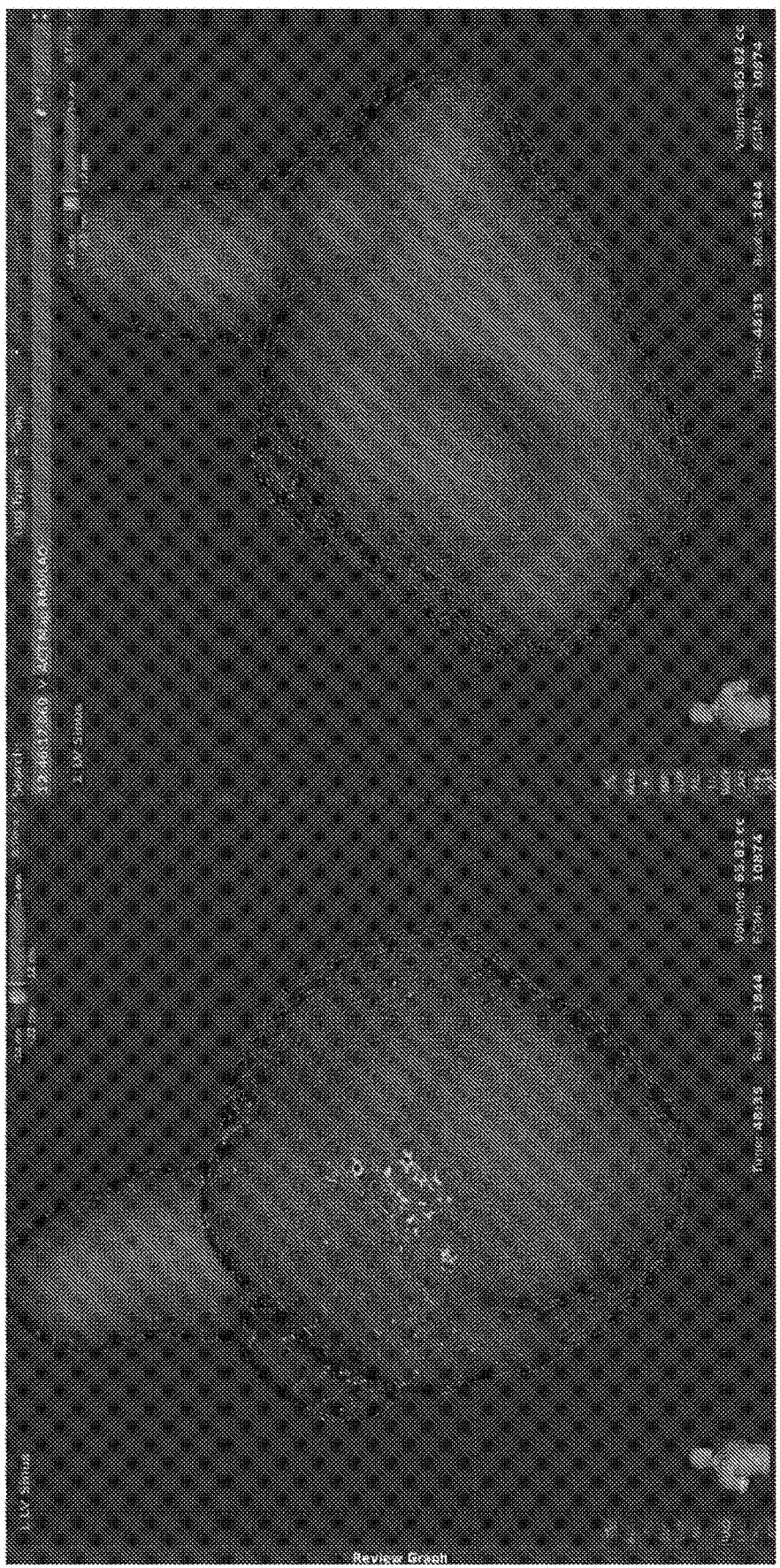
FIG. 18. Electroanatomic map. Second Representation of CDC-derived exosomes (CDCexo) administered heart at final measurement.
Figure 19:
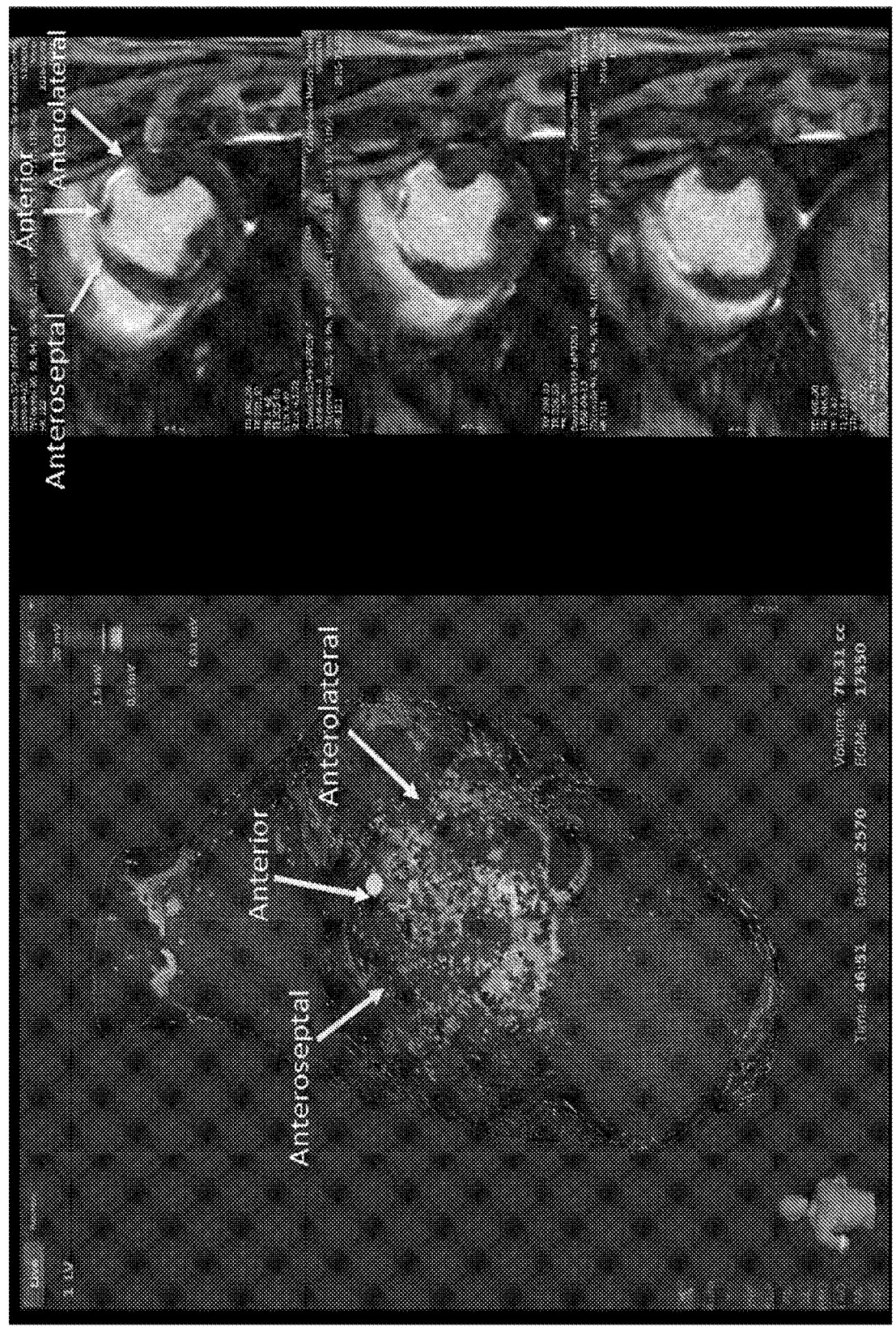
FIG. 19. Electroanatomic map. Anterosteptal, anterior, anterolateral regions are highlighted.
Figure 20:
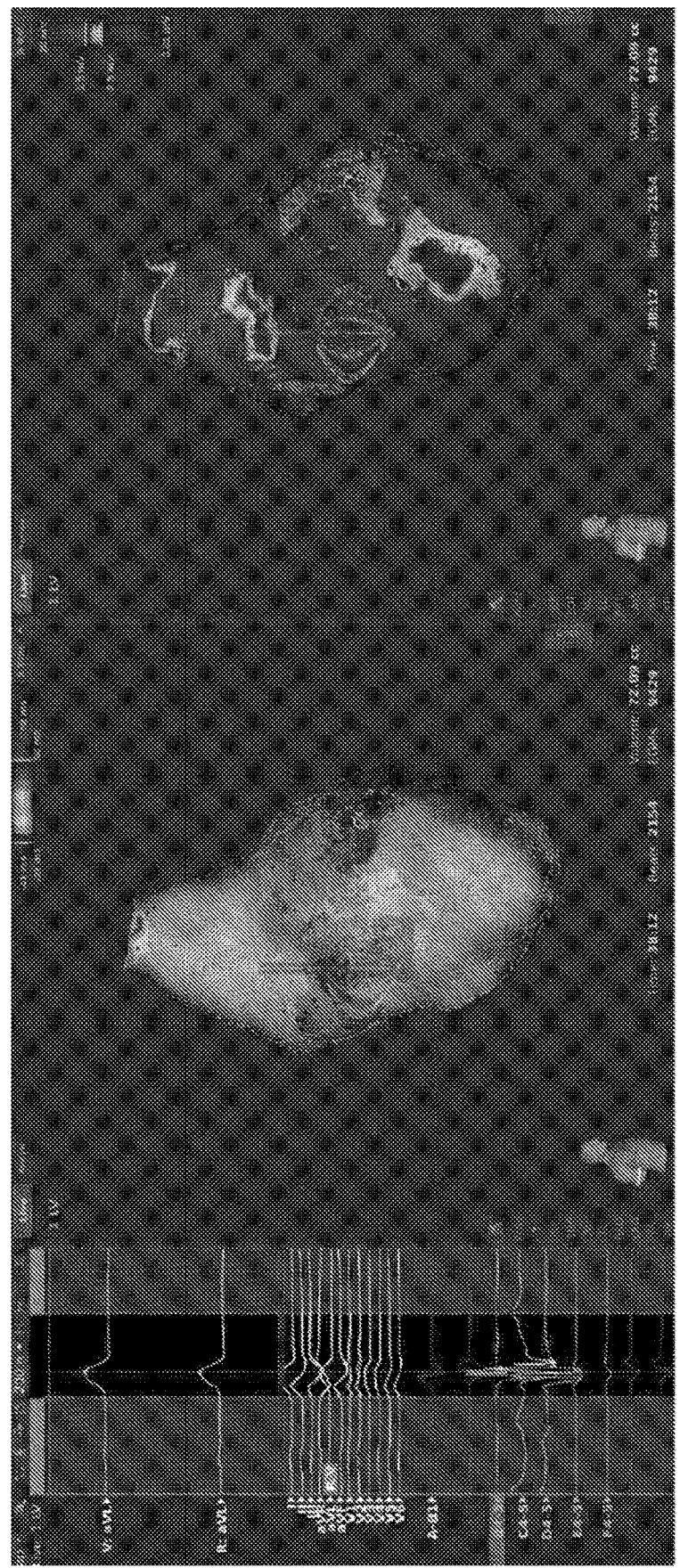
FIG. 20. Electroanatomic map. Demonstrating potential measurements in anatomical space.
Figure 21:
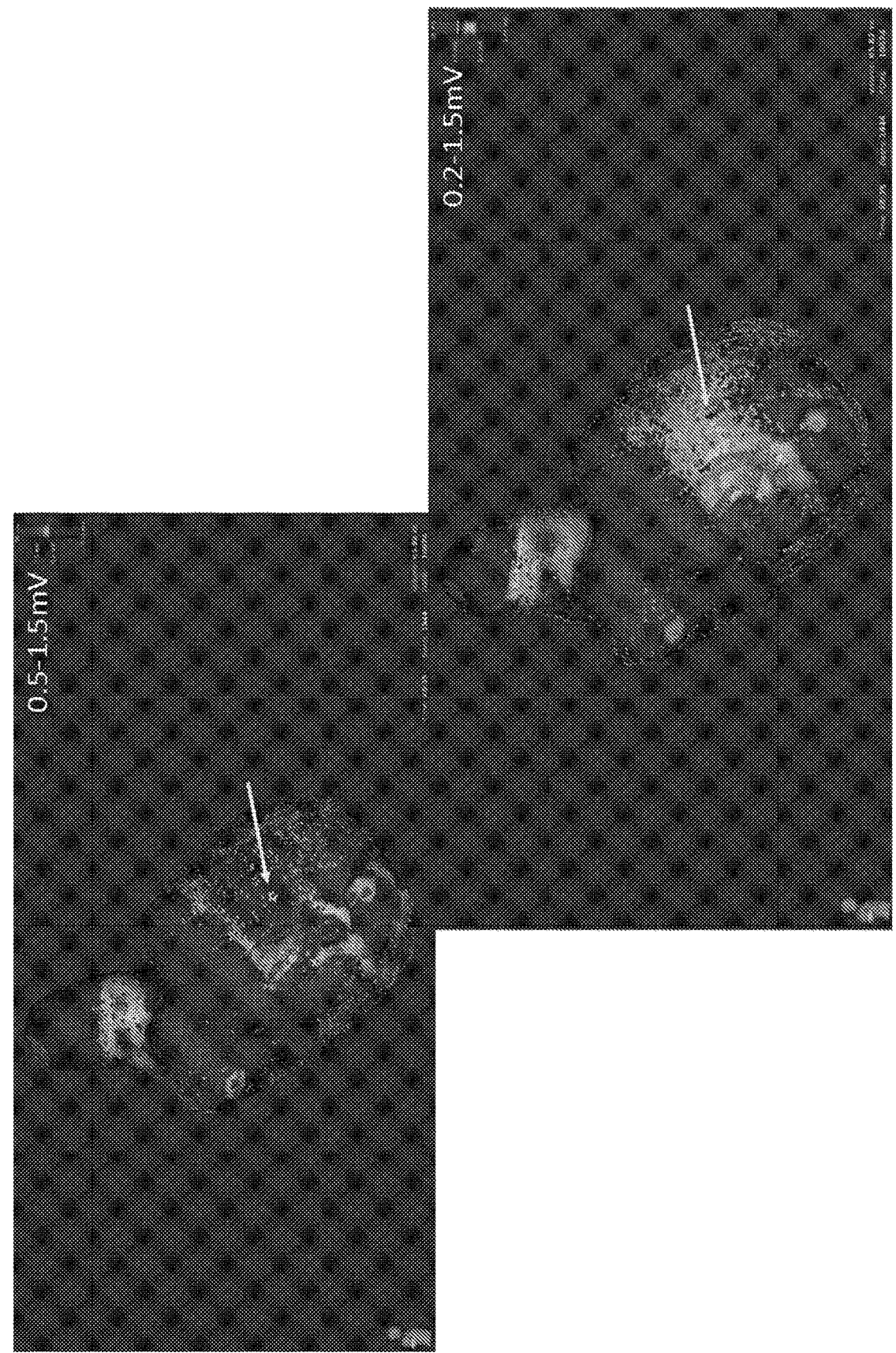
FIG. 21. Electroanatomic map.
Figure 22:
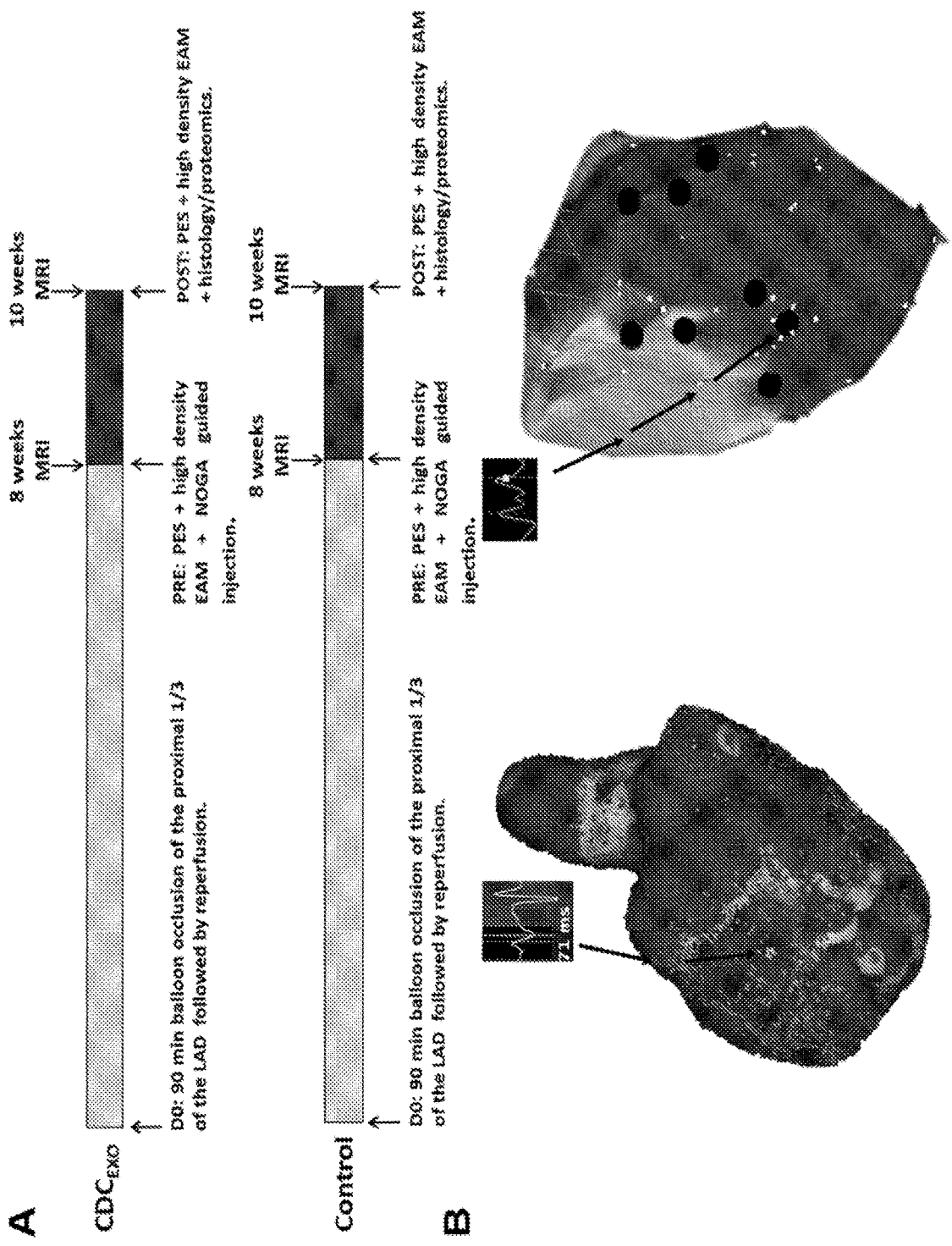
FIG. 22.

Electroanatomic mapping (EAM) revealed the full effect of CDC-derived exosomes administration. Specifically, a dramatic decrease in late potential as observed as a result of CDC-derived exosomes administration in animals compared to controls, as shown in FIG. 12. Moreover, these results were confirmed by observing the increase change in timing and voltage of potentials in control animals, which were both decreased in CDC-derived exosomes administered animals as shown in FIG. 13.

Example 4

Summary

CDC-derived exosomes delivered by IM endocardial injection can diminish the total amount of isolated late potentials associated with an isthmus of slow conduction, while reducing the isoelectric interval between late abnormal ventricular activity and decreasing the incidence of inducible ventricular arrhythmias in a large animal model of chronic MI.

Example 5

CDC-Exosome Isolation and Characterization

Human CDCs at fifth passage (from a single non-diseased human donor) were grown until confluence in regular CDC culture media, which was then changed to serum-free media. After 15 days, the exosome rich conditioned media was collected and filtered through a 450 nm filter. Exosomes were then isolated by ultrafiltration by centrifugation followed by overnight precipitation in 25% poly-ethylene glycol (PEG). The media containing PEG was centrifuged for 30 minutes at 2000 g and the pellet containing the exosomes (7.5 mg) was resuspended in 2 ml of IMDM for injection. Protein concentration was measured using the Bradford protein assay, and particle quantification and size was analyzed with a nanoparticle tracking analysis system (NTA, NanoSight Ltd., Amesbury, Wiltshire, United Kingdom).

Example 6

Swine Infarct Model

Myocardial infarction was induced in 15 female Yucatan mini-pigs (YMPs). Age matched animals of similar size (30-35 kg) were enrolled, facilitating a favorable growth curve over the 2-month experimental protocol. A standard balloon angioplasty catheter (TREK) was advanced distal to the first diagonal branch at the proximal third of the left anterior descending artery. The balloon was inflated for 90 minutes, followed by 8 weeks of reperfusion. Cardiac MRI was performed during week 8, followed by an electrophysiology study, electroanatomic mapping, and an endocardial injection 2-5 days later. 8 weeks following acute injury, adverse ventricular remodeling and QRS complex changes (delayed repolarization) were evident by in all pigs enrolled 8 weeks post MI. This study was performed on a protocol approved by the institutional animal care and use committee at Cedars-Sinai Medical Center.

Example 7

Magnetic Resonance Imaging

MRI was performed on a 3.0 Tesla MRI scanner (Siemens Magnetom Verio, Erlangen, Germany) 8 weeks following MI, and 2 weeks following delivery of Scar size (scar mass divided by LV mass), left ventricular chamber volumes and LVEF were measured using image processing software (Cvi42, Circle Cardiovascular Imaging Inc., Calgary, Canada). Six-millimeter short-axis slices were acquired from the apex to the mitral valve plane. LV volumes were assessed using ECG-gated, breath-hold, cine steady-state free precession acquisitions. Scar mass and scar size were calculated using delayed contrast-enhanced sequences (acquired 8 min following IV injection of Gadolinium-based contrast agent). The scar area was defined by both the mean 5× standard deviation and using the full width at half maximum criterion by including all pixels with >50% maximal signal intensity.

Example 8

Electrophysiology Study

A quadripolar catheter was connected to an electronic recording/stimulator system (EP Workmate, St. Jude Medical); programmed electrical stimulation (PES) was performed. The catheter was advanced under fluoroscopic guidance and positioned at the left ventricular border zone, and the RV apex respectively. A drive train of 8 beats (51), at 20 mA with 3 second rest time and a pulse width of 2 ms. This was followed by up to 3 extra-stimuli (S2-S4) with progressively decreasing cycle length (−10 ms) until the effective refractory period (ERP) was reached at each location. PES was performed during baseline and follow up exams.

Example 9

Electro Anatomical Mapping and Focal Exosome Delivery

Activation and voltage mapping was performed using Rhythmia mapping system (Rhythmia, Boston Scientific, Cambridge, Mass.). Electroanatomic mapping (EAM) for injection was performed using NOGA® EAM system with injection through the Myostar® catheter. Intracardiac electrograms for analysis were acquired with the Orion mini-basket catheter (Rhythmia, Boston Scientific, Cambridge, Mass.). The Orion is an 8.5F catheter consisting of a 64-electrode array on a mini-basket containing 8 splines each with 8 electrodes, 0.4 mm$^2$ with interelectrode spacing of 2.5 mm, center to center. The catheter was advanced through a carotid artery sheath, passed the aortic valve to the left ventricular apex. Local activation was determined based on bipolar and unipolar electrogram morphology and catheter contact with repeatable near-field potentials. Maps were acquired during sinus rhythm. Data acquisition was automated utilizing established acceptance criteria 1) TCL stability (±5 ms); 12 lead ECG morphology match; time stability of a reference electrogram positioned at the RV apex; and beat to beat ECG consistency (>3 beats with similar electrogram morphology and timing; and respiratory stability allowing data acquisition at a constant respiratory phase. Isolated late potentials were identified with a near field amplitude greater than 0.3 mv, occurring after the normal QRS duration of the mini pig (+55 ms) while meeting general beat acceptance criteria described above. Near field electrogram morphology was confirmed with (Insert Rhythmia contact criteria here if not redundant). Late potentials were quantified manually from high density maps by 3 independent reviewers.

8 weeks following MI 12 animals were randomized to receive IM injection of vehicle (IMDM, n=6) or of CDC-derived exosomes (CDC$_{EXO}$ 7.5 mg, n=6). Animals were then followed for 2 weeks where EAM, MRI and PES were repeated prior to sacrifice. EAM of the substrate by NOGA was performed prior to injection. The location of previously identified bipolar ORION catheter tip potentials served as a fluoroscopic reference for the NOGA map. Bipolar map potentials from the Myostar catheter (Myostar®, Biosense Webster, Inc., Diamond Bar, Calif.) confirmed previously identified late potentials. Once identified, 6-9 injections were performed in the intra and peri-infarct zone of the LV.

Example 10

Histology

Samples from the infarcted, border and remote areas were cut in 4 μm sections after fixation in 10% formalin and paraffin embedding. Slides were then deparaffinized and stained with Picrosirius red for evaluation of collagen deposition. A subset of 5 animals were selected for evaluation of cell proliferation by 5-bromo-2'-deoxyuridine (BrdU). CDC$_{EXO}$ pigs (n=3), and those who received vehicle only (n=2) were given an IV injection of BrdU (10 mg/kg) q48 hours during the 2 week follow up period. Following sacrifice, tissue was then collected as described above. Following deparaffinization immunohistochemistry (IHC) by confocal microscopy at 63× was performed. Slides were stained with alpha-sacromeric actinin (α-SA), wheat germ agglutination (WGA), BrdU, and 4',6-diamidino-2-phenylindole (DAPI). Cells which were double positive for α-SA, and BrdU were quantified and evaluated as a ratio of the total α-SA positive cells. H&E staining was then performed in the same subset of animals to evaluate the non-cardiomyocyte population.

Example 11

Computational Cardiology

A biophysically-detailed three-dimensional (3D) ventricular model of one of the porcine hearts used in this research was constructed from the contrast-enhanced MRI scans. The ventricular walls were segmented semi-automatically using a previously described methodology. Pixels within the ventricular walls were classified as infarcted, gray zone (GZ), or non-infarcted based on thresholding of signal intensity. Two models of the same porcine heart were constructed, one before and another after cardiosphere treatment, reflecting the different distribution of structural remodeling in the area of injection. Fiber orientation was incorporated in the reconstructed model as described previously. Cellular membrane kinetics and tissue conductivities were assigned using a previously validated methodology. The Inventors applied the Inventors' previously validated protocol to test the inducibility of each ventricular model for sustained arrhythmia from different pacing sites. The simulations were executed using a validated software platform.

Example 12

Statistical Analysis

Data are presented as means±SEM. A two-tailed t test was used to directly compare an $CDC_{EXO}$ pigs vs control pigs which received vehicle alone. A Mann-Whitney test was performed to confirm results from data that was not normally distributed. A two-sided Fisher's Exact test to was used during analysis of PES data at both time points.

Example 13

Infarct Size and Systolic Function

Figure 23:
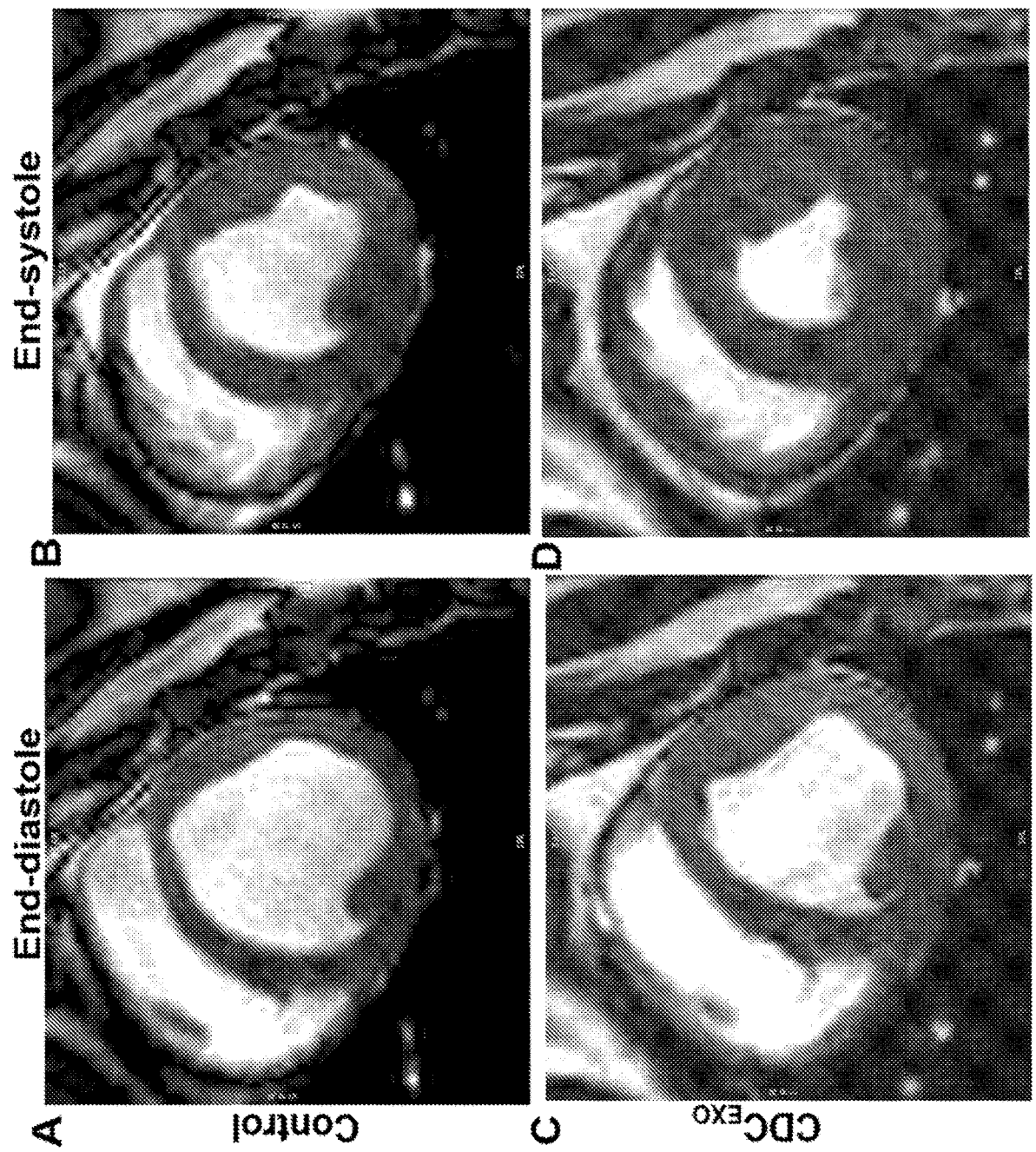
FIG. 23.
Figure 23:
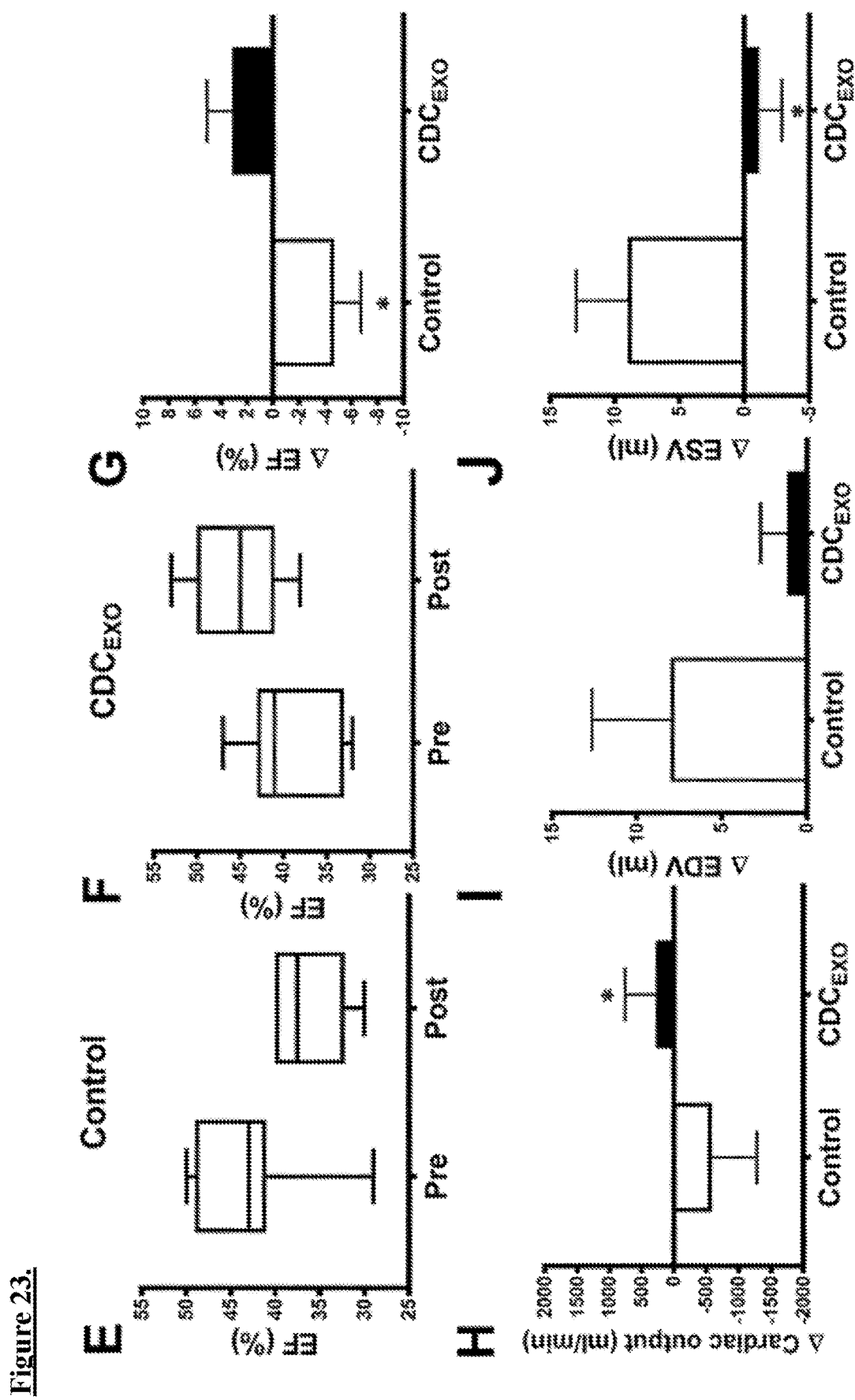
Figure 24:
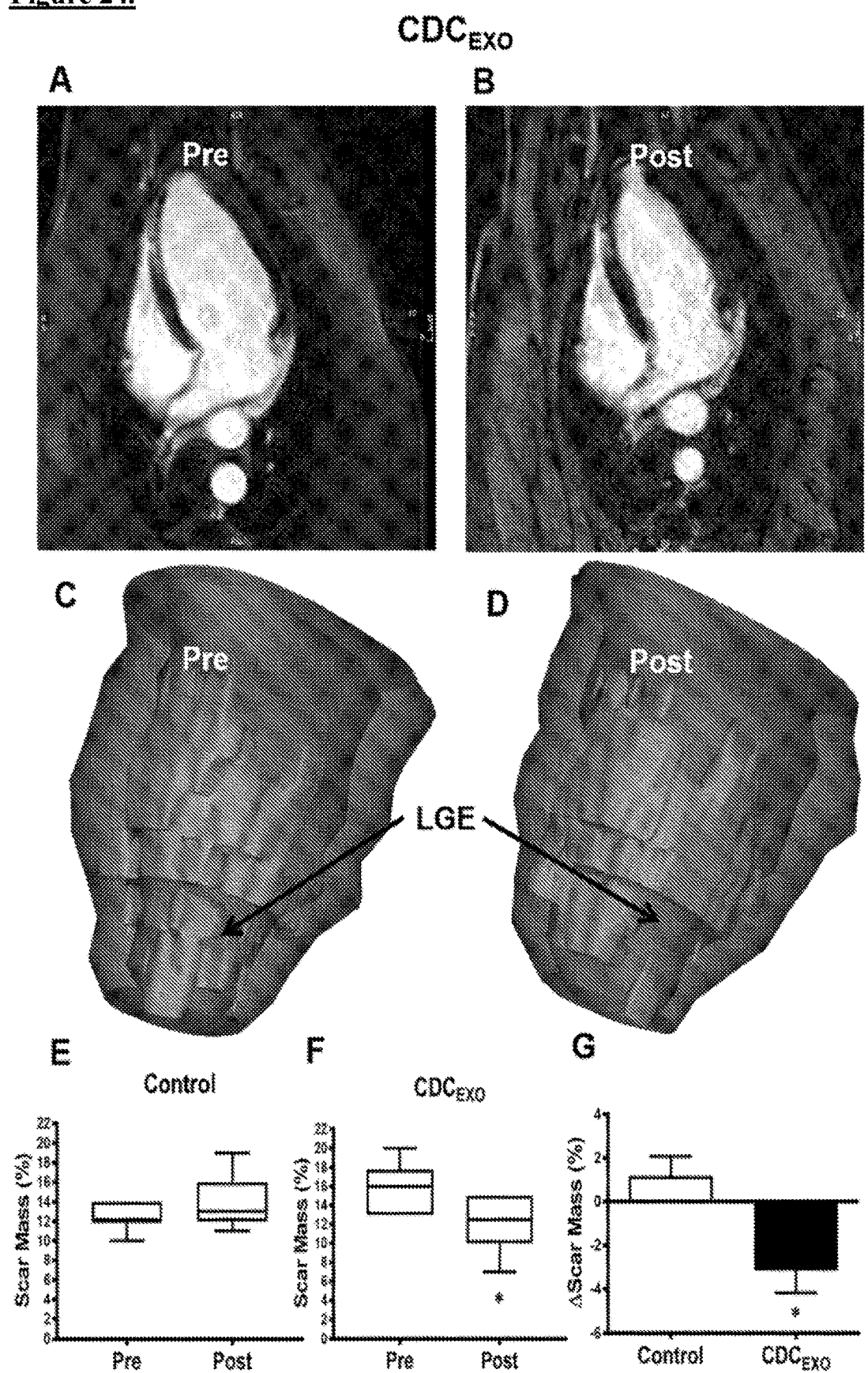
FIG. 24.

MRI data showed noteworthy evidence of improved systolic function with favorable chamber volume(s) in $CDC_{EXO}$ pigs relative to controls. There was a strong trend for improved left ventricular ejection fraction in $CDC_{EXO}$ pigs (Pre: 39.7±2%, Post: 45.3±1.9%, N=7, P=0.07) with deterioration in systolic function in control animals (Pre: 42.3±2.6%, Post: 36.3±1.6%, N=7, P=0.09) (FIG. 23) $CDC_{EXO}$ treated pigs had a significantly higher ejection fraction at endpoint compared to vehicle treated controls (36.3±1.6% control vs 45.3±1.9% $CDC_{EXO}$, P=0.005). The Δ LVEF 2 weeks after delivery, was significantly improved in $CDC_{EXO}$ pigs relative to controls (−4.7±2.04% control vs 3.16±1.92% $CDC_{EXO}$, P=0.01). Cardiac output in pigs receiving injections of $CDC_{EXO}$ was significantly improved in the $CDC_{EXO}$ group (−586±264.3 ml/min control, vs 278.1±181 ml/min $CDC_{EXO}$, P=0.01). LV end systolic volume (ESV) was improved in $CDC_{EXO}$ pigs and degenerated in controls (9±3.4 ml, control N=7, vs. −1.1±1.4 ml, $CDC_{EXO}$ N=7, P=0.01). Chamber dilation evaluated by increases in end-diastolic volume (EDV) were more attenuated in $CDC_{EXO}$ pigs compared to controls (8±4 ml control, vs. 1.1±1.5 ml, $CDC_{EXO}$ P=ns). Over the 2-week follow-up period LV mass was increased proportionately in both animal groups. A significant decrease in absolute scar mass was observed in $CDC_{EXO}$ pigs and not in controls (−3.1±1%, $CDC_{EXO}$ N=7, 1.1±0.7, N=7, P=0.009) (FIG. 24).

Example 14

Electrophysiology Study

Figure 25:
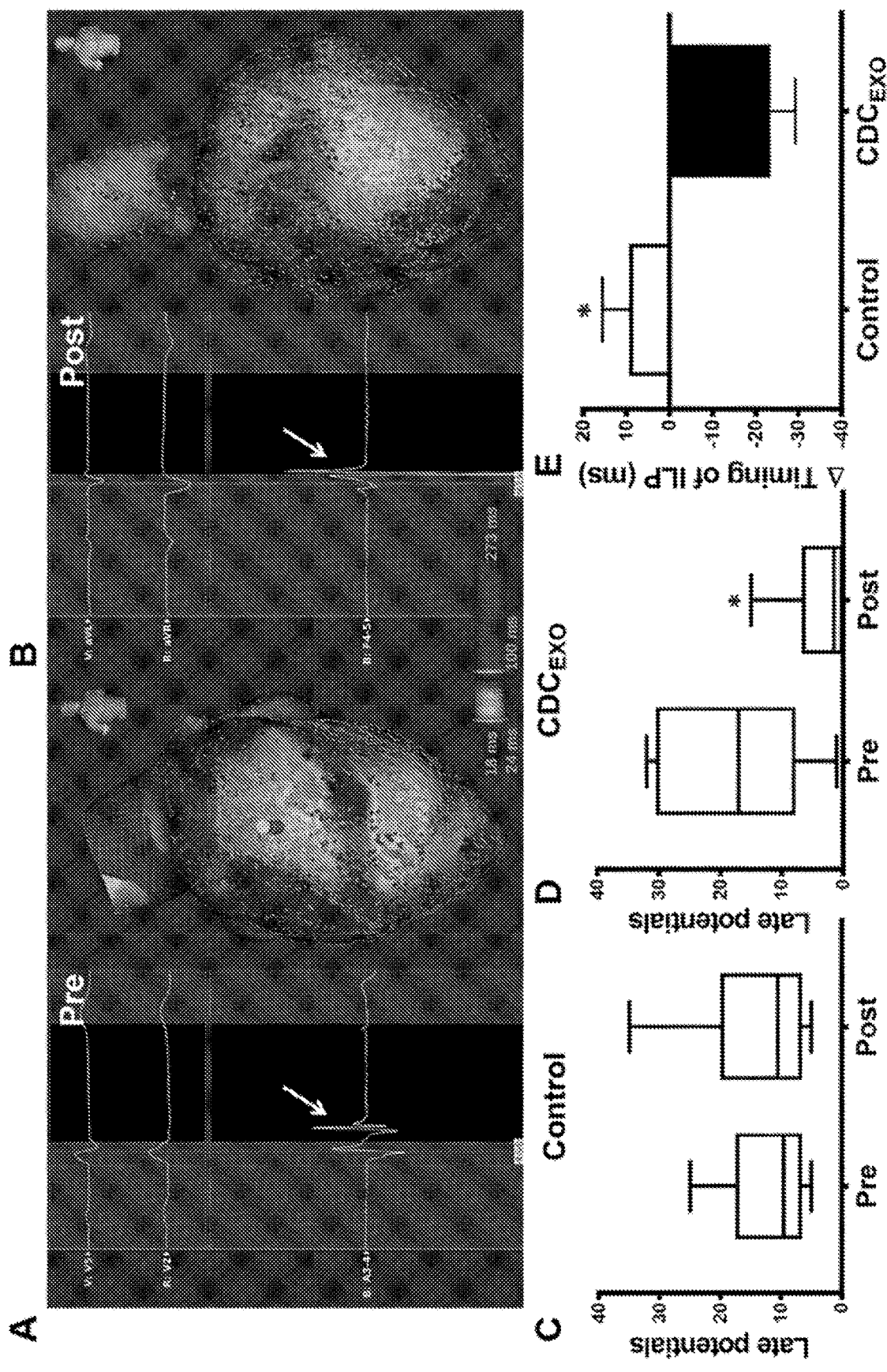
FIG. 25.

PES was performed in 15 animals 8 weeks post MI and again 2 weeks following injection of $CDC_{EXO}$ or IMDM alone as a control. At baseline, a sustained VA was induced in all animals in both groups. However, during the follow up exam 2 weeks later, sustained arrhythmias were identified in only 1 of the 7 $CDC_{EXO}$ pigs, whereas VA remained evident in all of the vehicle treated animals (P=0.001). Identifiable late potentials from high density mapping were significantly reduced in pigs receiving $CDC_{EXO}$ (Pre: 18.6±4.8, post: 3.6±2.3, N=6, P=0.02), where there was an increase in late potentials in control animals (Pre: 11.8±3, post 13.8±4.5, N=6, P=NS) (FIG. 25). Furthermore, identifiable isolated late potentials previously observed within the arrhythmogenic substrate were either completely diminished or electrogram signals displayed a much earlier multicomponent morphology between baseline and endpoint maps ($CDC_{EXO}$ −23.4 ms, N=6 vs. control 9.3 ms, N=6, P=0.0004) FIGS. 26 and 27. Remaining fractionated signals from pigs treated with $CDC_{EXO}$ did not meet baseline criteria of identified late potentials.

Example 15

Computational Cardiology

Image analysis of the reconstructed ventricular models before and after cardiosphere-derived cell (CDC)-derived exosome treatment demonstrated similar global changes as reported experimentally. Specifically, the left ventricle (LV) volume increased (30.47 to 32.49 mL) and volume fraction of scar and GZ decreased (scar: 16.57% to 12.69%; GZ: 7.22% to 6.93%). Following CDC-derived exosome treatment, both scar and GZ in the area of injection in the inferior LV septal wall had significantly diminished (FIG. 29a).

The Inventors used the constructed models to explore the mechanism by which CDC-derived exosome treatment gives rise to decreased arrhythmia inducibility. Before treatment, the model ventricles were inducible for sustained arrhythmia (FIG. 29b, top) following pacing from the right ventricular outflow tract (RVOT), while they were not after CDC-derived exosome treatment (FIG. 29b, bottom). The critical mechanism that gave rise to sustained VT in the non-treated ventricles was the block of the anterior septal wave traveling inferiorly (FIG. 29b, top) at a region of endocardial scar, while other waves propagated undisturbed through the left ventricle (LV) and right ventricle (RV) lateral walls. These waves merged at the apex, managing to propagate superiorly through GZ tissue in the septal infarct zone, returning to the RV and giving rise to sustained reentry. In contrast, in the post-treatment case, the anterior septal wave did not block because the amount of scar was decreased (FIG. 29b, bottom). All propagating wavefronts then converged at the apex, resulting in conduction block. Sustained reentry was not induced in this case

Example 16

Histology

Collagen deposition evaluated with picrosirius red staining (FIG. 28) showed there was significantly less collagen within the IZ of pigs treated with $CDC_{EXO}$ compared to vehicle treated controls (33.33±5.064% n=4 vs 56.73±5.819% n=4, P=0.02). There was no difference in % collagen in the BZ, or RZ. Additionally, within the IZ of pigs injected with $CDC_{EXO}$ there were substantially more identifiable double positive cells (α-SA+BrdU/α-SA) within the dense areas of infarcted myocardium, IZ 0.95±0.21 cells/field (μm$^2$) vs. 3.47±0.19 cells/field (μm$^2$) (P=0.0036).

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of cardiosphere derived cells (CDCs), the use of alternative sources for CDCs, exosomes derived therefrom, method of isolating, characterizing or altering exosomes produced by such cells, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and doses not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of treating ventricular tachycardia, comprising:
injecting a therapeutically effective amount of a composition comprising extracellular vesicles into a myocardium of a subject afflicted with ventricular tachycardia, thereby treating the subject,
wherein the extracellular vesicles are obtained from human cardiosphere-derived cells (CDCs), and
wherein the extracellular vesicles are exosomes.

2. The method of claim 1, wherein the subject has had a myocardial infarction.

3. The method of claim 1, wherein the subject has an implantable cardioverterdefibrillator (ICD).

4. The method of claim 1, wherein the subject was treated with initial antiarrhythmic drug (AAD) therapy.

5. The method of claim 1, wherein the subject was treated with escalating antiarrhythmic drug (AAD) therapy.

6. The method of claim 1, wherein treating the subject comprises a reduction in the number of isolated late potentials.

7. The method of claim 1, wherein treating the subject comprises a reduction in the isoelectric interval between late abnormal ventricular activity.

8. The method of claim 1, wherein treating the subject comprises a decrease in the incidence of inducible ventricular arrhythmias.

* * * * *